United States Patent
Eulenberg et al.

(10) Patent No.: US 7,211,563 B2
(45) Date of Patent: May 1, 2007

(54) PROTEIN DISULFIDE ISOMERASE AND ABC TRANSPORTER HOMOLOGOUS PROTEINS INVOLVED IN THE REGULATION OF ENERGY HOMEOSTASIS

(75) Inventors: Karsten Eulenberg, Göttingen (DE) DEX; Günter Brönner, Göttingen (DE); Thomas Ciossek, Göttingen (DE); Thomas Häder, Göttingen (DE); Arnd Steuernagel, Göttingen (DE)

(73) Assignee: Develogen Aktiengesellschaft fur Entwicklungsbiologische Forschung, Gottingen (DE)

( * ) Notice: Subject to any disclaimer, the term of this patent is extended or adjusted under 35 U.S.C. 154(b) by 76 days.

(21) Appl. No.: 10/473,696

(22) PCT Filed: Mar. 28, 2002

(86) PCT No.: PCT/EP02/03540

§ 371 (c)(1),
(2), (4) Date: Sep. 29, 2003

(87) PCT Pub. No.: WO02/079238

PCT Pub. Date: Oct. 10, 2002

(65) Prior Publication Data

US 2004/0097457 A1    May 20, 2004

(30) Foreign Application Priority Data

Apr. 2, 2001  (EP) ................ 01108315.1
Jun. 1, 2001  (EP) ................ 01113419.4

(51) Int. Cl.
*A61K 38/00* (2006.01)
*C07K 1/00* (2006.01)

(52) U.S. Cl. ........................................ 514/12; 530/350
(58) Field of Classification Search ................ 530/350; 435/69.1; 514/12
See application file for complete search history.

(56) References Cited

U.S. PATENT DOCUMENTS

| 6,060,601 A | 5/2000 | Langhals et al. |
| 6,753,314 B1 * | 6/2004 | Giot et al. ..................... 514/12 |
| 2005/0202421 A1 * | 9/2005 | Hirsch et al. .................. 435/6 |

OTHER PUBLICATIONS

Croop et al., PIR 80 Datbase, accession No. G2068, Dec. 21, 1996.*

* cited by examiner

*Primary Examiner*—Maryam Monshipouri
(74) *Attorney, Agent, or Firm*—Sutherland Asbill & Brennan LLP

(57) ABSTRACT

The present invention discloses three novel proteins regulating the energy homeostasis and the metabolism of triglycerides, and polynucleotides, which identify and encode the proteins disclosed in this invention. The invention also relates to vectors, host cells, antibodies, and recombinant methods for producing the polypeptides and polynucleotides of the invention. The invention also relates to the use of these sequences in the diagnosis, study, prevention, and treatment of diseases and disorders related to body-weight regulation, for example, but not limited to, metabolic diseases such as obesity, as well as related disorders such as adipositas, eating disorders, wasting syndromes (cachexia), pancreatic dysfunctions (such as diabetes mellitus), hypertension, pancreatic dysfunctions, arteriosclerosis, coronary artery disease (CAD), coronary heart disease, hypercholesterolemia, dyslipidemia, osteoarthritis, gallstones, cancer, e.g. cancers of the reproductive organs, sleep apnea, and others.

5 Claims, 26 Drawing Sheets

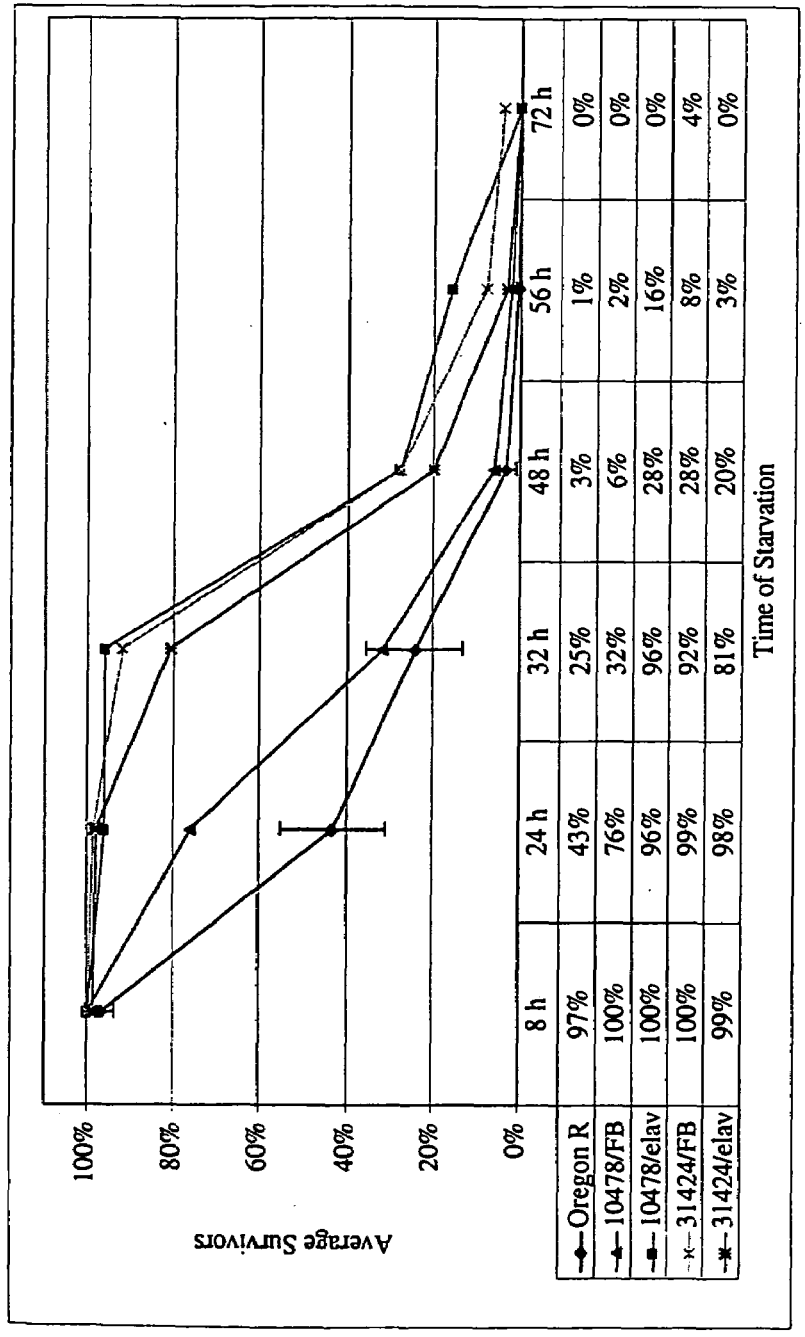
FIGURE 1: Increase of starvation resistance of HD-EP(X)10478 and HD-EP(X)31424 flies by expression using "FB- or elav-Gal4 driver"

FIGURE 2: Increase of triglyceride content of HD-EP(X)10478 and 31424 flies by ectopic expression using "FB- or elav-Gal4 driver"
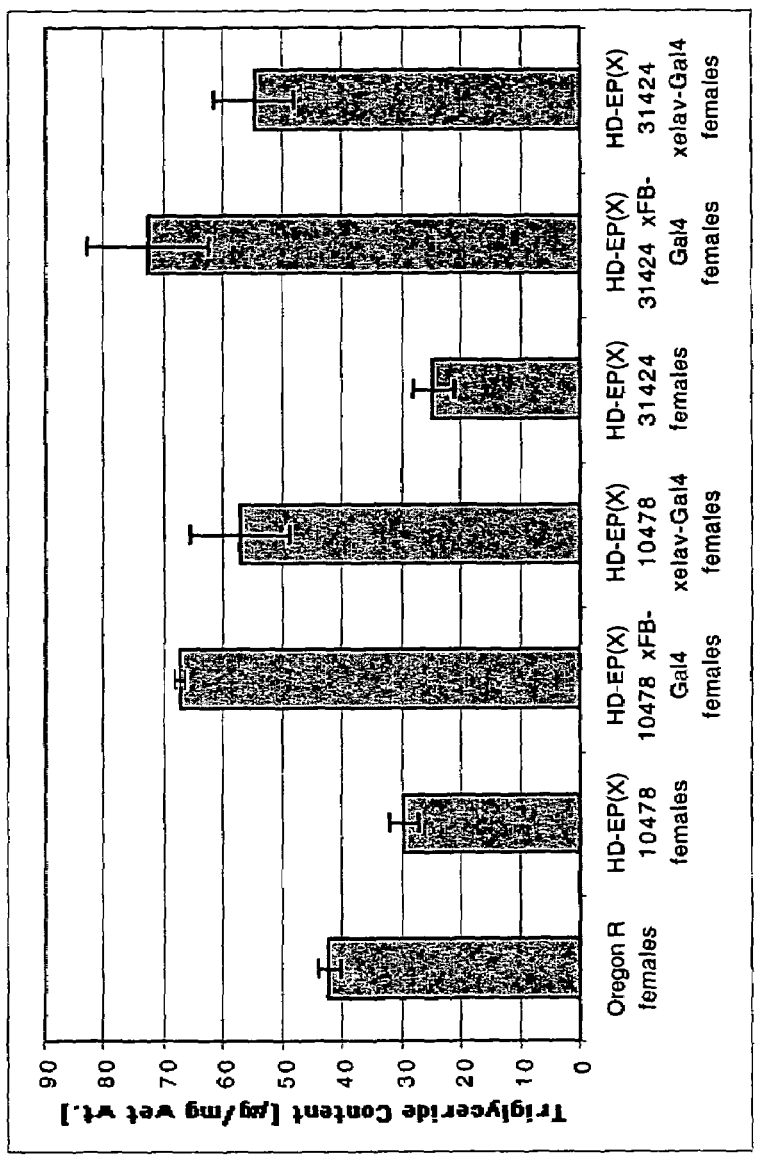

FIGURE 3: Molecular organisation of the *DevG20* locus
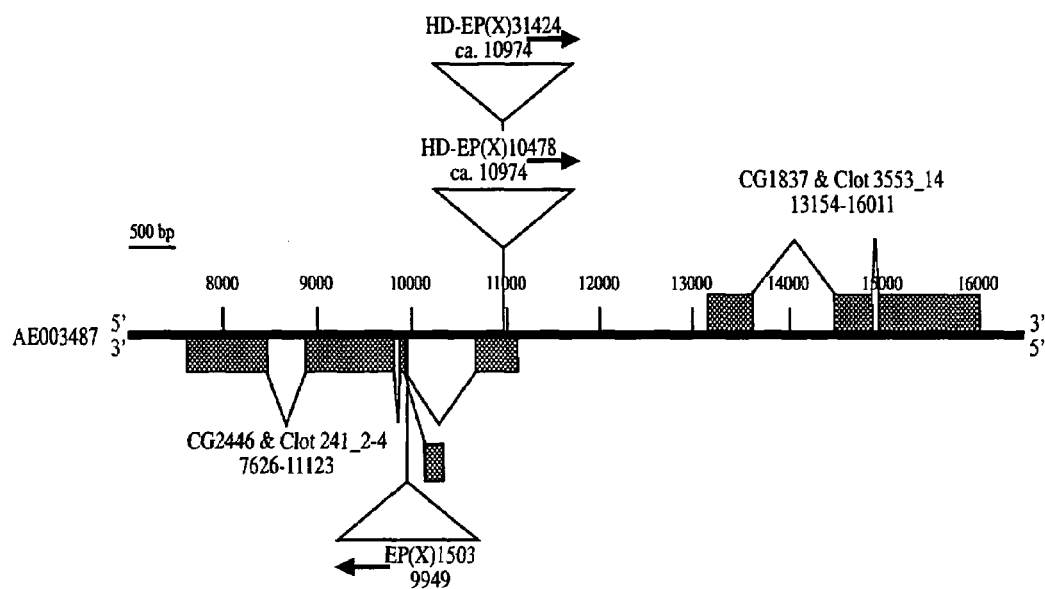

FIGURE 4A: Nucleotide sequence of the *DevG20* cDNA (SEQ ID NO:7)

```
CAACACTTTCAGATCTCTCCAAGCGTTCCGTGCATCATGTTGACCAGGTCCATTTTATCCGTTGCCGTGTGTGGCCTCCTCCTGTCG
CCCCTCCTGCCCATCACCCGTGCGTCCCAGGAGGAGGACACCGGCAAACAGGACAAGCAGTTCACCGTGGAACTGGACCCAGAAACC
TTCGACACTGCGATTGCCGGCGGCAATGTCTTCGTCAAGTTCTTTGCTCCATGGTGCGGCCATTGCAAGCGTATTCAGCCGCTGTGG
GAACAGCTGGCCGAGATCATGAATGTGGATAACCCCAAGGTGATCATCGCCAAGGTGGACTGCACCAAGCACCAGGGACTCTGCGCC
ACGCACCAGGTTACCGGCTATCCCACACTGCGCCTCTTTAAGCTGGGCGAAGAGGAATCGGTCAAGTTTAAGGGCACTCGCGACTTG
CCCGCCATTACCGATTTCATCAATAAGGAACTGAGCGCACCCGCTGAGGCGGATCTGGGCGAGGTCAAGCGCGAGCAGGTCGAGAAC
CTTAATATTGGCAAGGTGGTTGACCTTACCGAAGACACCTTTGCCAAGCACGTGTCCACCGGCAATCACTTTGTCAAATTCTTTGCA
CCCTGGTGCAGTCATTGTCAGCGTTTGGCACCCACGTGGGAGGACCTGGCCAAGGAGCTGATTAAAGAGCCTACCGTAACTATCTCG
AAGATCGACTGCACCCAGTTCCGTTCCATCTGCCAGGACTTTGAGGTCAAGGGGTATCCCACTCTTCTCTGGATCGAGGATGGCAAA
AAGATTGAAAAGTACTCGGGTGCTCGCGATCTGTCCACGCTGAAAACGTACGTGGAGAAAATGGTGGGCGTGCCACTGGAGAAGACC
GCTGGCGAGGCCGGCGATGAGAAGGTGGTTATCGAGGAGGTTGCCGGCGAGGAGGACGCAGCCAAGAAGCTGACTCCACAACAGCTG
ACTGGCGAGGACGAGTTCGACCAAGCCATTGCCGAGGGCGTTGCCTTCATTAAGTTCTATGCTCCGTGGTGTGGACACTGCCAGAAG
CTGCAACCCACCTGGGAGCAGCTGGCCACGGAAACGCACCAGGCTCAGAGTTCCGTGAAAATTGCCAAGGTTGACTGCACGGCGCCG
GAGAACAAGCAAGTGTGCATCGACCAGCAGGTGGAGGGCTATCCAACTCTCTTCCTTTACAAGAATGGTCAGCGCCAGAACGAGTAC
GAAGGCAGCCGCTCACTGCCGGAGCTGCAGGCCTATCTGAAGAAGTTCCTCGGCCACGACGAGCTCTAAAGCATCTGCCGGTTCACA
GGGAATCAGCAGTAGTCGAATGATCAAATAATCGCCCGCCAAATTAATTGTAATCGTAATTTTTCTTTCTCCAGCATAAACCTCTGT
GAGGAGTCCGCATTTAATCAATATATCCAACAACACCCAAACGACAACGCGCTAGCTGAAATTGATAAATTCAATCTGAGTTCCTTT
TACTTTTTTTCGTTTTTGTCCCTCTTCCTTAGCTGTTTTTGTAGAATTTTTTTTATACTTATTTGTTTAGTGTTTACGTAAATGGG
GCACGGGACTGTGTGCGCGATGATAAGCCATTTAGCGAACTTACATTTCAATTTTAAAGTCATTTTGAGTAGCCTACGTTTTAGGAA
AATTTGTCAACACAAAGCTAATAAATATCAATTGGAAAAC
```

FIGURE 4B: Amino acid sequence of *DevG20* protein (SEQ ID NO:8)

```
MLTRSILSVAVCGLLLSPLLPITRASQEEDTGKQDKQFTVELDPETFDTAIAGGNVFVKFFAPWCGHCKRIQPLWEQLAEIMNVDNP
KVIIAKVDCTKHQGLCATHQVTGYPTLRLFKLGEEESVKFKGTRDLPAITDFINKELSAPAEADLGEVKREQVENLNIGKVVDLTED
TFAKHVSTGNHFVKFFAPWCSHCQRLAPTWEDLAKELIKEPTVTISKIDCTQFRSICQDFEVKGYPTLLWIEDGKKIEKYSGARDLS
TLKTYVEKMVGVPLEKTAGEAGDEKVVIEEVAGEEDAAKKLTPQQLTGEDEFDQAIAEGVAFIKFYAPWCGHCQKLQPTWEQLATET
HQAQSSVKIAKVDCTAPENKQVCIDQQVEGYPTLFLYKNGQRQNEYEGSRSLPELQAYLKKFLGHDEL
```

FIGURE 4C: Nucleotide sequence of the human Dev20 homolog (SEQ ID NO:1)

```
GTCATGTTCT TCGCGCCCTG GTGTGGACAC TGCCAGCGGC TGCAGCCGAC TTGGAATGAC CTGGGAGACA
AATACAACAG CATGGAAGAT GCCAAAGTCT ATGTGGCTAA AGTGGACTGC ACGGCCCACT CCGACGTGTG
CTCCGCCCAG GGGGTGCGAG GATACCCCAC CTTAAAGCTT TTCAAGCCAG GCCAAGAAGC TGTGAAGTAC
CAGGGTCCTC GGGACTTCCA GACACTGGAA AACTGGATGC TGCAGACACT GAACGAGGAG CCAGTGACAC
CAGAGCCGGA AGTGGAACCG CCCAGTGCCC CCGAGCTCAA GCAAGGGCTG TATGAGCTCT CAGCAAGCAA
CTTTGAGCTG CACGTTGCAC AAGGCGACCA CTTTATCAAG TTCTTCGCTC CGTGGTGTGG TCACTGCAAA
GCCCTGGCTC CAACCTGGGA GCAGCTGGCT CTGGGCCTTG AACATTCCGA AACTGTCAAG ATTGGCAAGG
TTGATTGTAC ACAGCACTAT GAACTCTGCT CCGGAAACCA GGTTCGTGGC TATCCCACTC TTCTCTGGTT
CCGAGATGGG AAAAAGGTGG ATCAGTACAA GGGAAAGCGG GATTGGAGT CACTGAGGGA GTACGTGGAG
TCGCAGCTGC AGCGCACAGA GACTGGAGCG ACGGAGACCG TCACGCCCTC AGAGGCCCCG GTGCTGGCAG
CTGAGCCCGA GGCTGACAAG GGCACTGTGT TGGCACTCAC TGAAAATAAC TTCGATGACA CCATTGCAGA
AGGAATAACC TTCATCAAGT TTTATGCTCC ATGGTGTGGT CATTGTAAGA CTCTGGCTCC TACTTGGGAG
GAACTCTCTA AAAAGGAATT CCCTGGTCTG GCGGGGGTCA AGATCGCCGA AGTAGACTGC ACTGCTGAAC
GGAATATCTG CAGCAAGTAT TCGGTACGAG GCTACCCCAC GTTATTGCTT TTCCGAGGAG GGAAGAAAGT
CAGTGAGCAC AGTGGAGGCA GAGACCTTGA CTCGTTACAC CGCTTTGTCC TGAGCCAAGC GAAAGACGAA
CTTTAGGAAC ACAGTTGGAG GTCACCTCTC CTGCCCAGCT CCCGCACCCT GCGTTTAGGA GTTCAGTCCC
ACAGAGGCCA CTGGGTTCCC AGTGGTGGCT GTTCAGAAAG CAGAACATAC TAAGCGTGAG GTATCTTCTT
TGTGTGTGTG TTTTCCAAGC CAACACACTC TACAGATTCT TTATTAAATG TGTAACTCAT GGTCACTGTG
TAAACATTTT CAGTGGCGAT ATATCCCCTT TGACCTTCTC TTGATGAAAT TTACATGGTT TCCTTTGAGA
CTAAAATAGC GTTGAGGGAA ATGAAATTGC TGGACTATTT GTGGCTCCTG AGTTGAGTGA TTTTGGTGAA
AGAAAGCACA TCCAAAGCAT AGTTTACCTG CCCACGAGTT CTGGAAAGGT GGCCTTGTGG CAGTATTGAC
GTTCCTCTGA TCTTAAGGTC ACAGTTGACT CAATACTGTG TTGGTCCGTA GCATGGAGCA GATTGAAATG
CAAAAACCCA CACCTCTGGA AGATACCTTC ACGGCCGCTG CTGGAGCTTC TGTTGCTGTG AATACTTCTC
TCAGTGTGAG AGGTTAGCCG TGATGAAAGC AGCGTTACTT CTGACCGTGC CTGAGTAAGA GAATGCTGAT
GCCATAACTT TATGTGTCGA TACTTGTCAA ATCAGTTACT GTTCAGGGGA TCCTTCTGTT TCTCACGGGG
TGAAACATGT CTTTAGTTCC TCATGTTAAC ACGAAGCCAG AGCCCACATG AACTGTTGGA TGTCTTCCTT
AGAAAGGGTA GGCATGGAAA ATTCCACGAG GCTCATTCTC AGTATCTCAT TAACTCATTG AAAGATTCCA
```

```
GTTGTATTTG TCACCTGGGG TGACAAGACC AGACAGGCTT TCCCAGGCCT GGGTATCCAG GGAGGCTCTG
CAGCCCTGCT GAAGGGCCCT AACTAGAGTT CTAGAGTTTC TGATTCTGTT TCTCAGTAGT CCTTTTAGAG
GCTTGCTATA CTTGGTCTGC TTCAAGGAGG TCGACCTTCT AATGTATGAA GAATGGGATG CATTTGATCT
CAAGACCAAA GACAGATGTC AGTGGGCTGC TCTGGCCCTG GTGTGCACGG CTGTGGCAGC TGTTGATGCC
AGTGTCCTCT AACTCATGCT GTCCTTGTGA TTAAACACCT CTATCTCCCT TGGGAATAAG CACATACAGG
CTTAAGCTCT AAGATAGATA GGTGTTTGTC CTTTTACCAT CGAGCTACTT CCCATAATAA CCACTTTGCA
TCCAACACTC TTCACCCACC TCCCATACGC AAGGGGATGT GGATACTTGG CCCAAAGTAA CTGGTGGTAG
GAATCTTAGA AACAAGACCA CTTATACTGT CTGTCTGAGG CAGAAGATAA CAGCAGCATC TCGACCAGCC
TCTGCCTTAA AGGAAATCTT TATTAATCAC GTATGGTTCA CAGATAATTC TTTTTTTAAA AAAACCCAAC
CTCCTAGAGA AGCACAACTG TCAAGAGTCT TGTACACACA ACTTCAGCTT TGCATCACGA GTCTTGTATT
CCAAGAAAAT CAAAGTGGTA CAATTTGTTT GTTTACACTA TGATACTTTC TAAATAAACT CTTTTTTTTT
AAAAAAAAAA AAAAAAAAAA AAAAAAAAAA AAAAAAAAAA AAAAAAAAAA AC
```

FIGURE 4D: Amino acid sequence of the human Dev20 homolog (SEQ ID NO:2)

```
MEDAKVYVAK VDCTAHSDVC SAQGVRGYPT LKLFKPGQEA VKYQGPRDFQ TLENWMLQTL NEEPVTPEPE
VEPPSAPELK QGLYELSASN FELHVAQGDH FIKFFAPWCG HCKALAPTWE QLALGLEHSE TVKIGKVDCT
QHYELCSGNQ VRGYPTLLWF RDGKKVDQYK GKRDLESLRE YVESQLQRTE TGATETVTPS EAPVLAAEPE
ADKGTVLALT ENNFDDTIAE GITFIKFYAP WCGHCKTLAP TWEELSKKEF PGLAGVKIAE VDCTAERNIC
SKYSVRGYPT LLLFRGGKKV SEHSGGRDLD SLHRFVLSQA KDEL
```

FIGURE 5: Sequence alignment (BLASTP) of the DevG20 protein with the human homolog (hDevG20; SEQ ID NO:2)

```
Score = 267 bits (684), Expect = 2e-70
Identities = 146/325 (44%), Positives = 200/325 (60%), Gaps = 10/325 (3%)

DevG20:   84  VDNPKVIIAKVDCTKHQGLCATHQVTGYPTLRLFKLGEEESVKFKGTRDLPAITDFINKE  143
              +++ KV +AKVDCT H  +C+   V GYPTL+LFK G +E+VK++G RD    + +++ +
hDevG20:   1  MEDAKVYVAKVDCTAHSDVCSAQGVRGYPTLKLFKPG-QEAVKYQGPRDFQTLENWMLQT  59

DevG20:  144  LSAPAEADLGEVKREQVENLNIGKVVDLTEDTFAKHVSTGNHFVKFFAPWCSHCQRLAPT  203
              L+          EV+      L  G + +L+     F  HV+ G+HF+KFFAPWC HC+ LAPT
hDevG20:  60  LNEEPVTPEPEVEPPSAPELKQG-LYELSASNFELHVAQGDHFIKFFAPWCGHCKALAPT  118

DevG20:  204  WEDLAKELIKEPTVTISKIDCTQFRSICQDFEVKGYPTLLWIEDGKKIEKYSGARDLSTL  263
              WE LA  L     TV I K+DCTQ    +C   +V+GYPTLLW  DGKK+++Y G RDL +L
hDevG20: 119  WEQLALGLEHSETVKIGKVDCTQHYELCSGNQVRGYPTLLWFRDGKKVDQYKGKRDLESL  178

DevG20:  264  KTYVEKMVGVPLEKTAGEAGDEKVVIEE-VAGEEDAAKKLTPQQLTGEDEFDQAIAEGVA  322
              + YVE      L++T   A +     E V  E AKT    LT E+ FD  IAEG+
hDevG20: 179  REYVESQ----LQRTETGATETVTPSEAPVLAAEPEADKGTVLALT-ENNFDDTIAEGIT  233

DevG20:  323  FIKFYAPWCGHCQKLQPTWEQLATETHQAQSSVKIAKVDCTAPENKQVCIDQQVEGYPTL  382
              FIKFYAPWCGHC+ L PTWE+L+ +    + VKIA+VDCTA  N  +C   V GYPTL
hDevG20: 234  FIKFYAPWCGHCKTLAPTWEELSKKEFPGLAGVKIAEVDCTAERN--ICSKYSVRGYPTL  291

DevG20:  383  FLYKNGQRQNEYEGSRSLPELQAYL  407
              L++ G++  +E+ G R L  L  ++
hDevG20: 292  LLFRGGKKVSEHSGGRDLDSLHRFV  316
```

FIGURE 6: Expression of DevG20 in mammalian tissues
(A) Real-time PCR analysis of DevG20 expression in wildtype mouse tissues
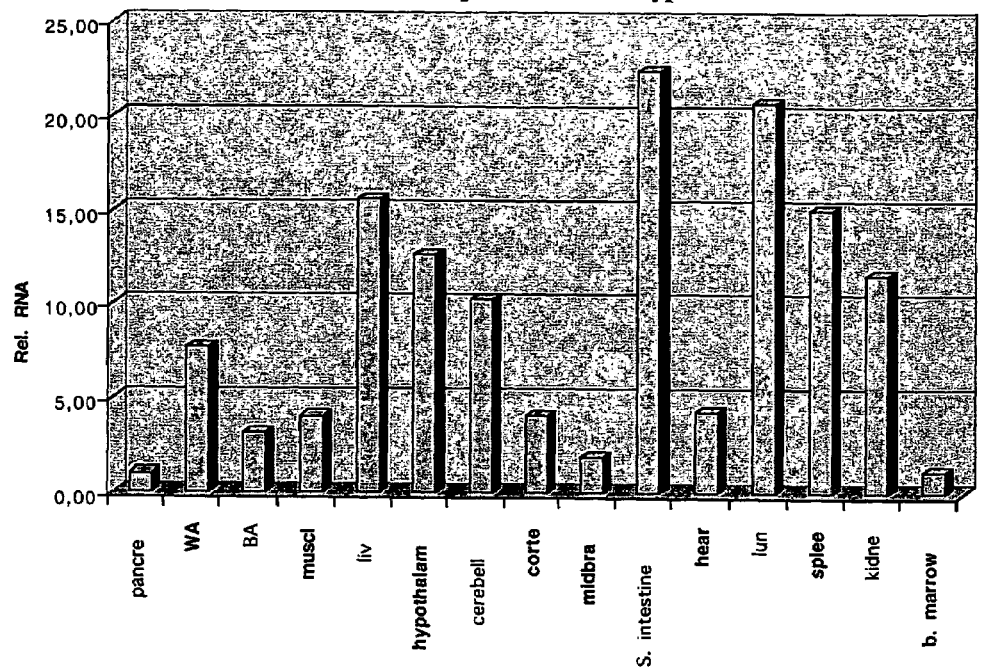
(B) Real-time PCR mediated comparison of DevG20 expression in different mouse models
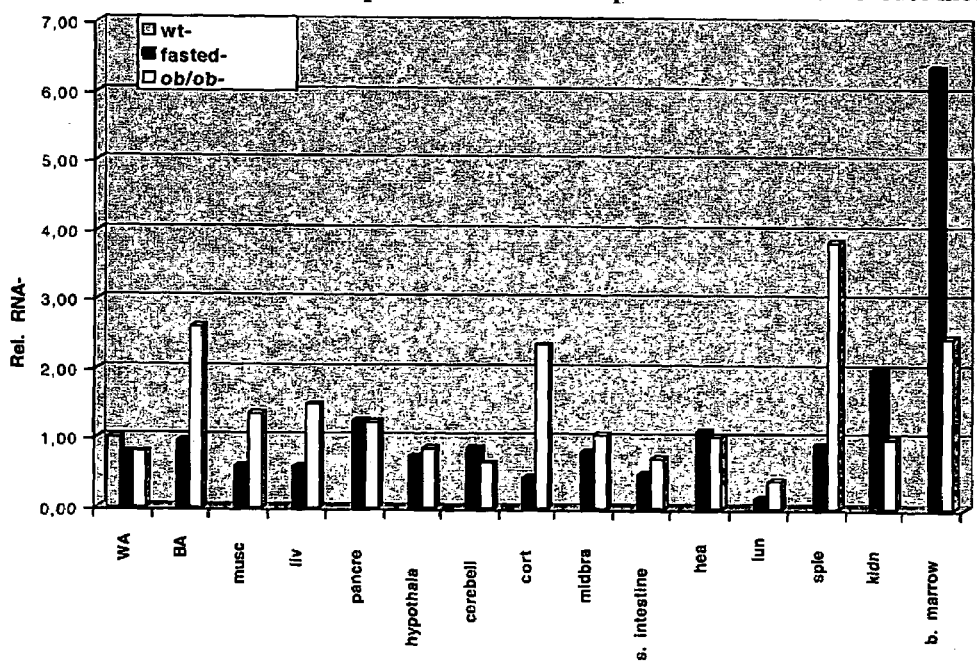

(C) Real-time PCR mediated comparison of DevG20 expression during the differentiation of 3T3-L1 cells from pre-adipocytes to mature adipocytes
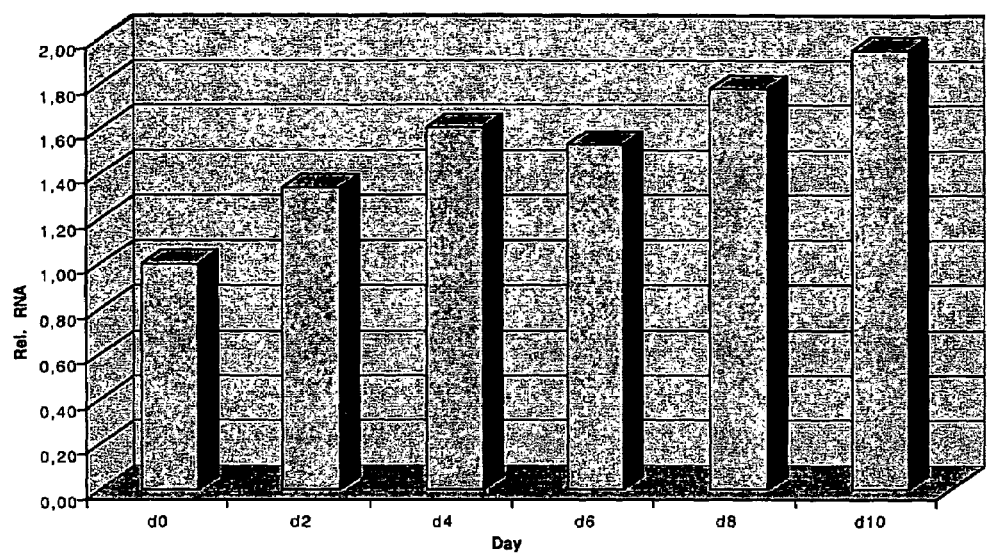

FIGURE 7: Increase of triglyceride content of homozygous flies
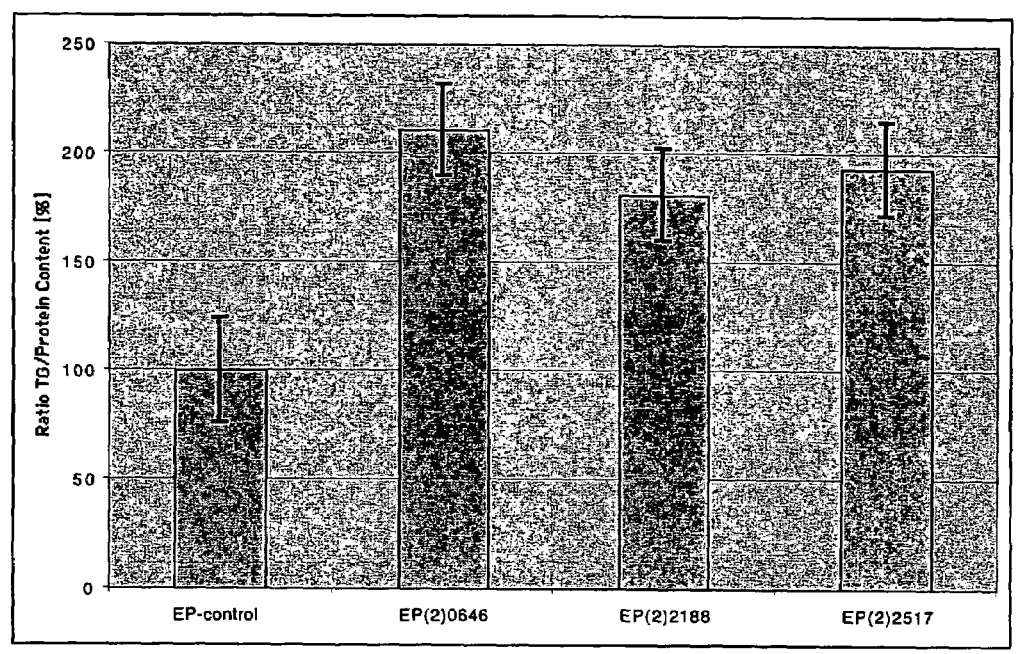

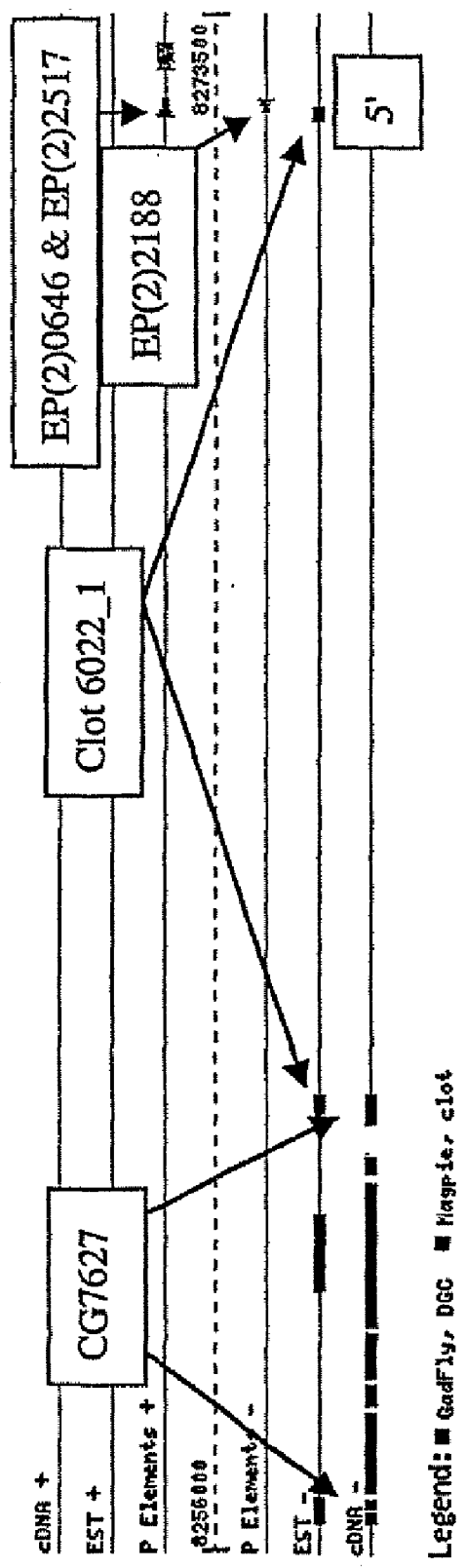
FIGURE 8: Molecular organisation of the *DevG4* locus

**FIGURE 9A: Nucleotide sequence of the *DevG4* cDNA (SEQ ID NO:9)**

```
GACCGAAGTT TGTTTTATTA TTTACAATAT CTGTATATAG TTTTTGTGTT GCTTTGCCGG GTCTTCTATC
GCGATTTTCT CACGTTCGCC AGCAACAATA ACCATATTGT TGAATGTAAA CAATATTGAA ACAAAATTTC
TTTAGAGGCA GTAGAACATG CAGTCGCTGA AAACGGCAGA TTTGCCGGAA AATCCCCGGG AACATTGCAA
TTTTATTTCG GCAGCATGTT TTTGGTACAC CATGCCGACT TTTATCAAGG GTCGGAAACG CACATTGGAT
ACCAAGGATC TTTACAGAGC CTTAAAAGAG CACAAATCTG AGACTCTGGG GAACAAATTG TGCGCTTCCT
GGGAATTGGA ACTTGAGAAG ACCAAAGGAA AGCCCAATTT GTTGAGAGCC CTTCTGCGAG TTTTTGGCTG
GTACTTCGCA CTGCTTGGCC TGGTGCTTTT CCTGCTGGAA TTGGGTCTTC GAACGCTTCA GCCAATCTTC
CTGCTGAAAC TCATCGCCTA CTACACACAT GGCTCGGAAT CGATTGAATC GGCCTATTAC TATGCAGCTG
GAGTGATCCT GTGCAGTGCC CTCAATGTCA TTATAATGCA TCCCTATATG CTAGGCACAA TGCATGTGGG
ACTCAAGATG CGCGTTGGTA TGTGCAGCAT GATCTACCGC AAGGCGTTAC GGCTGAGTAA GTCGGCGTTG
GGAGACACCA CAGCTGGACA TGTGGTGAAT CTTATGTCCA ACGACGTGGG ACGTCTCGAT CTGGCTACCA
TATTCGTACA CTACTTGTGG GTGGGACCGC TGGAGACCCT CTTTATCACA TACCTAATGT ACCGTGAGAT
TGGAATCGCT GCTGTGTTTG GTGTGGCCTT CATGTTGCTG TTCATCCCCC TGCAGGCGTA TCTGGGAAAA
AGAACATCGG TGTTGCGACT CAGAACCGCC TTACGCACGG ATGAAAGGGT ACGGATGATG AACGAAATCA
TCTCGGGCAT TCAGGTGATT AAAATGTACG CATGGGAATT GCCATTCGAA CATATGGTGC CCTTTGCCCG
TAAGAGGAG ATAAATGCCA TCCGCCATGT GTCCTACATC CGTGGAATTC TGCTCTCCTT CATCATCTTT
CTGACGCGTG TCTCAATTTT CCTGAGTCTG GTGGGATATG TTCTGCTCGG GACGTTCCTA ACCCCGGAAG
TGGCGTTCTT GATCACAGCC TACTACAATA TCCTGCGTAC CACTATGACG GTGTTCTTTC CCCAGGGCAT
TTCCCAAATG GCGGAGACCC TGGTGTCCAT TAAGCGTGTC CAGAAGTATA TGCAGTCCGA CGAGACGAAT
GTGATGGATA TGAGTGTGGA TCTTACCGAG GATTTCCAAG GAAGCAATCA GGAAACGGTT CATGCCGATG
GAGATGAGGA GCGCGACGAA GCTGAGGATA AGCTTTTAGG TCCACCAATT GCCACTGTTA ATGAGAACGC
CAAGTTGTCG GAGGCGGAA TCTCTATTAG CGGACTTATG GCCAAATGGG ATGTTAACTC CCCCGATTAC
TCGCTTAATG GTGTAAACCT TCGTGTTCAG CCTGGAACCA TGCTGGGTAT TGTCGGACGC ACTGGATCCG
GTAAATCCAG TCTCATCCAA GCCATCCTTG GTGAACTGCC CGCAGAGTCT GGCGAGATAA AGGTTAATGG
CTCCATGTCG TATGCTTCCC AAGAACCGTG GCTCTTTTCC GGCACCTGGC GACAAAATAT TCTCTTTGGC
CAGCCTATGG ATCGTCGTCG TTACGCTAAG GTGGTGAAGA AATGTGCCCT GGAGCGAGAT TTCGAGCTGC
TCCCGTTTAA GGATAAAACC ATAGTTGGAG AGCGTGGAGC TTCCCTGTCG GGTGGCCAAA AGGCGAGAAT
CAGTTTGCA AGAGCTGTTT ATCGGGAGAC CTCCATATAC CTGCTGGATG ATCCTCTGAG TGCCGTGGAC
ACCCATGTGG CCCGCCATCT GTTCGAGCAG TGCATGCGTG GCTATCTACG CGAGCGAATT GTTATATTGG
CCACTCATCA GCTCCAGTTT TTGCAGCACG CCGATCAGAT TGTCATCATG GATAAGGGTC GTGTAAGCGC
CGTGGGCACC TACGAGTCTC TACGCGAATC CGGGTTGGAC TTCGCCTCCA TGCTAGCCGA TCCAGAGCGG
GATGAGCAAT CAGAGGAGCG ATCACGGTCG CGATCGGGCA GCTACACCCA CAGTCATTCG GACCAGCGAC
GCAACAGCGA GCAATCCCTA CTTTCCATGG CAGATTCGTG CATGGATGAC CTCGAAGCGG AGCAAGCTAA
CAACCAGGAA CGCCAGGAGG CTGGTCAAAT CGGCCTGCGC TTGTACAGCA AATACTTCAA AGCGGGAGGC
GGTTTCTTCG CCTTCTTCGT GATGATGGGC TTCTGTGTGC TCTCGCAAGG ATTGGCCTCT CTGGGTGACT
ATTTTCTCTC ATATTGGGTT ACCAAAAAGG GAAATGTGGC TTACCGTGCA GATAATAATG ACACAACTCG
CTCTGAGGAA CTCGAACCTC GTCTGTCGAC ATGGCTTCGT GATATAGGAT TGTCCGTGGA TGCTGAAATG
CTGGATACTT ATATATTCAC GGTGATCACA GTACTGACCA TCCTGGTGAC CGTGGCTCGC TCGTTTTTAT
TCTTTAATTT GGCCATGAAA GCCTCAATTC GTTGCACAA TTCCATGTTC CGCGGCATCA CCCGAGCTGC
CATGTACTTC TTCAATACGA ATCCATCTGG GCGCATTCTA AACCGTTTCT CAAAGGATAT GGGACAAGTT
GACGAGATAC TGCCTGCCGT GATGATGGAT GTCATCCAGA TTTTCCTTGC ACTTGCTGGC ATTGTGATCG
TCATAGCCGT TGTCAATCCG CTGTTCCTTA TTCCAACCGT AGTACTGGAG ATTATTTTCT ATCAACTGCG
CACCTTTTAT CTAAAGACAT CAAGGGATGT AAAGCGCATG GAAGCAATTA CTCGGTCTCC AGTATACTCG
CATTTAGCTG CCTCGTTGAC CGGTCTGTCC ACCATTCGTG CCTTTGGAGC CCAACGTGTT CTGGAGGCGG
AGTTCGACAA TTACCAGGAT ATGCATAGCT CCGCATTTTA TATGTTCATT AGCACCTCGC GAGCCTTCGG
ATATTGGCTT GACTGTTTCT GTGTGATTTA CATAGCCATA ATTACTCTCA GTTTCTTCAT CTTTCCTCCT
GCGAACGGAG GCGATGTGGG ACTGGCCATT ACGCAGGCAA TGGGAATGAC CGGCATGGTT CAGTGGGGAA
TGCGTCAGTC AGCCGAGCTG GAGAATACGA TGACAGCTGT GGAGCGAGTG GTTGAGTACG AGGACATTGA
ACCGAAGGA GCGTTGGAAG CTCCGGCCGA TAAGAAGCCA CCAAAGTCAT GGCCAGAGCA GGGAAAAATC
GTTTTCGACG AGCTTAGCTT GCGCTATACG CCCGGATCCA AGTCGGAGAA TGTGCTCAAG TCACTTAGTT
TCGTAATAAA ACCTAAGGAG AAAGTAGGCA TCGTGGGACG CACTGGAGCG GGAAAGTCTT CGCTGATTAA
TGCCCTGTTC CGACTGTCCT ACAACGATGG ATCTGTGCTC ATAGACAAGA GGGATACCAG TGAGATGGGT
TTGCATGACC TGCGCAGCAA AATCTCGATC ATACCGCAGG AACCCGTTCT GTTTCCGGC ACTATGCGAT
ACAACTTGGA TCCCTTCGAC GAGTATAGCG ATGATAAGCT GTGGCGCTCC CTGGAGGAGG TAAAGCTAAA
GGAGGTGGTT GCTGATCTTC CCAGTGGCTT GCAGACAAA ATCACCGAGG GCGGAACCA CTTCAGCGTT
GGCCAGCGCC AGTTGGTCTG CTTGGCACGG GCTATACTGC GTGAAAATCG TATCCTGGTA ATGGACGAGG
CTACGGCCAA TGTGGATCCC CAGACAGATG GCCTCATCCA AACCACCATA CGAAACAAGT TCAAGGAGTG
CACTGTGCTG ACGATAGCTC ATCGTTTGCA CACCATCATG GACTCGGACA AAGTCTTGGT GATGGACGCT
GGTCGAGCGG TGGAGTTTGG AACGCCCTAT GAACTGCTGA CGCTGGCGGA TTCTAAGGTG TTCCACGGTA
TGGTGAAGCA AACGGGTCAC GCCACCTATG AGAGTCTGCT GAAAATCGCC CAAAAGGCAT TCGAAAACAG
GCAGAATCAC AGTCTTTCCT CGTGAGAATC AGCTATTATG TGTTTGTCAC CGAATCTTTA GCTGGCTAAT
CATAGTTTAA GTAATCATAA TGTTTTTGAA TGTGTTATTT TGTGTGAATG TATATATGTT TTTCCGTGTG
TGTGTGTTAA AAACTTTATA TATGTAACTT AAAAACTGTA TAGGAAACCT TTGTTTAATC TACTATTTGT
ATTTATTAAA CATTCACTAA GAGCAAAGAT GTGCCTTAAA AAATAAATGA AATATTTTCT CTGTTCCTAA
```

FIGURE 9B: Amino acid sequence of DevG4 (SEQ ID NO:10)

```
MQSLKTADLF ENPREHCNFI SAACFWYTMP TFIKGRKRTL DTKDLYRALK EHKSETLGNK LCASWELELE
KTKGKPNLLR ALLRVFGWYF ALLGLVLFLL ELGLRTLQPI FLLKLIAYYT HGSESIESAY YYAAGVILCS
ALNVIIMHPY MLGTMHVGLK MRVGMCSMIY RKALRLSKSA LGDTTAGHVV NLMSNDVGRL DLATIFVHYL
WVGPLETLFI TYLMYREIGI AAVFGVAFML LFIPLQAYLG KRTSVLRLRT ALRTDERVRM MNEIISGIQV
IKMYAWELPF EHMVAFARKK EINAIRHVSY IRGILLSFII FLTRVSIFLS LVGYVLLGTF LTPEVAFLIT
AYYNILRTTM TVFFPQGISQ MAETLVSIKR VQKYMQSDET NVMDMSVDLT EDFQGSNQET VHADGDEERD
EAEDKLLGPP IATVNENAKL SEAGISISGL MAKWDVNSPD YSLNGVNLRV QPGTMLGIVG RTGSGKSSLI
QAILGELPAE SGEIKVNGSM SYASQEPWLF SGTVRQNILF GQPMDRRRYA KVVKKCALER DFELLPFKDK
TIVGERGASL SGGQKARISL ARAVYRETSI YLLDDPLSAV DTHVARHLFE QCMRGYLRER IVILATHQLQ
FLQHADQIVI MDKGRVSAVG TYESLRESGL DFASMLADPE RDEQSEERSR SRSGSYTHSH SDQRRNSEQS
LLSMADSCMD DLEAEQANNQ ERQEAGQIGL RLYSKYFKAG GGFFAFFVMM GFCVLSQGLA SLGDYFLSYW
VTKKGNVAYR ADNNDTTRSE ELEPRLSTWL RDIGLSVDAE MLDTYIFTVI TVLTILVTVA RSFLFFNLAM
KASIRLHNSM FRGITRAAMY FFNTNPSGRI LNRFSKDMGQ VDEILPAVMM DVIQIFLALA GIVIVIAVVN
PLFLIPTVVL GIIFYQLRTF YLKTSRDVKR MEAITRSPVY SHLAASLTGL STIRAFGAQR VLEAEFDNYQ
DMHSSAFYMF ISTSRAFGYW LDCFCVIYIA IITLSFFIFP PANGGDVGLA ITQAMGMTGM VQWGMRQSAE
LENTMTAVER VVEYEDIEPE GALEAPADKK PPKSWPEQGK IVFDELSLRY TPDPKSENVL KSLSFVIKPK
EKVGIVGRTG AGKSSLINAL FRLSYNDGSV LIDKRDTSEM GLHDLRSKIS IIPQEPVLFS GTMRYNLDPF
DEYSDDKLWR SLEEVKLKEV VADLPSGLQS KITEGGTNFS VGQRQLVCLA RAILRENRIL VMDEATANVD
PQTDGLIQTT IRNKFKECTV LTIAHRLHTI MDSDKVLVMD AGRAVEFGTP YELLTLADSK VFHGMVKQTG
HATYESLLKI AQKAFENRQN HSLSS
```

FIGURE 9C: Nucleotide sequence of the human DevG4 homolog (SEQ ID NO:3)

```
GGACAGGCGT GGCGGCCGGA GCCCCAGCAT CCCTGCTTGA GGTCCAGGAG CGGAGCCCGC GGCCACCGCC
GCCTGATCAG CGCGACCCCG GCCCGCGCCC GCCCCGCCCG GCAAGATGCT GCCCGTGTAC CAGGAGGTGA
AGCCCAACCC GCTGCAGGAC GCGAACATCT GCTCACGCGT GTTCTTCTGG TGGCTCAATC CCTTGTTTAA
AATTGGCCAT AAACGGAGAT TAGAGGAAGA TGATATGTAT TCAGTGCTGC CAGAAGACCG CTCACAGCAC
CTTGGAGAGG AGTTGCAAGG GTTCTGGGAT AAAGAAGTTT TAAGAGCTGA GAATGACGCA CAGAAGCCTT
CTTTAACAAG AGCAATCATA AAGTGTTACT GGAAATCTTA TTTAGTTTTG GGAATTTTTA CGTTAATTGA
GGAAAGTGCC AAAGTAATCC AGCCCATATT TTTGGGAAAA ATTATTAATT ATTTTGAAAA TTATGATCCC
ATGGATTCTG TGGCTTTGAA CACAGCGTAC GCCTATGCCA CGGTGCTGAC TTTTTGCACG CTCATTTTGG
CTATACTGCA TCACTTATAT TTTTATCACG TTCAGTGTGC TGGGATGAGG TTACGAGTAG CCATGTGCCA
TATGATTTAT CGGAAGGCAC TTCGTCTTAG TAACATGGCC ATGGGGAAGA CAACCACAGG CCAGATAGTC
AATCTGCTGT CCAATGATGT GAACAAGTTT GATCAGGTGA CAGTGTTCTT ACACTTCCTG TGGGCAGGAC
CACTGCAGGC GATCGCAGTG ACTGCCCTAC TCTGGATGGA GATAGGAATA TCGTGCCTTG CTGGGATGGC
AGTTCTAATC ATTCTGCTGC CCTTGCAAAG CTGTTTTGGG AAGTTGTTCT CATCACTGAG GAGTAAAACT
GCAACTTTCA CGGATGCCAG GATCAGGACC ATGAATGAAG TTATAACTGG TATAAGGATA ATAAAAATGT
ACGCCTGGGA AAAGTCATTT TCAAATCTTA TTACCAATTT GAGAAAGAAG GAGATTTCCA AGATTCTGAG
AAGTTCCTGC CTCAGGGCGA TGAATTTGGC TTCGTTTTTC AGTGCAAGCA AAATCATCGT GTTTGTGACC
TTCACCACCT ACGTGCTCCT CGGCAGTGTG ATCACCAGCCA GCCGCGTGTT CGTGCGCAGTG ACGCTGTATG
GGGCTGTGCG GCTGACGGTT ACCCTCTTCT TCCCCTCAGC CATTGAGAGG GTGTCAGAGG CAATCGTCAG
CATCCGAAGA ATCCAGACCT TTTTGCTACT TGATGAGATA TCACAGCGCA ACCGTCAGCT GCCGTCAGAT
GGTAAAAAGA TGGTGCATGT GCAGGATTTT ACTGCTTTTT GGGATAAGGC ATCAGAGACC CCAACTCTAC
AAGGCCTTTC CTTTACTGTC AGACCTGGCG AATTGTTAGC TGTGGTCGGC CCCGTGGGAG CAGGGAAGTC
ATCACTGTTA AGTGCCGTGC TCGGGGAATT GGCCCCAAGT CACGGGCTGG TCAGCGTGCA TGGAAGAATT
GCCTATGTGT CTCAGCAGCC CTGGGTGTTC TCGGGAACTC TGAGGAGTAA TATTTTATTT GGGAAGAAAT
ATGAAAAGGA ACGATATGAA AAAGTCATAA AGGCTTGTGC TCTGAAAAAG GATTTACAGC TGTTGGAGGA
TGGTGATCTG ACTGTGATAG GAGATCGGGG AACCACGCTG AGTGGAGGGC AGAAAGCACG GGTAAACCTT
GCAAGAGCAG TGTATCAAGA TGCTGACATC TATCTCCTGG ACGATCCTCT CAGTGCAGTA GATGCGGAAG
TTAGCAGACA CTTGTTCGAA CTGTGTATTT GTCAAATTTT GCATGAGAAG ATCACAATTT TAGTGACTCA
TCAGTTGCAG TACCTCAAAG CTGCAAGTCA GATTCTGATA TTGAAAGATG GTAAAATGGT GCAGAAGGGG
ACTTACACTG AGTTCCTAAA ATCTGGTATA GATTTTGGCT CCCTTTTAAA GAAGGATAAT GAGGAAAGTG
AACAACCTCC AGTTCCAGGA ACTCCCACAC TAAGGAATCG TACCTTCTCA GAGTCTTCGG TTTGGTCTCA
ACAATCTTCT AGACCCTCCT TGAAAGATGG TGCTCTGGAG AGCCAAGATA CAGAGAATGT CCCAGTTACA
CTATCAGAGG AGAACCGTTC TGAAGGAAAA GTTGGTTTTC AGGCCTATAA GAATTACTTC AGAGCTGGTG
CTCACTGGAT TGTCTTCATT TTCCTTATTC TCCTAAACAC TGCAGCTCAG GTTGCCTATG TGCTTCAAGA
TTGGTGGCTT TCATACTGGG CAAACAAACA AAGTATGCTA AATGTCACTG TAAATGGAGG AGGAAATGTA
ACCGAGAAGC TAGATCTTAA CTGGTACTTA GGAATTTATT CAGGTTTAAC TGTAGCTACC GTTCTTTTTG
```

FIGURE 9C (Continued)

```
GCATAGCAAG ATCTCTATTG GTATTCTACG TCCTTGTTAA CTCTTCACAA ACTTTGCACA ACAAAATGTT
TGAGTCAATT CTGAAAGCTC CGGTATTATT CTTTGATAGA AATCCAATAG GAAGAATTTT AAATCGTTTC
TCCAAAGACA TTGGACACTT GGATGATTTG CTGCCGCTGA CGTTTTTAGA TTTCATCCAG ACATTGCTAC
AAGTGGTTGG TGTGGTCTCT GTGGCTGTGG CCGTGATTCC TTGGATCGCA ATACCCTTGG TTCCCCTTGG
AATCATTTTC ATTTTTCTTC GGCGATATTT TTTGGAAACG TCAAGAGATG TGAAGCGCCT GGAATCTACA
ACTCGGAGTC CAGTGTTTTC CCACTTGTCA TCTTCTCTCC AGGGGCTCTG GACCATCCGG GCATACAAAG
CAGAAGAGAG GTGTCAGGAA CTGTTTGATG CACACCAGGA TTTACATTCA GAGGCTTGGT TCTTGTTTTT
GACAACGTCC CGCTGGTTCG CCGTCCGTCT GGATGCCATC TGTGCCATGT TTGTCATCAT CGTTGCCTTT
GGGTCCCTGA TTCTGGCAAA AACTCTGGAT GCCGGGCAGG TTGGTTTGGC ACTGTCCTAT GCCCTCACGC
TCATGGGGAT GTTTCAGTGG TGTGTTCGAC AAAGTGCTGA AGTTGAGAAT ATGATGATCT CAGTAGAAAG
GGTCATTGAA TACACAGACC TTGAAAAAGA AGCACCTTGG GAATATCAGA AACGCCCACC ACCAGCCTGG
CCCCATGAAG GAGTGATAAT CTTTGACAAT GTGAACTTCA TGTACAGTCC AGGTGGGCCT CTGGTACTGA
AGCATCGAC AGCACTCATT AAATCACAAG AAAAGGTTGG CATTGTGGGA AGAACCGGAG CTGGAAAAAG
TTCCCTCATC TCAGCCCTTT TTAGATTGTC AGAACCCGAA GGTAAAATTT GGATTGATAA GATCTTGACA
ACTGAAATTG GACTTCACGA TTTAAGGAAG AAAATGTCAA TCATACCTCA GGAACCTGTT TTGTTCACTG
GAACAATGAG GAAAACCTG GATCCCTTTA AGGAGCACAC GGATGAGGAA CTGTGGAATG CCTTACAAGA
GGTACAACTT AAAGAAACCA TTGAAGATCT TCCTGGTAAA ATGGATACTG AATTAGCAGA ATCAGGATCC
AATTTTAGTG TTGGACAAAG ACAACTGGTG TGCCTTGCCA GGGCAATTCT CAGGAAAAAT CAGATATTGA
TTATTGATGA AGCGACGGCA AATGTGGATC CAAGAACTGA TGAGTTAATA CAAAAAAAAA TCCGGGAGAA
ATTTGCCCAC TGCACCGTGC TAACCATTGC ACACAGATTG AACACCATTA TTGACAGCGA CAAGATAATG
GTTTTAGATT CAGGAAGACT GAAAGAATAT GATGAGCCGT ATGTTTTGCT GCAAAATAAA GAGAGCCTAT
TTTACAAGAT GGTGCAACAA CTGGGCAAGG CAGAAGCCGC TGCCCTCACT GAAACAGCAA AACAGGTATA
CTTCAAAAGA AATTATCCAC ATATTGGTCA CACTGACCAC ATGGTTACAA ACACTTCAA TGGACAGCCC
TCGACCTTAA CTATTTTCGA GACAGCACTG TGAATCCAAC CAAAATGTCA AGTCCGTTCC GAAGGCATTT
TCCACTAGTT TTTGGACTAT GTAAACCACA TTGTACTTTT TTTTACTTTG GCAACAAATA TTTATACATA
CAAGATGCTA GTTCATTTGA ATATTTCTCC C
```

FIGURE 9D: Amino acid sequence of the human DevG4 homolog (SEQ ID NO:4)

```
MLPVYQEVKP NPLQDANICS RVFFWWLNPL FKIGHKRRLE EDDMYSVLPE DRSQHLGEEL QGFWDKEVLR
AENDAQKPSL TRAIIKCYWK SYLVLGIFTL IEESAKVIQP IFLGKIINYF ENYDPMDSVA LNTAYAYATV
LTFCTLILAI LHHLYFYHVQ CAGMRLRVAM CHMIYRKALR LSNMAMGKTT TGQIVNLLSN DVNKFDQVTV
FLHFLWAGPL QAIAVTALLW MEIGISCLAG MAVLIILLPL QSCFGKLFSS LRSKTATFTD ARIRTMNEVI
TGIRIIKMYA WEKSFSNLIT NLRKKEISKI LRSSCLRGMN LASFFSASKI IVFVTFTTYV LLGSVITASR
VFVAVTLYGA VRLTVTLFFP SAIERVSEAI VSIRRIQTFL LLDEISQRNR QLPSDGKKMV HVQDFTAFWD
KASETPTLQG LSFTVRPGEL LAVVGPVGAG KSSLLSAVLG ELAPSHGLVS VHGRIAYVSQ QPWVFSGTLR
SNILFGKKYE KERYEKVIKA CALKKDLQLL EDGDLTVIGD RGTTLSGGQK ARVNLARAVY QDADIYLLDD
PLSAVDAEVS RHLFELCICQ ILHEKITILV THQLQYLKAA SQILILKDGK MVQKGTYTEF LKSGIDFGSL
LKKDNEESEQ PPVPGTPTLR NRTFSESSVW SQQSSRPSLK DGALESQDTE NVPVTLSEEN RSEGKVGFQA
YKNYFRAGAH WIVFIFLILL NTAAQVAYVL QDWWLSYWAN KQSMLNVTVN GGGNVTEKLD LNWYLGIYSG
LTVATVLFGI ARSLLVFYVL VNSSQTLHNK MFESILKAPV LFFDRNPIGR ILNRFSKDIG HLDDLLPLTF
LDFIQTLLQV VGVVSVAVAV IPWIAIPLVP LGIIFIFLRR YFLETSRDVK RLESTTRSPV FSHLSSSLQG
LWTIRAYKAE ERCQELFDAH QDLHSEAWFL FLTTSRWFAV RLDAICAMFV IIVAFGSLIL AKTLDAGQVG
LALSYALTLM GMFQWCVRQS AEVENMMISV ERVIEYTDLE KEAPWEYQKR PPPAWPHEGV IIFDNVNFMY
SPGGPLVLKH LTALIKSQEK VGIVGRTGAG KSSLISALFR LSEPEGKIWI DKILTTEIGL HDLRKKMSII
PQEPVLFTGT MRKNLDPFKE HTDEELWNAL QEVQLKETIE DLPGKMDTEL AESGSNFSVG QRQLVCLARA
ILRKNQILII DEATANVDPR TDELIQKKIR EKFAHCTVLT IAHRLNTIID SDKIMVLDSG RLKEYDEPYV
LLQNKESLFY KMVQQLGKAE AAALTETAKQ VYFKRNYPHI GHTDHMVTNT SNGQPSTLTI FETAL
```

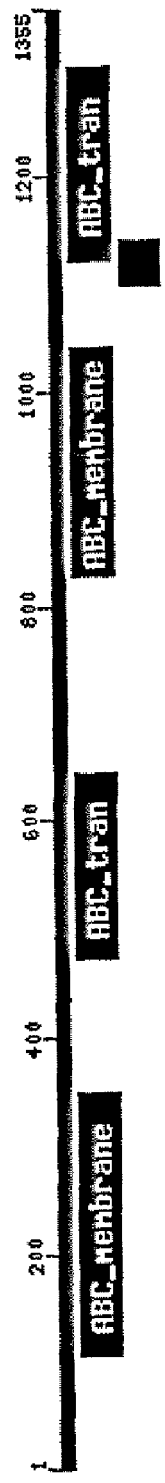
FIGURE 10: Protein domains of the DevG4 protein

FIGURE 11: Comparison of human MRP4, mouse MRP4 (partial), and Drosophila DevG4 protein domains (A)     CLUSTAL X (1.8) multiple sequence alignment of ABC-membrane I

```
hMRP4      YLVLG--IFTLIEESAKVIQPIFLGKIINYFENYDPMDSVALNTAYAYATVLTFCTLILA
DevG4      YFALLGLVLFLLELGLRTLQPIFLLKLIAYYT----HGSESIESAYYYAAGVILCSALNV hMRP4      ILHHLYFYHVQCAGMRLRVAMCHMIYRKALRLSNMAMGKTTTGQIVNLLSNDVNKFDQVT
DevG4      IIMHPYMLGTMHVGLKMRVGMCSMIYRKALRLSKSALGDTTAGHVVNLMSNDVGRLDLAT hMRP4      VFLHFLWAGPLQAIAVTALLWMEIGISCLAGMAVLIILLPLQSCFGKLFSSLRSKTATFT
DevG4      IFVHYLWVGPLETLFITYLMYREIGIAAVFGVAFMLLFIPLQAYLGKRTSVLRLRTALRT hMRP4      DARJRTMNEVITGIRIIKMYAWEKSFSNLITNLRKKEISKILRFSCLRGMNLASFFSASK
DevG4      DERVRMMNEIISGIQVIKMYAWELPFEHMVAFARKKEINAIRHVSYIRGILLSFIIFLTR hMRP4      IIVFVTFTTYVLLGSVITASRVFVAVTLYGAVRLTV
DevG4      VSIFLSLVGYVLLGTFLTPEVAFLITAYYNILRTTM
```

(B)     CLUSTAL X (1.8) multiple sequence alignment of ABC-tran I

```
hMRP4      GELLAVVGPVCAGKSSLLSAVLGELAPSHGLVSVHGRIAYVSQQPWVFSGTLRSNILFGK
DevG4      GTMLGIVGRTCSGKSSLIQAILGELPAESGEIKVNGSMSYASQEPWLFSGTVRQNILFGQ hMRP4      KYEKERYEKVIKACALKKDLQLLEDGDLTVIGDRGTTLSGGQKARVNLARAVYQDADIYL
DevG4      PMDRRRYAKVVKKCALERDFELLPFKDKTIVGERGASLSGGQKARISLARAVYRETSIYL hMRP4      LDDPLSAVDAEVSRHLFELCICQILHEKITILVTHQLQYLKAASQILILKDG
DevG4      LDDPLSAVDTHVARHLFEQCMRGYLRERIVILATHQLQFLQHADQIVIMDKG
```

(C)     CLUSTAL X (1.8) multiple sequence alignment of ABC-membrane II

```
hMRP4      WIVFIFLILLNTAAQVAYVLQDWWLSYWANKQ-SMLNVTVNGGGNVTEKLD--LNWYLG-
DevG4      FVMMGFCVLSQGLASLG----DYFLSYWVTKKGNVAYRADNNDTTRSEELEPRLSTWLRD hMRP4      -------------IYSGLTVATVLFGIARSLLVFYVLVNSSQTLHNKMFESILKAPVLFF
DevG4      IGLSVDAEMLDTYIFTVITVLTILVTVARSFLFFNLAMKASIRLHNSMFRGITRAAMYFF hMRP4      DRNPIGRILNRFSKDIGHLDDLLPLTFLDFIQTLLQVVGVVSVAVAVIPWIAIPLVPLGI
DevG4      NTNPSGRILNRFSKDMGQVDEILPAVMMDVIQIFLALAGIVIVIAVVNPLFLIPTVVLGI hMRP4      IFIFLRRYFLETSRDVKRLESTTRSPVFSHLSSSLQGLWTIRAYKAEERCQELFDAHQDL
DevG4      IFYQLRTFYLKTSRDVKRMEAITRSPVYSHLAASLTGLSTIRAFGAQRVLEAEFDNYQDM hMRP4      HSEAWFLFLTTSRWFAVRLDAICAMFVIIVAFGSLILAKTLDAGQVGLALSYALTLMGMF
DevG4      HSSAFYMFISTSRAFGYWLDCFCVIYIAIITLSFFIFP-PANGGDVGLAITQAMGMTGMV hMRP4      QWCV
DevG4      QWGM
```

(D)     CLUSTAL X (1.8) multiple sequence alignment of ABC-tran II

```
hMRP4      -EKVGIVGRTGAGKSSLISALFRLSEPEGKIWIDKILTTEIGLHDLRKKMSIIPQEPVLF
mMRP4      REKVGIVGRTGAGKSSLISALFRLSEPEGKIWIDKILTTEIGLHDLRKKMSIIPQEPVLF
DevG4      KEKVGIVGRTGAGKSSLINALFRLSYNDGSVLIDKRDTSEMGLHDLRSKISIIPQEPVLF hMRP4      TGTMRKNLDPFKEHTDEELWNALQEVQLKETIEDLPGKMDTELAESGSNFSVGQRQLVCL
mMRP4      TGTMRKNLDPFNEHTDEELWRALEEVQLKEAIEDLPGKMDTELAESGSNFSVGQRQLVCL
```

FIGURE 11 (Continued)

```
DevG4           SGTMRYNLDPFDEYSDDKLWRSLEEVKLKEVVADLPSGLQSKITEGGTNFSVGQRQLVCL hMRP4           ARAILRKNQILIIDEATANVDPRTDELIQKKIREKFAHCTVLTIAHRLNTIIDSDKIMVL
mMRP4           A-----------------------------------------------------------
DevG4           ARAILRENRILVMDEATANVDPQTDGLIQTTIRNKFKECTVLTIAHRLHTIMDSDKVLVM hMRP4           DSG
mMRP4           ---
DevG4           DAG
```

FIGURE 12: Expression of DevG4 (MRP4) in mammalian tissues
(A) Real-time PCR analysis of DevG4 (MRP4) expression in wildtype mouse tissues
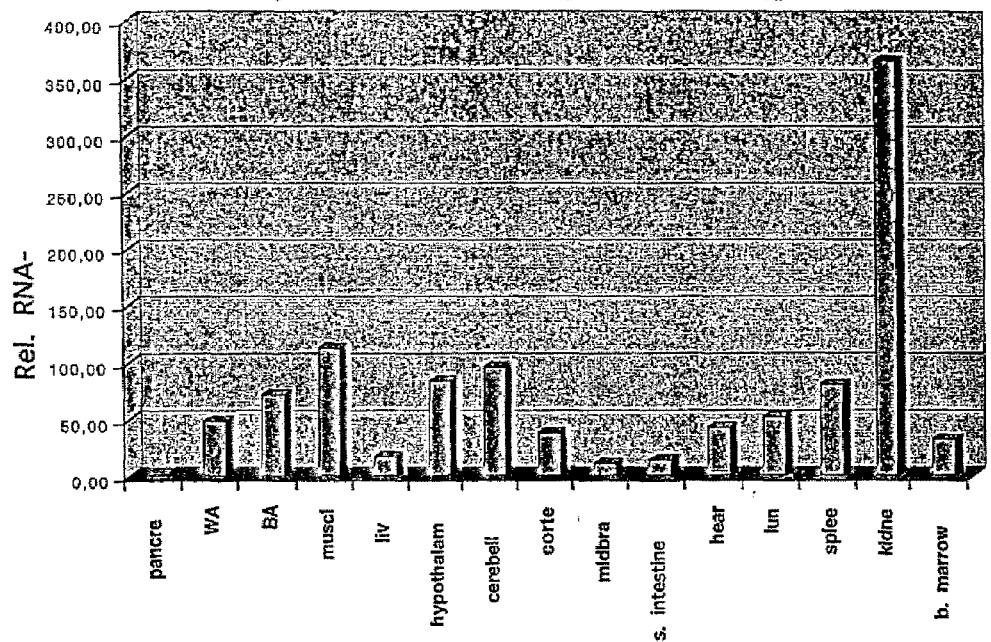
(B) Real-time PCR mediated comparison of DevG4 (MRP4) expression in different mouse models
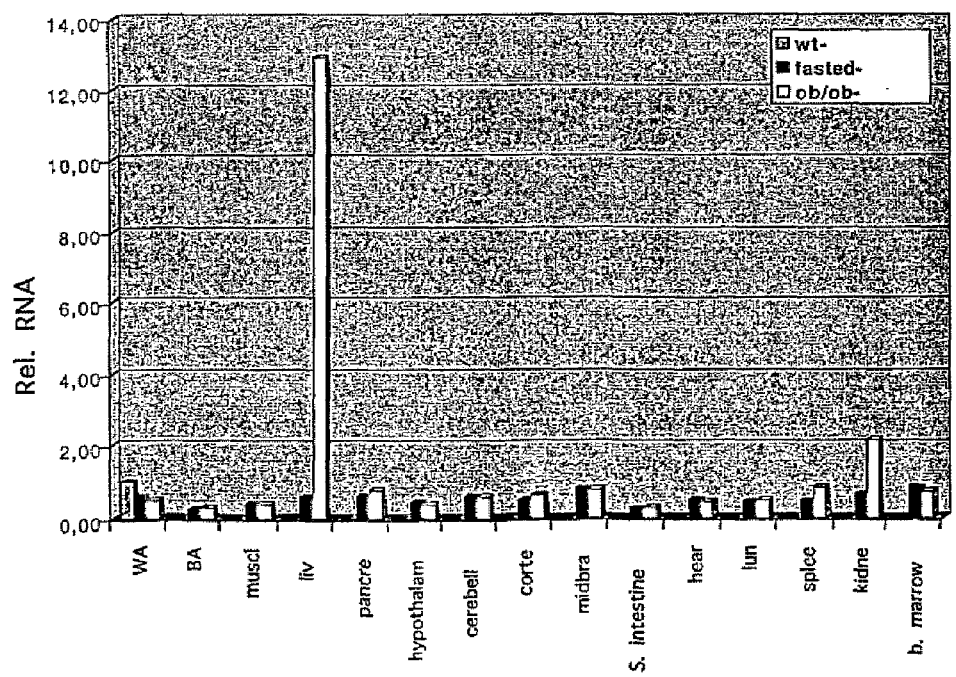

(C) Real-time PCR mediated comparison of DevG4 (MRP4) expression during the differentiation of 3T3-L1 cells from pre-adipocytes to mature adipocytes FIGURE 13: Increase of triglyceride content of homozygous flies
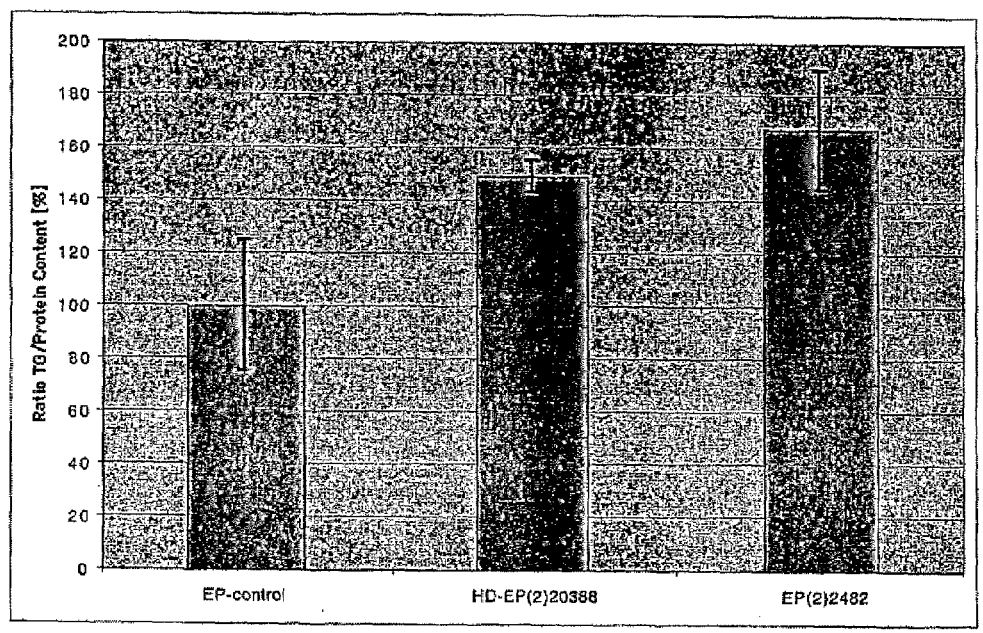

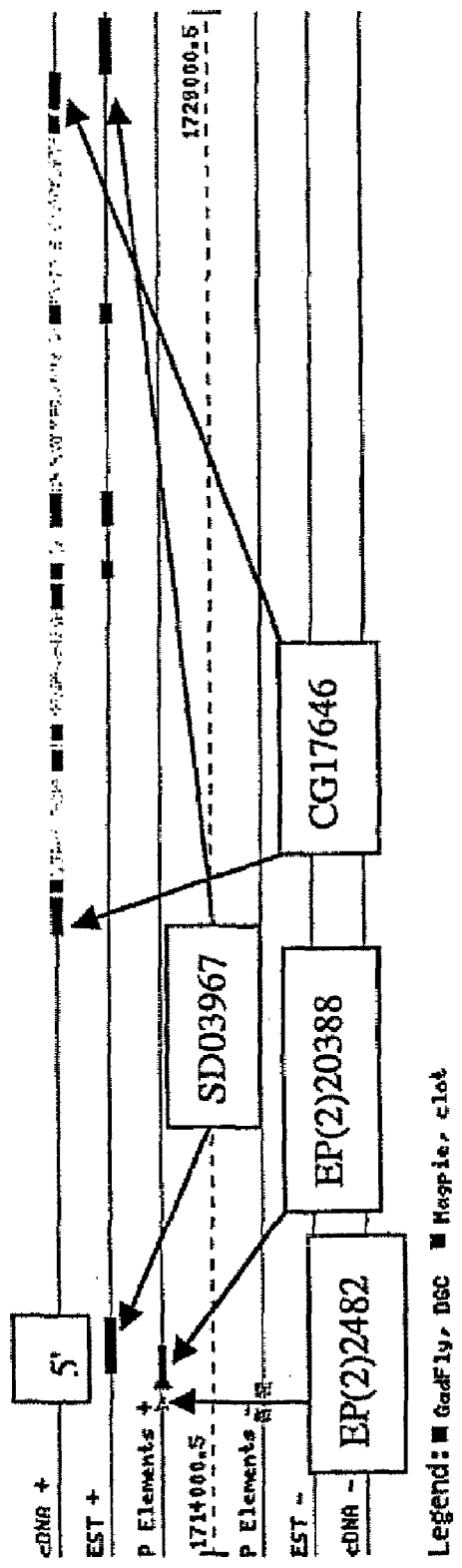
FIGURE 14: Molecular organisation of the *DevG22* locus

FIGURE 15A: Nucleotide sequence of the *DevG22* cDNA (SEQ ID NO:11)

```
CGTGGCGAGC GCACGTGCAG CGGAACGTAT ATATTCTTGT TCAGCGGGAT CGGAATCGGG GAAAATCGAG
ACATATACAG AAATCGAAGC ACATTATGTA TAACACACGC AATTCAAATT AATTTACGCG TCGCTGCCCA
TCTGCATAAG TTCAATGGAA GCAGAGGCAA AAGTTTGAGC AAAAGCACAG ACCGCGTACC GAGAGGAAAA
GTAGAAAAAT GTGAAGAAAG TGCAACAAAG TCGAATTAGT AAATCAACCA AAAAAAAAAA ATACAAGAAG
TGCACCTAAC AACAATAAAA TAAAACAATC ATCGCGTGTT CGTCCATATG TTAAACAAAG GTTAATTAAA
CAGACTGCAA TTATTCCGCG TTGCAGTTGG CAGTTGGTGG AGTACAAGAA ACATTTCTTT GTGTTTATGT
GTTTTCATTC AGAAATATTC GTTACGCGTC TACTCTTACG ACTTCCCGAG AAGAATCCGA ATAATTTGTG
TACTACTGCG AAGAAAGAGA CGCTGAAGAG CTTGCAGTCA AGAGATACCC CTTCTGACTA GAAACATTGA
GGATTCCGTG CAAACATGAC CCTCTTGCCA GACATCAAGG CATCGGATGC CGCCTGCTGC GTGGGAGGTG
CGAACAGCGA TGCCAGCAGC AGTTCCGGCG TCTGCAGCCT CAAGGGTCAC CATGGTGACC CCGACAGCGG
TTGCCTGGGC ATCAACTGTT GCACCACGGC GGCCAGCTCG GAGCTGTCCA TCGACGAGAC GTCATCGACC
TCGTCCAGAG GCTCCTGCGA GTTGACCAGC AAGGTGACCA ACGACCTGAA CGGATTCCAG AGTCCGAACT
ACCACCAGGC GGTGGCGCAC GCCAACTTCG ACCACTGCGA TCCCGTGGAC ATCCAGTTCG CCGACGTGCG
CTACACAGTG AAGAAGTTCT CCTTCCCGGA GCCGAAACCTC GTCACCAAGG AGATCCTTCA TGGCCTGAAC
GGCAGCTTCC GGTCTGGCGA ACTCACAGCC ATCATGGGTC CTTCGGGCGC CGGCAAGAGC ACGCTGCTGA
ATGTGATGTC CGGATTTTGT AATGGACGTG GTGGTAAAGA CGATGCCCCA GGCGGTACAC GGGTTTTCAT
TGCTAAACGT TATCGCTCCA CTGGCGTGTC GGGCGATATC CGGGTTAATA GAAAGCCCAT GGCTCCCAGC
TCCGAGAGGT TCCGCCAAAT GCTGTGCTAC ATCCACCAGG ACGATCTGCT GCGTCCACAG CTGTTGGTCG
GCGAGATAAT GCTGCTGGCG GCACATCTGA AGCTGGGCTT CAAGGTCACC AAGGCGTACA AGATGGATCT
GATCAAGCAC ATCTTATCGC TGCTGGGTCT GGACCATCGC TACAATGTGC CCACTGGGAA GCTTTCGGGT
GGCCAGAAGA AGCGACTCGC AATCGCCCTG GAGCTGATAA GTAATCCTCC CGTGCTATAT CTGGATGAGC
CGACGACTGG CCTGGACAGC TCCTCGTGCA GCTCCTGCGT GGCTCTGCTG AAGAAACTGG CGTCGCAGGG
CCACACGATA GTCTGCACCA TCCATCAGCC AAGTGCCCTC ATCTTCGAGA TGTTCGACAA GCTCTACACC
GTCGTCGATG GCCACTGCAT GTACCAAGGA CCTGTCGCG AACTGGTGCC CTTCCTGGCC GACCAGCAGC
TCGTCTGCCC CAGTTACCAC AACCCAGCTG ACTATCTACT GGAAGTGGCC GTGGGCGAGC ATCAACGTGA
CCTGAATGAG CTAATCCATG CGGCCAATAA AAAGTATTAC GAGGATGTGG ATCGCCATAG GTATATGAGC
AGTGATGATA TGGCACGCCT CGTGGAAAGC ATTAAGAAA ACATGGGCGG CAAGGCAGTG GTAAAAACCA
GTGAAGCGCT GGCAGCATTT GCGGCGGCGC AATTCTCCAG CTTCGACTAT GTAAAGCCCT CGCCGCAGGA
GCTGGCTCTG GAGGAGATCA AGGCACTGAG CGGCGGCCCC GAGAGCGCGG ATCCCGATCT CCTCGAGAAA
AATCTGAGGC CACAGCCACA GCCGCTTGCC AAAGCCGGTG AGCTTGCCAG GCCGCCGAAT GCCATTCGAT
CGGCCTCGTT CCTCATGCAG TATGTGCTCC TGATGCAGCG CATCTTGATT TGCGCCAAGC GAAACTACTT
TCTGCTGCTG GCCCGCATCT TCTCGCACAT TTTCATCGGA GTCGTCTTCG GGTATCTGTA CATGAACGTG
GGCAACAATG CCCAGAGTGT GCTGGGAAAC TACGTGTATC TGTACGGCTC CACGCTGCTC TTGGTCTACA
CCGGTAAAAT GGCTGTGGTC TTGACATTTC CGCTGGAAAT TGACATGTTG ACACGGGAGC ACTTCAACCG
CTGGTACAAA CTGGGTCCCT ACTTCCTCTC GTTGATCTCC TTCGAAATAC CCTTCCAGGT GAGCACCGCC
ATAGAATAG
```

FIGURE 15B: Amino acid sequence of DevG22 (SEQ ID NO:12)

```
MTLLPDIKAS DAACCVGGAN SDASSSSGVC SLKGHHGDPD SGCLGINCCT TAASSELSID ETSSTSSRGS
CELTSKVTND LNGFQSPNYH QAVAHANFDH CDPVDIQFAD VRYTVKKFSF PERKFVTKEI LHGLNGSFRS
GELTAIMGPS GAGKSTLLNV MSGFCNGRGG KDDAPGGTRV FIAKRYRSTG VSGDIRVNRK PMAPSSERFR
QMLCYIHQDD LLRPQLLVGE IMLLAAHLKL GFKVTKAYKM DLIKHILSLL GLDHRYNVPT GKLSGGQKKR
LAIALELISN PPVLYLDEPT TGLDSSSCSS CVALLKKLAS QGHTIVCTIH QPSALIFEMF DKLYTVVDGH
CMYQGPVREL VPFLADQQLV CPSYHNPADY LLEVAVGEHQ RDLNELIHAA NKKYYEDVDR HRYMSSDDMA
RLVESIKENM GCKAVVKTSE ALAAFAAAQF SSPDYVKPSP QELALEEIKA LSGGPESADP DLLEKNLRPQ
PQPLAKAGEL ARPPNAIRSA SFLMQYVLLM QRILICAKRN YFLLLARIFS HIFIGVVFGY LYMNVGNNAQ
SVLGNYVYLY GSTLLLVYTG KMAVVLTFPL EIDMLTREHF NRWYKLGPYF LSLISFEIPF QVSTAIE
```

FIGURE 15C: Nucleotide sequence of the human DevG22 homolog (SEQ ID NO:5)

```
GCTTTATAAA GGGGAGTTTC CCTGCACAAG CTCTCTCTCT TGTCTGCCGC CATGTGAGAC ATGCCTTTCA
CCTTCCGCCA TGATCATGAG GCTTCCCCAG CCACATGGAA CTAATGCCAG CAGTTACTCT GCAGAGATGA
CGGAGCCCAA GTCGGTGTGT GTCTCGGTGG ATGAGGTGGT GTCCAGCAAC ATGGAGGCCA CTGAGACGGA
CCTGCTGAAT GGACATCTGA AAAAAGTAGA TAATAACCTC ACGGAAGCCC AGCGCTTCTC CTCCTTGCCT
CGGAGGGCAG CTGTGAACAT TGAATTCAGG GACCTTTCCT ATTCGGTTCC TGAAGGACCC TGGTGGAGGA
AGAAAGGATA CAAGACCCTC CTGAAGGAA TTCCGGGAA GTTCAATAGT GGTGAGTTGG TGGCCATTAT
GGGTCCTTCC GGGGCCGGCA AGTCCACGCT GATGAACATC CTGGCTGGAT ACAGGGAGAC GGGCATGAAG
GGGGCCGTCC TCATCAACGG CCTGCCCCGG GACCTGCGCT GCTTCCGGAA GGTGCCTGC TACATCATGC
AGGATGACAT GCTGCTGCCG CATCTCACTG TGCAGGAGGC CATGATGGTG TCGGCACATC TGAAGCTTCA
```

FIGURE 15C (Continued)

```
GGAGAAGGAT GAAGGCAGAA GGGAAATGGT CAAGGAGATA CTGACAGCGC TGGGCTTGCT GTCTTGCGCC
AACACGCGGA CCCGGGAGCCT GTCAGGTGGT CAGCGCAAGC GCCTGGCCAT CGCGCTGGAG CTGGTGAACA
ACCCTCCAGT CATGTTCTTC GATGAGCCCA CCAGCGGCCT GGACAGCGCC TCCTGCTTCC AGGTGGTCTC
GCTGATGAAA GGGCTCGCTC AAGGGGGTCG CTCCATCATT TGCACCATCC ACCAGCCCAG CGCCAAACTC
TTCGAGCTGT TCGACCAGCT TTACGTCCTG AGTCAAGGAC AATGTGTGTA CCGGGGAAAA GTCTGCAATC
TTGTGCCATA TTTGAGGGAT TTGGGTCTGA ACTGCCCAAC CTACCACAAC CCAGCAGATT TTGTCATGGA
GGTTGCATCC GGCAGTACG GTGATCAGAA CAGTCGGCTG GTGAGAGCGG TTCGGGAGGG CATGTGTGAC
TCAGACCACA AGAGAGACCT CGGGGGTGAT GCCGAGGTGA ACCCTTTTCT TTGGCACCGG CCCTCTGAAG
AGGACTCCTC GTCCATGGAA GGCTGCCACA GCTTCTCTGC CAGCTGCCTC ACGCAGTTCT GCATCCTCTT
CAAGAGGACC TTCCTCAGCA TCATGAGGGA CTCGGTCCTG ACACACCTGC GCATCACCTC GCACATTGGG
ATCGGCCTCC TCATTGGCCT GCTGTACTTG GGGATCGGGA ACGAAGCCAA GAAGGTCTTG AGCAACTCCG
GCTTCCTCTT CTTCTCCATG CTGTTCCTCA TGTTCGCGGC CCTCATGCCT ACTGTTCTGA CATTTCCCCT
GGAGATGGGA GTCTTTCTTC GGGAACACCT GAACTACTGG TACAGCCTGA AGGCCTACTA CCTGGCCAAG
ACCATGGCAG ACGTGCCCTT TCAGATCATG TTCCCAGTGG CCTACTGCAG CATCGTGTAC TGGATGACGT
CGCAGCCGTC CGACGCCGTG CGCTTTGTGC TGTTTGCCGC GCTGGGCACC ATGACCTCCC TGGTGGCACA
GTCCCTGGGC CTGCTGATCG GAGCCGCCTC CACGTCCCTG CAGGTGGCCA CTTTCGTGGG CCCAGTGACA
GCCATCCCGG TGCTCCTGTT CTCGGGTTC TTCGTCAGCT TCGACACCAT CCCCACGTAC CTACAGTGGA
TGTCCTACAT CTCCTATGTC AGGTATGGGT TCGAAGGGGT CATCCTCTCC ATCTATGGCT TAGACCGGGA
AGATCTGCAC TGTGACATCG ACGAGACGTG CCACTTCCAG AAGTCGGAGG CCATCCTGCG GGAGCTGGAC
GTGGAAAATG CCAAGCTGTA CCTGGACTTC ATCGTACTCG GGATTTTCTT CATCTCCCTC CGCCTCATTG
CCTATTTTGT CCTCAGGTAC AAAATCCGGG CAGAGAGGTA AAACACCTGA ATGCCAGGAA ACAGGAAGAT
TAGACACTGT GGCCGAGGGC ACGTCTAGAA TCGAGGAGGC AAGCCTGTGC CCGACCGACG ACACAGAGAC
TCTTCTGATC CAACCCCTAG AACCGCGTTG GGTTTGTGGG TGTCTCGTGC TCAGCCACTC TGCCCAGCTG
GGTTGGATCT TCTCTCCATT CCCCTTTCTA GCTTTACTA GGAAGATGTA GGCAGATTGG TGGTTTTTTT
TTTTTTAACA TACAGAATTT TAAATACCAC AACTGTAAAG GAATTTAAAG CTGCAACACA GCTGGTGATG
AGAGGCTTCC TCAGTCCAGT CGCTCCTTAG CACCAGGCAC CGTGGGTCCT GGATGGGGAA CTGCAAGCAG
CCTCTCAGCT GATGGCTGCA CAGTCAGATG TCTGGTGGCA GAGAGTCCGA GCATGGAGCG ATTCCATTTT
ATGACTGTTA TTTTTCACAT TTTCATCTTT CTAAGGTGTG TCTCTTTTCC AATGAGAAGT CATTTTTGCA
AGCCAAAAGT CGATCAATCG CATTCATTTT AAGAAATTAT ACCTTTTTAG TACTTGCTGA AGAATGATTC
AGGGTAAATC ACATACTTTG TTTAGAGAGG CGAGGGGTTT AACCGAGTCA CCCAGCTGGT CTCATACATA
GACAGCACTT GTGAAGGATT GAATGCAGGT TCCAGGTGGA GGGAAGACGT GGACACCATC TCCACTGAGC
CATGCAGACA TTTTTAAAAG CTATACAAAA AATTGTGAGA AGACATTGGC CAACTCTTTC AAAGTCTTTC
TTTTTCCACG TGCTTCTTAT TTTAAGCGAA ATATATTGTT TGTTTCTTCC T
```

FIGURE 15D: Amino acid sequence of the human DevG22 homolog (SEQ ID NO:6)

```
MIMRLPQPHG TNASSYSAEM TEPKSVCVSV DEVVSSNMEA TETDLLNGEL KKVDNNLTEA QRFSSLPRRA
AVNIEFRDLS YSVPEGPWWR KKGYKTLLKG ISGKFNSGEL VAIMGPSGAG KSTLMNILAG YRETGMKGAV
LINGLPRDLR CFRKVSCYIM QDDMLLPHLT VQEAMMVSAH LKLQEKDEGR REMVKEILTA LGLLSCANTR
TGSLSGGQRK RLAIALELVN NPPVMFFDEP TSGLDSASCF QVVSLMKGLA QGGRSIICTI HQPSAKLFEL
FDQLYVLSQG QCVYRGKVCN LVPYLRDLGL NCPTYHNPAD FVMEVASGEY GDQNSRLVRA VREGMCDSDH
KRDLGGDAEV NPPLWHRPSE EDSSSMEGCH SFSASCLTQF CILFKRTFLS IMRDSVLTHL RITSHIGIGL
LIGLLYLGIG NEAKKVLSNS GFLFFSMLFL MFAALMPTVL TFPLEMGVFL REHLNYWYSL KAYYLAKTMA
DVPFQIMFPV AYCSIVYWMT SQPSDAVRFV LFAALGTMTS LVAQSLGLLI GAASTSLQVA TFVGPVTAIP
VLLFSGFFVS FDTIPTYLQW MSYISYVRYG FEGVILSIYG LDREDLHCDI DETCHFQKSE AILRELDVEN
AKLYLDFIVL GIFFISLRLI AYFVLRYKIR AER
```

FIGURE 16: Protein domains of the DevG22 protein

FIGURE 17: CLUSTAL X (1.8) multiple sequence alignment of DevG22 proteins from human (hDevG22), mouse (mDevG22), and Drosophila (DevG22).

```
hDevG22      -----------MAAFSVGTAMNASSYSAEMTEPK---------------------SVCVSVD
mDevG22      ------MACLMAAFSVGTAMNASSYSAAMTEPK---------------------SVCVSVD
DevG22       MTLLPDIKASDAACCVGGANSDASSSSGVCSLKGHHGDPDSGCLGINCCTTAASSELSID hDevG22      EVVSSN---MEATETDLLNGHLKKVDNNLTEAQRFSSLPRRAAVNIEFRDLSYSVPEGPW
mDevG22      EVVSSN---VDEVETDLLNGHLKKVDNNFTEAQRFSSLPRRAAVNIEFKDLSYSVPEGPW
DevG22       ETSSTSSRGSCELTSKVTNDLNGFQSPNYHQAVAHANFDHCDPVDIQFADVRYTVKKFSF hDevG22      WR-KKGYKTLLKGISGKFNSGELVAIMGPSGAGKSTLMNILAG-----------------
mDevG22      WK-KKGYKTLLKGISGKFNSGELVAIMGPSGAGKSTLMNILAG-----------------
DevG22       PERKFVTKEILHGLNGSFRSGELTAIMGPSCAGKSTLLNVMSGFCNGRGGKDDAPGGTRV hDevG22      -----YRETGMKGAVLING--LPRDLRCFRKVSCYIMQDDMLLPHLTVQEAMMVSAHLKL
mDevG22      -----YRETGMKGAVLING--MPRDLRCFRKVSCYIMQDDMLLPHLTVQEAMMVSAHLKL
DevG22       FIAKRYRSTGVSGDIRVNRKPMAPSSERFRQMLCYIHQDDLLRPQLLVGEIMLLAAHLKL hDevG22      --QEKDEGRREMVKEILTALGLLSCANTRTGSLSGGQRKRLAIALELVNNPPVMFFDEPT
mDevG22      --QEKDEGRREMVKEILTALGLLPCANTRTGSLSGGQRKRLAIALELVNNPPVMFFDEPT
DevG22       GFKVTKAYKMDLIKHILSLLGLDHRYNVPTGKLSGGQKKRLAIALELISNPPVLYLDEPT hDevG22      SGLDSASCFQVVSLMKGLAQGGRSIICTIHQPSAKLFELFDQLYVLSQGQCVYRGKVCNL
mDevG22      SGLDSASCFQVVSLMKGLAQGGRSIVCTIHQPSAKLFELFDQLYVLSQGQCVYRGKVSNL
DevG22       TGLDSSSCSSCVALLKKLASQGHTIVCTIHQPSALIFEMFDKLYTVVDGHCMYQGPVREL hDevG22      VPYLRDLGLNCPTYHNPADFVMEVASGEYGDQNSRLVRAVREGMCDSDHKRDLGGDAEVN
mDevG22      VPYLRDLGLNCPTYHNPADFVMEVASGEYGDQNSRLVRAVREGMCDADYKRDLGGDTDVN
DevG22       VPFLADQQLVCPSYHNPADYLLEVAVGEHQRDLNELIHAANK------------------ hDevG22      PFLWHRPSEEVKQTKRLKGLRKDSSSMEGCHSFSASCLTQFCILFKRTFLSIMRDSVLTH
mDevG22      PFLWHRPAE-----------EDSASMEGCHSFSASCLTQFCILFKRTFLSIMRDSVLTH
DevG22       -------------------------------------------------K-YYEDVDR-- hDevG22      LRITSHIGIGLLIGLLYLGIGNEAKKVLSNSGFLFFSMLFLMFAALMPTVLTFPLEMGVF
mDevG22      LRITSHIGIGLLIGLLYLGIGNEAKKVLSNSGFLFFSMLFLMFAALMPTVLTFPLEMSVF
DevG22       HRYMSSDDMARLVESIKENMGGKAVVKTSEALAAFAAAQFSSFDYVKPSPQELALEEIKA hDevG22      LREHLNYWYSLKAYYLAKTMADVPFQIMFPVAYCSIVYWMTSQPSDAVRFVLFAALGTMT
mDevG22      LREHLNYWYSLKAYYLAKTMADVPFQIMFPVAYCSIVYWMTSQPSDAVRFVLFAALGTMT
DevG22       LSGGP---ESADPDLLEKNLRPQPQ----PLAKAGELARPPNAIRSASFLMQYVLLMQRI hDevG22      SLVAQSLGLLIGAASTSLQVATFVGPVTAIPVLLFSGFFVSFDTIPTYLQWMSYISYVRY
mDevG22      SLVAQSLGLLIGAASTSLQVATFVGPVTAIPVLLFSGFFVSFDTIPAYLQWMSYISYVRY
DevG22       LICAKRN--------YFLLLAR-------IFSHIFIGVVFGYLYMNVGNNAQSVLGNYVY hDevG22      GFEGVILSIYGLDREDLHCDIDETCHFQKSEAILRELDVENAKLYLDFIVLGIFFISLRL
mDevG22      GFEGVILSIYGLDREDLHCDIAETCHFQKSEAILRELDVENAKLYLDFIVLGIFFISLRL
DevG22       LYGSTLLLVY----------TG--KMAVVLTFPLEIDMLTREHFNRWYKLGPYFLSL-- hDevG22      IAYFVLRYKIRAER-
mDevG22      IAYFVLRYKIRAER-
DevG22       -ISFEIPFQVSTAIE
```

FIGURE 18: Expression of DevG22 in mammalian tissues
(A) Real-time PCR analysis of DevG22 expression in wildtype mouse tissues
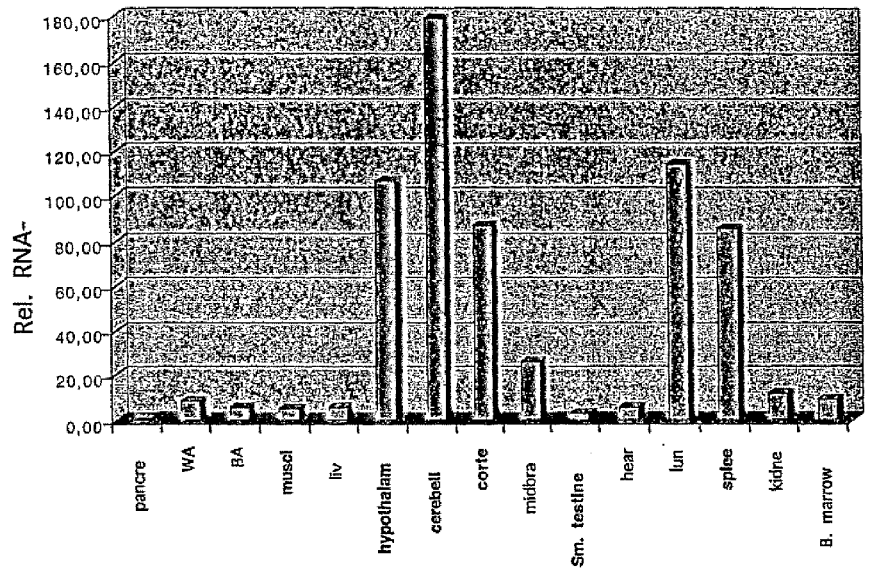
(B) Real-time PCR mediated comparison of DevG22 expression in different mouse models
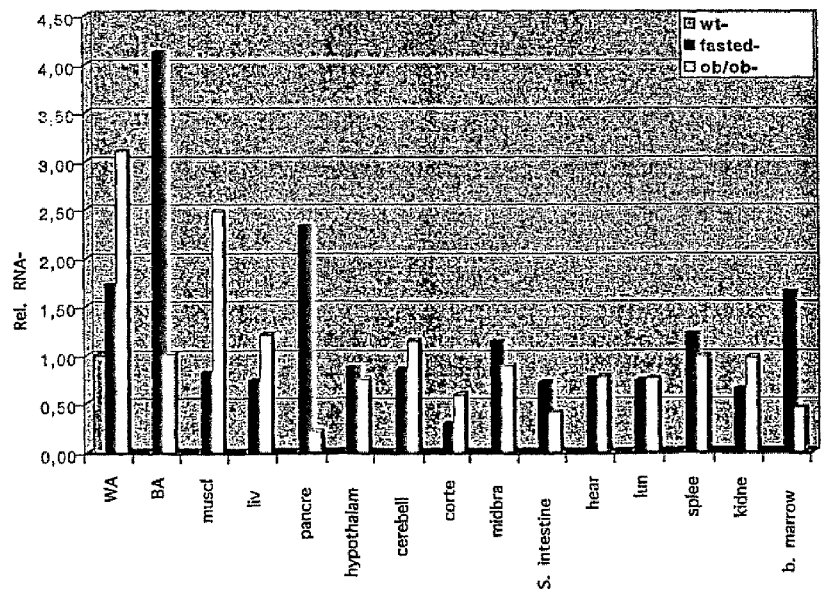

(C) Real-time PCR mediated comparison of DevG22 expression during the differentiation of 3T3-L1 cells from pre-adipocytes to mature adipocytes

PROTEIN DISULFIDE ISOMERASE AND ABC TRANSPORTER HOMOLOGOUS PROTEINS INVOLVED IN THE REGULATION OF ENERGY HOMEOSTASIS

CROSS-REFERENCE TO RELATED APPLICATIONS

This application claims priority to PCT Patent Application No. PCT/EP02/03540 filed Mar. 28, 2002 and European Patent Applications No. EP01 108 315.1 filed Apr. 2, 2001 and EP01 113 419.4 filed Jun. 1, 2001.

DESCRIPTION

This invention relates to the use of nucleic acid and amino acid sequences of protein disulfide isomerase and ABC transporter homologous proteins, and to the use of these sequences in the diagnosis, study, prevention, and treatment of diseases and disorders related to body-weight regulation, for example, but not limited to, metabolic diseases such as obesity, as well as related disorders such as adipositas, eating disorders, wasting syndromes (cachexia), pancreatic dysfunctions (such as diabetes mellitus), hypertension, arteriosclerosis, coronary heart disease, hypercholesterolemia, dyslipidemia, osteoarthritis, gallstones, cancer, e.g. cancers of the reproductive organs, sleep apnea, and others.

Obesity is one of the most prevalent metabolic disorders in the world. It is still poorly understood human disease that becomes more and more relevant for western society. Obesity is defined as an excess of body fat, frequently resulting in a significant impairment of health. Besides severe risks of illness such as diabetes, hypertension and heart disease, individuals suffering from obesity are often isolated socially. Human obesity is strongly influenced by environmental and genetic factors, whereby the environmental influence is often a hurdle for the identification of (human) obesity genes. Obesity is influenced by genetic, metabolic, biochemical, psychological, and behavioral factors. As such, it is a complex disorder that must be addressed on several fronts to achieve lasting positive clinical outcome. Obese individuals are prone to ailments including: diabetes mellitus, hypertension, coronary heart disease, hypercholesterolemia, dyslipidemia, osteoarthritis, gallstones, cancer, e.g. cancers of the reproductive organs, and sleep apnea.

Obesity is not to be considered as a single disorder but a heterogeneous group of conditions with (potential) multiple causes. Obesity is also characterized by elevated fasting plasma insulin and an exaggerated insulin response to oral glucose intake (Koltermann, J. Clin. Invest 65, 1980, 1272–1284) and a clear involvement of obesity in type 2 diabetes mellitus can be confirmed (Kopelman, Nature 404, 2000, 635–643).

Even if several candidate genes have been described which are supposed to influence the homeostatic system(s) that regulate body mass/weight, like leptin, VCPI, VCPL, or the peroxisome proliferator-activated receptor-gamma co-activator, the distinct molecular mechanisms and/or molecules influencing obesity or body weight/body mass regulations are not known.

Therefore, the technical problem underlying the present invention was to provide for means and methods for modulating (pathological) metabolic conditions influencing body-weight regulation and/or energy homeostatic circuits. The solution to said technical problem is achieved by providing the embodiments characterized in the claims.

Accordingly, the present invention relates to genes with novel functions in body-weight regulation, energy homeostasis, metabolism, and obesity. The present invention discloses specific genes involved in the regulation of body-weight, energy homeostasis, metabolism, and obesity, and thus in disorders related thereto such as eating disorder, cachexia, diabetes mellitus, hypertension, coronary heart disease, hypercholesterolemia, dyslipidemia, osteoarthritis, gallstones, cancer, e.g. cancers of the reproductive organs, and sleep apnea. The present invention describes human protein disulfide isomerase, MRP4, and ABC8 (white) genes as being involved in those conditions mentioned above.

Protein disulfide isomerase (PDI) is a protein-thiol oxidoreductase that catalyzes the folding of protein disulfides. PDI has been demonstrated to participate in the regulation of reception function, cell-cell interaction, gene expression, and actin filament polymerization. PDI has acts as a chaperone and subunit of prolyl 4-hydroxylase and microsomal triglyceride transfer protein (MTP). MTP is accelerating the transport of triglyceride, cholesteryl ester, and phospholipid between membranes (Berriot-Varoqueaux et al., 2000, Annu Rev Nutr. 20, 663–697). Mutations in MTP are the cause for abetalipoproteinemia, a hereditary disease with limited production of chylomicrons and very low-density lipoproteins (VLDL) in the intestine and liver (Rehberg et al., 1996, J Biol Chem. 271(47), 29945–52). Intracellular VLDL is associated with chaperones including PDI and glucose regulated protein 94 (GRP94, endoplasmin) and assembles with apolipoprotein B (Berriot-Varoqueaux et al., SUPRA). These chaperones are endogenous substrates of sphingosine-dependent kinases (SDKs) and regulated by signal transduction pathways (see, for example, Megidish et al., 1999, Biochemistry. 38(11), 3369–78).

The chaperones are found in the endoplasmic reticulum where the lipidation of lipoproteins like apolipoprotein B might take place (Hussain et al., 1997, Biochemistry. 36(42), 13060–7.; Wu. et al., 1996, J Biol Chem. 271(17), 10227–81). In addition, the secretion of apolipoprotein B is dependent on PDI (Wang et al., 1997, J. Biol. Chem. 272(44), 27644–51).

The formation or assembly of additional proteins strongly depends on the activity of specific groups of chaperones. PDI is regulating the formation of native insulin from its precursors and the insulin degradation (Tang et al., 1988, Biochem J. 255(2), 451–5; Duckworth et al., 1998, Endocr Rev. 19(5), 608–24). Insulin signaling is crucial for the proper regulation of blood glucose levels and lipid metabolism.

Dietary energy tissue-specifically regulates endoplasmic reticulum chaperone gene expression in the liver of mice, especially glucose regulated proteins (Dhahbi et al., 1997, J Nutr. 127(9), 1758–64).

Additionally PDI mRNA is strongly expressed in adipose tissue (Klaus et al., 1990, Mol Cell Endocrinol. 73(2–3), 105–10), emphasizing their important roles in metabolic pathways.

Chaperones are also essential for the cellular protection against stress in its different forms like oxidative, heat shock or hypoglycemic stress (Barnes & Smoak, 2000, Anat Embryol. 202(1), 67–74, Lee, 1992. Curr Opin Biol. 4(2), 267–73) preventing cells to undergo apoptosis.

Furthermore, chaperones are involved in different diseases like Alzheimer's Disease (Yoo et al., 2001, Biochem Biophys Res Commun. 280(1), 249–58), Parkinson (Duan & Mattson, 1999, J Neurosci Res. 59(13), 195–206), Rheumatoid Arthritis (Corrigall et al., 2001, J Immunol. 166(3), 1492–98) or neuropsychological disease leading to suicide of patients (Bown et al., 2000, *Neuropsychopharmacology.* 22(3), 327–32).

ATP-binding cassette (ABC) genes encode a family of transport proteins that are known to be involved in a number of human genetic diseases. For example, polymorphisms of the human homologue of the *Drosophila* white gene are associated with mood and panic disorders (Nakamura et al. 1999 *Mol Psychiatry.* 4(2):155–62). Mutations in the canilicular multispecific organic anion transporter (cMOAT) gene could be the reason for the Dubin-Johnson syndrome leading to hyperbilirubinemia II (Wada et al. 1998, *Hum Mol Genet.* 7(2):203–7). The rod photoreceptor-specific ABC transporter (ABCR) is responsible for the Stargardt disease (Allikmets et al. 1997, *Nat Genet.* 15(3):236–46). The gene encoding ATP-binding cassette transporter 1 (ABC1) is mutated in Tangier disease leading to the absence of plasma high-density lipoprotein (HDL) and deposition of cholesteryl esters in the reticulo-endothelial system with splenomegaly and enlargement of tonsils and lymph nodes (Brooks-Wilson et al. 1999 *Nat Genet.* 22(4):336–45, Bodzioch et al. 1999 *Nat Genet.* 22(4):347–51, Rust et al. 1999, *Nat Genet.* 22(4):352–5). Furthermore a subgroup of ABC transporters are involved in cellular detoxification causing multidrug resistance that counteracts e.g. anti-cancer or HIV treatment (Schuetz et al. 1999 Nat Med. 1999 (9):1048–51).

ABC transporters transport several classes of molecules. ABC1 (ABCA1), the gene mutated in Tangier disease, mediates apoAI associated export of cholesterol and phospholipids from the cell and is regulated by cholesterol efflux ((Brooks-Wilson et al. 1999 Nat Genet. 22(4):336–45, Bodzioch et al. 1999 Nat Genet. 22(4):347–51, Rust et al. 1999, *Nat Genet.* 22(4):352–5Brooks-Wilson et al. 1999, Bodzioch et al. 1999, Rust et al. 1999). ABC1 is expressed on the plasma membrane and Golgi complex and the lipid export process needs vesicular budding between Golgi and plasma membrane that is disturbed in Tangier disease. LDL and $HDL_3$ regulate the expression of ABC1 in macrophages (Orsó et al. 2000 *Nat Genet.* 24:192–6).

The expression of the human homologue of the *Drosophila* white gene (ABC8 or ABCG1) is induced in monocyte-derived macrophages during cholesterol influx mediated by LDL and is downregulated through lipid efflux mediated by cholesterol acceptor $HDL_3$. ABC8 is expressed on the cell surface and intracellular compartments of cholesterol-loaded macrophages and its expression is also regulated by oxysterols that act through nuclear oxysterol receptors, liver X receptors (LXRs) and by retinoid X receptor ligand. Therefore, ABC8 activity in macrophages might be crucial for cholesterol metabolism and the development of arteriosclerosis similar to ABC1. LXR expression is regulated through PPARg gamma signalling that is essential for adipogenesis and therefore PPARg gamma signalling might regulate the expression of ABC1 and ABC8 transporters at least in macrophages (Klucken et al. 2000 *Proc Natl Acad Sci USA.* 97(2):817–22., Venkateswaran et al. 2000 *J Biol Chem.* 275(19):14700–7).

Another subgroup of ABC transporters mediates cellular detoxification and is therefore named Multidrug Resistance-associated Proteins (MRPs) or canilicular Multispecific Organic Anion Transporters (cMOATs). MRP1 has high activity towards compounds conjugated to glutathione (GSH), glucuronide or sulfate and transports sphingolipids, eicosanoids, phosphatidylcholine and phosphatidylethanolamine analogues but the main function is the cellular detoxification. MRP4 (MOAT-B) overexpression is associated with high-level resistance to the nucleoside analogues 9-(2-phosphonylmethoxyethyl)adenine and azidothymidine monophosphate, both of which are used as anti-human immunodeficiency virus (HIV) drugs (Schuetz et al. 1999 *Nat Med.* 5(9):1048–51). MRP4 function in lipid transport is unknown despite the fact that LDL and $HDL_3$ regulate its expression in macrophages.

So far, it has not been described that protein disulfide isomerase or ABC transporters and the homologous human proteins are involved in the regulation of energy homeostasis and body-weight regulation and related disorders, and thus, no functions in metabolic diseases and other diseases as listed above have been discussed. In this invention we demonstrate that the correct gene doses of protein disulphide isomerase and/or of two ABC transporter genes are essential for maintenance of energy homeostasis. A genetic screen was used to identify that the protein disulfide isomerase gene, the MRP4 gene, and/or the white (ABC8) gene cause obesity in *Drosophila melanogaster*, reflected by a significant increase of triglyceride content, the major energy storage substance.

Polynucleotides encoding proteins with homologies to protein disulfide isomerase or ABC transporters present the opportunity to investigate diseases and disorders, including metabolic diseases and disorders such as obesity, as well as related disorders such as described above. Molecules related to protein disulfide isomerase and ABC transporters satisfy a need in the art by providing new compositions useful in diagnosis, treatment, and prognosis of diseases and disorders, including metabolic diseases and disorders such as described above.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure.

The present invention discloses a novel protein disulfide isomerase homologous protein and two novel ABC transporter homologous proteins regulating the energy homeostasis and the fat metabolism, especially the metabolism and storage of triglycerides, and polynucleotides, of triglycerides, and polynucleotides, which identify and encode the proteins disclosed in this invention. The invention also relates to vectors, host cells, antibodies, and recombinant methods for producing the polypeptides and polynucleotides of the invention. The invention also relates to the use of these sequences in the diagnosis, study, prevention, and treatment of diseases and disorders related to body-weight regulation, for example, but not limited to, metabolic diseases such as obesity, as well as related disorders such as adipositas, eating disorders, wasting syndromes (cachexia), pancreatic dysfunctions (such as diabetes mellitus), hypertension, arteriosclerosis, coronary heart disease, hypercholesterolemia, dyslipidemia, osteoarthritis, gallstones, cancer, e.g. cancers of the reproductive organs, sleep apnea, and others.

Protein disulfide isomerase and ABC transporter homologous proteins and nucleic acid molecules coding therefor are obtainable from insect or vertebrate species, e.g. mammals or birds. Particularly preferred are human protein disulfide isomerase and ABC transporter homologous nucleic acids, particularly nucleic acids encoding human protein disulfide isomerase homologous protein (MGC3178; Genbank Accession No. NM_030810 (identical to Genbank Accession No. BC001199) for the mRNA; NP_110437.1 (identical to Genbank Accession No. AAH01199) for the protein), human ATP-binding cassette, subfamily C(CFTR/MRP), member 4 (ABCC4; MRP4; Genbank Accession No. NM_005845 for the mRNA; NP_005836.1 for the protein), and human ATP-binding cassette, sub-family G (WHITE), member 1 (ABCG1; WHITE; Genbank Accession No. XM_009777 for the mRNA; XP_009777.3 for the protein). Also particularly preferred are *Drosophila* protein disulfide isomerase homologous and ABC transporter homologous nucleic acids and polypeptides encoded thereby. In a preferred embodiment the present invention also comprises so-called "ABC-tran" domains of the proteins and nucleic acid molecules coding therefor.

The invention particularly relates to a nucleic acid molecule encoding a polypeptide contributing to regulating the energy homeostasis and the metabolism of triglycerides, wherein said nucleic acid molecule comprises (a) the nucleotide sequence shown in SEQ ID NO:1, SEQ ID NO:3, or SEQ ID NO:5,
(b) a nucleotide sequence which hybridizes at 66° C. in a solution containing 0.2×SSC and 0.1% SDS to the complementary strand of a nucleic acid molecule encoding the amino acid sequence of SEQ ID NO:2, SEQ ID NO:4, or SEQ ID NO:6,
(c) a sequence corresponding to the sequences of (a) or (b) within the degeneration of the genetic code,
(d) a sequence which encodes a polypeptide which is at least 85%, preferably at least 90%, more preferably at least 95%, more preferably at least 98% and up to 99,6% identical to SEQ ID NO:2, SEQ ID NO:4, or SEQ ID NO:6,
(e) a sequence which differs from the nucleic acid molecule of (a) to (d) by mutation and wherein said mutation causes an alteration, deletion, duplication or premature stop in the encoded polypeptide or
(f) a partial sequence of any of the nucleotide sequences of (a) to (e) having a length of at least 15 bases, preferably at least 20 bases, more preferably at least 25 bases and most preferably at least 50 bases.

The invention is based on the discovery that protein disulfide isomerase homologous proteins (particularly PDI-like; referred to as DevG20) and ABC transporter homologous proteins (particularly MRP4 and WHITE; herein referred to as DevG4 and DevG22, respectively) and the polynucleotides encoding these, are involved in the regulation of triglyceride storage and therefore energy homeostasis. The invention describes the use of these compositions for the diagnosis, study, prevention, or treatment of diseases and disorders related to such cells, including metabolic diseases such as obesity, as well as related disorders such as adipositas, eating disorders, wasting syndromes (cachexia), pancreatic dysfunctions (such as diabetes mellitus), hypertension, arteriosclerosis, coronary heart disease, hypercholesterolemia, dyslipidemia, osteoarthritis, gallstones, cancer, e.g. cancers of the reproductive organs, sleep apnea, and others.

To find genes with novel functions in energy homeostasis, metabolism, and obesity, a functional genetic screen was performed with the model organism *Drosophila melanogaster* (Meigen). One resource for screening was a proprietary *Drosophila melanogaster* stock collection of EP-lines. The P-vector of this collection has Gal4-UAS-binding sites fused to a basal promoter that can transcribe adjacent genomic *Drosophila* sequences upon binding of Gal4 to UAS-sites. This enables the EP-line collection for overexpression of endogenous flanking gene sequences. In addition, without activation of the UAS-sites, integration of the EP-element into the gene is likely to cause a reduction of gene activity, and allows determining its function by evaluating the loss-of-function phenotype.

Triglycerides are the most efficient storage for energy in cells. In order to isolate genes with a function in energy homeostasis, several thousand proprietary EP-lines were tested for their triglyceride content after a prolonged feeding period (see Examples for more detail). Lines with significantly changed triglyceride content were selected as positive candidates for further analysis.

Obese people mainly show a significant increase in the content of triglycerides. In this invention, the content of triglycerides of a pool of flies with the same genotype after feeding for six days was analyzed using a triglyceride assay, as, for example, but not for limiting the scope of the invention, is described below in the EXAMPLES section.

The invention encompasses polynucleotides that encode DevG20, DevG4, DevG22, and homologous proteins. Accordingly, any nucleic acid sequence, which encodes the amino acid sequences of DevG20, DevG4, or DevG22, can be used to generate recombinant molecules that express DevG20, DevG4, or DevG22. In a particular embodiment, the invention encompasses the nucleic acid sequence of 1693 base pairs (PDI, referred to as DevG20 SEQ ID NO:1) as shown in FIG. 4A, the nucleic acid sequence of 4487 base pairs (MRP4, referred to as DevG4, SEQ ID NO:3) as shown in FIG. 9A, and the nucleic acid sequence of 2459 base pairs (ABC8, or white, referred to as DevG22 SEQ ID NO:5) as shown in FIG. 15A. It will be appreciated by those skilled in the art that as a result of the degeneracy of the genetic code, a multitude of nucleotide sequences encoding DevG20, DevG4, or DevG22, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequences of naturally occurring DevG20, DevG4, or DevG22, and all such variations are to be considered as being specifically disclosed. Although nucleotide sequences which encode DevG20, DevG4, or DevG22 and variants thereof are preferably capable of hybridising to the nucleotide sequences of the naturally occurring DevG20, DevG4, or DevG22 under appropriately selected conditions of stringency, it may be advantageous to produce nucleotide sequences encoding DevG20, DevG4, or DevG22 or derivatives thereof possessing a substantially different codon usage. Codons may be selected to increase the rate at which expression of the peptide occurs in a particular prokaryotic or eukaryotic host in accordance with the frequency with which particular codons are utilised by the host. Other reasons for substantially altering the nucleotide sequence encoding DevG20, DevG4, or DevG22 and derivatives thereof without altering the encoded amino acid sequences include the production of RNA transcripts having more desirable properties, such as a greater half-life, than transcripts produced from the naturally occurring sequences. The invention also encompasses production of DNA sequences, or portions thereof, which encode DevG20, DevG4, or DevG22 and derivatives thereof, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding DevG20, DevG4, or DevG22 or any portion thereof.

Also encompassed by the invention are polynucleotide sequences that are capable of hybridising to the claimed nucleotide sequences, and in particular, those shown in SEQ ID NO:1, SEQ ID NO:3, and in SEQ ID NO:5, under various conditions of stringency. Hybridisation conditions are based on the melting temperature (Tm) of the nucleic acid binding complex or probe, as taught in Wahl, G. M. and S. L. Berger (1987: Methods Enzymol. 152:399–407) and Kimmel, A. R. (1987; Methods Enzymol. 152:507–511), and may be used at a defined stringency. Preferably, hybridization under stringent conditions means that after washing for 1 h with 1×SSC and 0.1% SDS at 50° C., preferably at 55° C., more preferably at 62° C. and most preferably at 68° C., particularly for 1 h in 0.2×SSC and 0.1% SDS at 50° C., preferably at 55° C., more preferably at 62° C. and most preferably at 68° C., a positive hybridization signal is observed. Altered nucleic acid sequences encoding DevG20, DevG4, or DevG22 which are encompassed by the invention include deletions, insertions, or substitutions of different nucleotides resulting in a polynucleotide that encodes the same or a functionally equivalent protein.

The encoded proteins may also contain deletions, insertions, or substitutions of amino acid residues, which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the biological activity of DevG20, DevG4, or DevG22 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding DevG20, DevG4, or DevG22. As used herein, an "allele" or "allelic sequence" is an alternative form of the gene, which may result from at least one mutation in the nucleic acid sequence. Alleles may result in altered mRNAs or polypeptides whose structures or function may or may not be altered. Any given gene may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence. Methods for DNA sequencing which are well known and generally available in the art may be used to practice any embodiments of the invention. The methods may employ such enzymes as the Klenow fragment of DNA polymerase I, SEQUENASE DNA Polymerase (US Bio-chemical Corp, Cleveland Ohio), Taq polymerase (Perkin Elmer), thermostable T7 polymerase (Amersham, Chicago, Ill.), or combinations of recombinant polymerases and proof-reading exonucleases such as the ELONGASE Amplification System (GIBCO/BRL, Gaithersburg, Md.). Preferably, the process is automated with machines such as the Hamilton MICROLAB 2200 (Hamilton, Reno Nev.), Peltier thermal cycler (PTC200; MJ Research, Watertown, Mass.) and the ABI 377 DNA sequencers (Perkin Elmer). The nucleic acid sequences encoding DevG20, DevG4, or DevG22 may be extended utilising a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase. Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to 22–30 nucleotides in length, to have a GC content of 50% or more, and to anneal to the target sequence temperatures about 68–72° C. The method uses several restriction enzymes to generate suitable fragments. The fragment is then circularised by intramolecular ligation and used as a PCR template.

Another method which may be used is capture PCR which involves PCR amplification of DNA fragments adjacent to a known sequence in human and yeast artificial chromosome DNA (Lagerstrom, M. et al. (PCR Methods Applic. 1:111–119). In this method, multiple restriction enzyme digestions and ligations also are used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences, which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions. Capillary electrophoresis systems, which are commercially available, may be used to analyse the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA, which might be present in limited amounts in a particular sample.

In another embodiment of the invention, polynucleotide sequences which encode DevG20, DevG4, or DevG22 or fragments thereof, or fusion proteins or functional equivalents thereof, may be used in recombinant DNA molecules to direct expression of DevG20, DevG4, or DevG22 in appropriate host cells. Due to the inherent degeneracy of the genetic code, other DNA sequences, which encode substantially the same, or a functionally equivalent amino acid sequence may be produced and these sequences may be used to clone and express DevG20, DevG4, or DevG22. As will be understood by those of skill in the art, it may be advantageous to produce DevG20-encoding, DevG4-encoding, and DevG22-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. The nucleotide sequences of the present invention can be engineered using methods generally known in the art in order to alter DevG20, DevG4, or DevG22 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding DevG20, DevG4, or DevG22 may be ligated to a heterologous sequence to encode a fusion protein. For example, to screen peptide libraries for inhibitors of DevG20, DevG4, or DevG22 activities, it may be useful to produce chimeric proteins that can be recognised by a commercially available antibodies. A fusion protein may also be engineered to contain a cleavage site located between the DevG20, DevG4, or DevG22 encoding sequence and the heterologous protein sequences, so that DevG20, DevG4, or DevG22 may be cleaved and purified away from the heterologous moiety. In another embodiment, sequences encoding DevG20, DevG4, or DevG22 may be synthesised, in whole or in part, using chemical methods well known in the art (see Caruthers, M. H. et al. (1980) Nucl. Acids Res. Symp. Ser. 7:215–223, Horn, T. et al. (1980) Nucl. Acids Res. Symp. Ser. 7:225–232). Alternatively, the proteins themselves may be produced using chemical methods by synthesising the amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesiser (Perkin Elmer). The newly synthesised peptide may be substantially purified by preparative high performance liquid chromatography (e.g., Creighton, T. (1983) Proteins, Structures and Molecular Principles, WH Freeman and Co., New York, N.Y.). The composition of the synthetic peptides may be confirmed by amino acid analysis or sequencing (e.g., the Edman degradation procedure; Creighton, supra). Additionally, the amino acid sequences, or any part thereof, may be altered during direct synthesis and/or combined using chemical methods with sequences from other proteins, or any part thereof, to produce a variant polypeptide.

In order to express a biologically active DevG20, DevG4, or DevG22, the nucleotide sequences coding therefor or functional equivalents, may be inserted into appropriate expression vectors, i.e., a vector, which contains the necessary elements for the transcription and translation of the inserted coding sequence. Methods, which are well known to those skilled in the art, may be used to construct expression vectors and appropriate transcriptional and translational control elements. These methods include in vitro recombinant DNA techniques. synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilised to contain and express sequences encoding DevG20, DevG4, or DevG22. These include, but are not limited to, micro-organisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or PBR322 plasmids); or animal cell systems. The "control elements" or "regulatory sequences" are those non-translated regions of the vector-enhancers, promoters, 5' and 3' untranslated regions which interact with host cellular proteins to carry out transcription and translation. Such elements may vary in their strength and specificity. Depending on the vector system and host utilised, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters and enhancers derived from the genomes of plant cells (e.g., heat shock, RUBISCO; and storage protein genes) or from plant viruses (e.g., viral promoters and leader sequences) may be cloned into the vector. In mammalian cell systems, promoters from mammalian genes or from mammalian viruses are preferable. If it is necessary to generate a cell line that contains multiple copies of the sequences, vectors based on SV40 or EBV may be used with an appropriate selectable marker.

In bacterial systems, a number of expression vectors may be selected depending upon the use intended for the protein. For example, when large quantities of protein are needed for the induction of antibodies, vectors, which direct high level expression of fusion proteins that are readily purified, may be used. Such vectors include, but are not limited to, the multifunctional *E. coli* cloning and expression vectors such as the BLUESCRIPT phagemid (Stratagene), in which the sequence encoding DevG20, DevG4, or DevG22 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem.

264:5503–5509); and the like. PGEX vectors (Promega, Madison, Wis.) may also be used to express foreign polypeptides as fusion proteins with Glutathione S-Transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will. In the yeast, Saccharomyces cerevisiae, a number of vectors containing constitutive or inducible promoters such as alpha factor, alcohol oxidase, and PGH may be used. For reviews, see Ausubel et al., (supra) and Grantet al. (1987) Methods Enzymol. 153:516–544.

In cases where plant expression vectors are used, the expression of sequences encoding DevG20, DevG4, or DevG22 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express DevG20, DevG4, or DevG22. For example, in one such system, Autographa californica nuclear polyhedrosis virus (Ac-NPV) is used as a vector to express foreign genes in Spodoptera frugiperda cells or in Trichoplusia larvae. The sequences may be cloned into a non-essential region of the virus, such as the polyhedrin gene, and place under control of the polyhedrin promoter. Successful insertions will render the polyhedrin gene inactive and produce recombinant virus lacking coat protein. The recombinant viruses may then be used to infect, for example, S. frugiperda cells of Trichoplusia larvae in which DevG20, DevG4, or DevG22 may be expressed (Engelhard, E. K. et al. (1994) Proc. Nat. Acad. Sci. 91:3224–3227).

In mammalian host cells, a number of viral-based expression systems may be utilised. In cases where an adenovirus is used as an expression vector, sequences encoding DevG20, DevG4, or DevG22 may be ligated into an adenovirus transcription/translation complex consisting of the late promoter and tripartite leader sequence. Insertion in a non-essential E1 or E3 region of the viral genome may be used to obtain viable viruses which are capable of expression in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation. Such signals include the ATG initiation codon and adjacent sequences. In cases where sequences encoding DevG20, DevG4, or DevG22, initiation codons, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a “prepro” form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express DevG20, DevG4, or DevG22 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells, which successfully express the introduced sequences. Resistant clones of stably transformed cells may be proliferated using tissue culture techniques appropriate to the cell type. Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes, which can be employed in tk- or aprt-, cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilise indole in place of tryptophan, or hisD, which allows cells to utilise histinol in place of histidine (Hartman, S. C. and R. C. Mulligan (1988) Proc. Natl. Acad. Sci. 85:8047–51). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequences encoding DevG20, DevG4, or DevG22 are inserted within a marker gene sequence, recombinant cells containing sequences encoding DevG20, DevG4, or DevG22 can be identified by the absence of marker gene function. Alternatively, a marker gene can be placed in tandem with sequences encoding DevG20, DevG4, or DevG22 under the control of a single promoter. Expression of the marker gene in response to induction or selection usually indicates expression of the tandem gene as well. Alternatively, host cells, which contain and express the nucleic acid sequences encoding DevG20, DevG4, or DevG22, may be identified by a variety of procedures known to those of skill in the art. These procedures include, but are not limited to, DNA-DNA, or DNA-RNA hybridisation and protein bioassay or immunoassay techniques which include membrane, solution, or chip based technologies for the detection and/or quantification of nucleic acid or protein.

The presence of polynucleotide sequences encoding DevG20, DevG4, or DevG22 can be detected by DNA-DNA or DNA-RNA hybridisation or amplification using probes or portions or fragments of polynucleotides specific for DevG20, DevG4, or DevG22. Nucleic acid amplification based assays involve the use of oligonucleotides or oligomers based on the sequences specific for DevG20, DevG4, or DevG22 to detect transformants containing DNA or RNA encoding DevG20, DevG4, or DevG22. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of DevG20, DevG4, or DevG22, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilising monoclonal antibodies reactive to two non-interfering epitopes on the protein is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labelled hybridisation or PCR probes for detecting sequences related to polynucleotides encoding DevG20, DevG4, or DevG22 include oligo-labelling, nick translation, end-labelling or PCR amplification using a labelled nucleotide.

Alternatively, the sequences encoding DevG20, DevG4, or DevG22, or any portions thereof may be cloned into a vector for the production of an mRNA probe. Such vectors are known in the art, are commercially available, and may be used to synthesise RNA probes in vitro by addition of an appropriate RNA polymerase such as T7, T3, or SP6 and labelled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio).

Suitable reporter molecules or labels, which may be used, include radionuclides, enzymes, fluorescent, chemiluminescent, or chromogenic agents as well as substrates, co-factors, inhibitors, magnetic particles, and the like.

Host cells transformed with nucleotide sequences encoding DevG20, DevG4, or DevG22 may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors may be designed to contain signal sequences, which direct secretion of proteins through a prokaryotic or eukaryotic cell membrane. Other recombinant constructions may be used to join sequences encoding DevG20, DevG4, or DevG22 to nucleotide sequences encoding a polypeptide domain, which will facilitate purification of soluble proteins. Such purification facilitating domains include, but are not limited to, metal chelating peptides such as histidine-tryptophan modules that allow purification on immobilised metals, protein A domains that allow purification on immobilised immunoglobulin, and the domain utilised in the FLAG extension/affinity purification system (Immunex Corp., Seattle, Wash.) The inclusion of cleavable linker sequences such as those specific for Factor XA or Enterokinase (Invitrogen, San Diego, Calif.) between the purification domain and the desired protein may be used to facilitate purification. One such expression vector provides for expression of a fusion protein containing DevG20, DevG4, or DevG22 and a nucleic acid encoding 6 histidine residues preceding a Thioredoxine or an Enterokinase cleavage site. The histidine residues facilitate purification on IMIAC (immobilised metal ion affinity chromatography as described in Porath, J. et al. (1992, Prot. Exp. Purif. 3: 263–281)) while the Enterokinase cleavage site provides a means for purifying DevG20, DevG4, or DevG22 from the fusion protein. A discussion of vectors which contain fusion proteins is provided in Kroll, D. J. et al. (1993; DNA Cell Biol. 12:441–453). In addition to recombinant production, fragments of DevG20, DevG4, or DevG22 may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A peptide synthesiser (Perkin Elmer). Various fragments of DevG20, DevG4, or DevG22 may be chemically synthesised separately and combined using chemical methods to produce the full length molecule.

Diagnostics and Therapeutics

The data disclosed in this invention show that the nucleic acids and proteins of the invention are useful in diagnostic and therapeutic applications implicated, for example but not limited to, in metabolic disorders like obesity, as well as related disorders such as adipositas, eating disorders, wasting syndromes (cachexia), pancreatic dysfunctions (such as diabetes mellitus), hypertension, pancreatic dysfunctions, arteriosclerosis, coronary artery disease (CAD), coronary heart disease, hypercholesterolemia, dyslipidemia, osteoarthritis, gallstones, cancer, e.g. cancers of the reproductive organs, sleep apnea, and other diseases and disorders. Hence, diagnostic and therapeutic uses for the DevG20, DevG4, or DevG22 proteins of the invention are, for example but not limited to, the following: (i) protein therapeutic, (ii) small molecule drug target, (iii) antibody target (therapeutic, diagnostic, drug targeting/cytotoxic antibody), (iv) diagnostic and/or prognostic marker, (v) gene therapy (gene delivery/gene ablation), (vi) research tools, and (vii)

tissue regeneration in vitro and in vivo (regeneration for all these tissues and cell types composing these tissues and cell types derived from these tissues).

The nucleic acids and proteins of the invention are useful in diagnositic and therapeutic applications implicated in various diseases and disorders described below and/or other pathologies and disorders. For example, but not limited to, cDNAs encoding the proteins of the invention and particularly their human homologues may be useful in gene therapy, and the DevG20, DevG4, or DevG22 proteins of the invention and particularly their human homologues may be useful when administered to a subject in need thereof. By way of non-limiting example, the compositions of the present invention will have efficacy for treatment of patients suffering from, for example, but not limited to, in metabolic disorders like obesity, as well as related disorders such as adipositas, eating disorders, wasting syndromes (cachexia), pancreatic dysfunctions (such as diabetes mellitus), hypertension, arteriosclerosis, coronary heart disease, hypercholesterolemia, dyslipidemia, osteoarthritis, gallstones, cancer, e.g. cancers of the reproductive organs, sleep apnea, and other diseases and disorders.

The nucleic acid encoding the DevG20, DevG4, or DevG22 protein of the invention, or fragments thereof, may further be useful in diagnostic applications, wherein the presence or amount of the nucleic acids or the proteins are to be assessed. These materials are further useful in the generation of antibodies that bind immunospecifically to the novel substances of the invention for use in therapeutic or diagnostic methods.

For example, in one aspect, antibodies which are specific for DevG20, DevG4, or DevG22 may be used directly as an antagonist, or indirectly as a targeting or delivery mechanism for bringing a pharmaceutical agent to cells or tissue which express DevG20, DevG4, or DevG22. The antibodies may be generated using methods that are well known in the art. Such antibodies may include, but are not limited to, polyclonal, monoclonal, chimerical, single chain, Fab fragments, and fragments produced by a Fab expression library. Neutralising antibodies, (i.e., those which inhibit dimer formation) are especially preferred for therapeutic use.

For the production of antibodies, various hosts including goats, rabbits, rats, mice, humans, and others, may be immunised by injection with DevG20, DevG4, or DevG22 or any fragment or oligopeptide thereof which has immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. Among adjuvants used in human, BCG (Bacille Calmette-Guerin) and *Corynebacterium parvum* are especially preferable. It is preferred that the peptides, fragments, or oligopeptides used to induce antibodies have an amino acid sequence consisting of at least five amino acids, and more preferably at least 10 amino acids. It is preferable that they are identical to a portion of the amino acid sequence of the natural protein, and they may contain the entire amino acid sequence of a small, naturally occurring molecule. Short stretches of amino acids may be fused with those of another protein such as keyhole limpet hemocyanin in order to enhance the immunogenicity.

Monoclonal antibodies to DevG20, DevG4, or DevG22 may be prepared using any technique which provides for the production of antibody molecules by continuous cell lines in culture. These include, but are not limited to, the hybridoma technique, the human B-cell hybridoma technique, and the EBV-hybridoma technique (Köhler, G. et al. (1975) Nature 256:495–497; Kozbor, D. et al. (1985) J. Immunol. Methods 81:31–42; Cote, R. J. et al. Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al (1984) Nature 312: 604–608; Takeda, S. et al. (1985) Nature 314:452–454). Alternatively, techniques described for the production of single chain antibodies may be adapted, using methods known in the art, to produce single chain antibodies. Antibodies with related specificity, but of distinct idiotypic composition, may be generated by chain shuffling from random combinatorial immunoglobulin libraries (Burton, D. R. (1991) Proc. Natl. Acad. Sci. 88:11120–3). Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments, which contain specific binding sites for DevG20, DevG4, or DevG22, may also be generated. For example, such fragments include, but are not limited to, the F(ab')$_2$ fragments which can be produced by Pepsin digestion of the antibody molecule and the Fab fragments which can be generated by reducing the disulfide bridges of F(ab')$_2$ fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding and immunoradiometric assays using either polyclonal or monoclonal antibodies with established specificities are well known in the art. Such immunoassays typically involve the measurement of complex formation between the protein and its specific antibody. A two-site, monoclonal-based immunoassay utilising monoclonal antibodies reactive to two non-interfering epitopes is preferred, but a competitive binding assay may also be employed (Maddox, supra).

In another embodiment of the invention, the polynucleotides encoding DevG20, DevG4, or DevG22, or any fragment thereof, or antisense molecules, may be used for therapeutic purposes. In one aspect, antisense molecules may be used in situations in which it would be desirable to block the transcription of the mRNA. In particular, cells may be transformed with sequences complementary to polynucleotides encoding DevG20, DevG4, or DevG22. Thus, antisense molecules may be used to modulate protein activity, or to achieve regulation of gene function. Such technology is now well know in the art, and sense or antisense oligomers or larger fragments, can be designed from various locations along the coding or control regions of sequences encoding DevG20, DevG4, or DevG22. Expression vectors derived from retroviruses, adenovirus, herpes or vaccinia viruses, or from various bacterial plasmids may be used for delivery of nucleotide sequences to the targeted organ, tissue or cell population. Methods, which are well known to those skilled in the art, can be used to construct recombinant vectors, which will express antisense molecules complementary to the polynucleotides of the gene encoding DevG20, DevG4, or DevG22. These techniques are described both in Sambrook et al. (supra) and in Ausubel et al. (supra). Genes encoding DevG20, DevG4, or DevG22 can be turned off by transforming a cell or tissue with expression vectors which express high levels of polynucleotide or fragment thereof which encodes DevG20, DevG4, or DevG22. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, e.g. DNA, RNA, or PNA molecules, to the control regions of the genes encoding DevG20, DevG4, or DevG22, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it cause inhibition of the ability of the double helix to open sufficiently for the binding of polymerases, transcription factors, or regulatory molecules. Recent therapeutic advances using triplex DNA have been described in the literature (Gee, J. E. et al. (1994) In; Huber, B. E. and B. I. Carr, Molecular and Immunologic Approaches, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyse the specific cleavage of RNA. The mechanism of ribozyme action involves sequence-specific hybridisation of the ribozyme molecule to complementary target RNA, followed by endonucleolytic cleavage. Examples, which may be used, include engineered hammerhead motif ribozyme molecules that can be specifically and efficiently catalyse endonucleolytic cleavage of sequences encoding DevG20, DevG4, or DevG22. Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridisation with complementary oligonucleotides using ribonuclease protection assays.

Antisense molecules and ribozymes of the invention may be prepared by any method known in the art for the synthesis of nucleic acid molecules. These include techniques for chemically synthesising oligonucleotides such as solid phase phosphoramidite chemical synthesis. Alternatively, RNA molecules may be generated by in vitro and in vivo transcription of DNA sequences encoding DevG20, DevG4, or DevG22. Such DNA sequences may be incorporated into a variety of vectors with suitable RNA polymerase promoters such as T7 or SP6. Alternatively, these cDNA constructs that synthesise antisense RNA constitutively or inducibly can be introduced into cell lines, cells, or tissues. RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of non-traditional bases such as inosine, queosine, and wybutosine, as well as acetyl-, methyl-, thio-, and similarly modified forms of adenine, cytidine, guanine, thymine, and uridine which are not as easily recognised by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods, which are well known in the art. Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of DevG20, DevG4, or DevG22, antibodies to DevG20, DevG4, or DevG22, mimetics, agonists, antagonists, or inhibitors of DevG20, DevG4, or DevG22. The compositions may be administered alone or in combination with at least one other agent, such as stabilising compound, which may be administered in any sterile, biocompatible pharmaceutical carrier, including, but not limited to, saline, buffered saline, dextrose, and water. The compositions may be administered to a patient alone, or in combination with other agents, drugs or hormones. The pharmaceutical compositions utilised in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries, which facilitate processing of the active compounds into preparations which, can be used pharmaceutically. Further details on techniques for formulation and administration may be found in the latest edition of Remington's Pharmaceutical Sciences (Maack Publishing Co., Easton, Pa.). Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including Arabic and tragacanth; and proteins such as gelatine and collagen. If desired, disintegrating or solubilising agents may be added, such as the cross-linked polyvinyl pyrrolidone, agar, alginic acid, or a salt thereof, such as sodium alginate. Dragee cores may be used in conjunction with suitable coatings, such as concentrated sugar solutions, which may also contain gum Arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coating for product identification or to characterise the quantity of active compound, i.e., dosage. Pharmaceutical preparations, which can be used orally, include push-fit capsules made of gelatine, as well as soft, sealed capsules made of gelatine and a coating, such as glycerol or sorbitol. Push-fit capsules can contain active ingredients mixed with a filler or binders, such as lactose or starches, lubricants, such as talc or magnesium stearate, and, optionally, stabilisers. In soft capsules, the active compounds may be dissolved or suspended in suitable liquids, such as fatty oils, liquid, or liquid polyethylene glycol with or without stabilisers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilisers or agents who increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilising processes. The pharmaceutical composition may be provided as a salt and can be formed with many acids, including but not limited to, hydrochloric, sulphuric, acetic, lactic, tartaric, malic, succinic, etc. Salts tend to be more soluble in aqueous or other protonic solvents than are the corresponding free base forms. In other cases, the preferred preparation may be a lyophilised powder which may contain any or all of the following: 1–50 mM histidine, 0.1%–2% sucrose, and 2–7% mannitol, at a pH range of 4.5 to 5.5, that is combined with buffer prior to use. After pharmaceutical compositions have been prepared, they can be placed in an appropriate container and labelled for treatment of an indicated condition. For administration of DevG20, DevG4, or DevG22, such labelling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art. For any compounds, the therapeutically effective does can be estimated initially either in cell culture assays, e.g., of preadipocyte cell lines, or in animal models, usually mice, rabbits, dogs, or pigs. The animal model may also be used to determine the appropriate concentration range and route of administration. Such information can then be used to determine useful doses and routes for administration in humans. A therapeutically effective dose refers to that amount of active ingredient, for example DevG20, DevG4, or DevG22 or fragments thereof, antibodies of DevG20, DevG4, or DevG22, to treat a specific condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage from employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy.

Long-acting pharmaceutical compositions may be administered every 3 to 4 days, every week, or once every two weeks depending on half-life and clearance rate of the particular formulation. Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art employ different formulations for nucleotides than for proteins or their inhibitors. Similarly, delivery of polynucleotides or polypeptides will be specific to particular cells, conditions, locations, etc.

In another embodiment, antibodies which specifically bind DevG20, DevG4, or DevG22 may be used for the diagnosis of conditions or diseases characterised by or associated with over- or underexpression of DevG20, DevG4, or DevG22, or in assays to monitor patients being treated with DevG20, DevG4, or DevG22, agonists, antagonists or inhibitors. The antibodies useful for diagnostic purposes may be prepared in the same manner as those described above for therapeutics. Diagnostic assays include methods, which utilise the antibody and a label to detect DevG20, DevG4, or DevG22 in human body fluids or extracts of cells or tissues. The antibodies may be used with or without modification, and may be labelled by joining them, either covalently or non-covalently, with a reporter molecule. A wide variety of reporter molecules which are known in the art may be used several of which are described above.

A variety of protocols including ELISA, RIA, and FACS for measuring DevG20, DevG4, or DevG22 are known in the art and provide a basis for diagnosing altered or abnormal levels of gene expression. Normal or standard values for expression are established by combining body fluids or cell extracts taken from normal mammalian subjects, preferably human, with antibodies to DevG20, DevG4, or DevG22 under conditions suitable for complex formation. The amount of standard complex formation may be quantified by various methods, but preferably by photometry, means. Quantities of DevG20, DevG4, or DevG22 expressed in control and disease, samples from biopsied tissues are compared with the standard values. Deviation between standard and subject values establishes the parameters for diagnosing disease.

In another embodiment of the invention, the polynucleotides specific for DevG20, DevG4, or DevG22 may be used for diagnostic purposes. The polynucleotides, which may be used, include oligonucleotide sequences, antisense RNA and DNA molecules, and PNAs. The polynucleotides may be used to detect and quantitate gene expression in biopsied tissues in which expression of DevG20, DevG4, or DevG22 may be correlated with disease. The diagnostic assay may be used to distinguish between absence, presence, and excess expression, and to monitor regulation of gene expression levels during therapeutic intervention.

In one aspect, hybridisation with PCR probes which are capable of detecting polynucleotide sequences, including genomic sequences, encoding DevG20, DevG4, or DevG22 or closely related molecules, may be used to identify nucleic acid sequences which encode DevG20, DevG4, or DevG22. The specificity of the probe, whether it is made from a highly specific region, e.g., unique nucleotides in the 5' regulatory region, or a less specific region, e.g., especially in the 3' coding region, and the stringency of the hybridisation or amplification (maximal, high, intermediate, or low) will determine whether the probe identifies only naturally occurring sequences encoding DevG20, DevG4, or DevG22, alleles, or related sequences. Probes may also be used for the detection of related sequences, and should preferably contain at least 50% of the nucleotides from any of the DevG20, DevG4, or DevG22 encoding sequences. The hybridisation probes of the subject invention may be DNA or RNA and derived from the nucleotide sequence of SEQ ID NO:1, SEQ ID NO:3 or SEQ ID NO:5 or from a genomic sequence including promoter, enhancer elements, and introns of the naturally occurring DevG20, DevG4, or DevG22 gene. Means for producing specific hybridisation probes for DNAs encoding DevG20, DevG4, or DevG22 include the cloning of nucleic acid sequences encoding DevG20, DevG4, or DevG22 or derivatives thereof into vectors for the production of mRNA probes. Such vectors are known in the art, commercially available, and may be used to synthesise RNA probes in vitro by means of the addition of the appropriate RNA polymerases and the appropriate labelled nucleotides. Hybridisation probes may be labelled by a variety of reporter groups, for example, radionuclides such as $^{32}P$ or $^{35}S$, or enzymatic labels, such as alkaline phosphatase coupled to the probe via avidin/biotin coupling systems, and the like.

Polynucleotide sequences specific for DevG20, DevG4, or DevG22 may be used for the diagnosis of conditions or diseases, which are associated with expression of DevG20, DevG4, or DevG22. Examples of such conditions or diseases include, but are not limited to, pancreatic diseases and disorders, including diabetes. Polynucleotide sequences specific for DevG20, DevG4, or DevG22 may also be used to monitor the progress of patients receiving treatment for pancreatic diseases and disorders, including diabetes. The polynucleotide sequences may be used in Southern or Northern analysis, dot blot, or other membrane-based technologies; in PCR technologies; or in dip stick, pin, ELISA or chip assays utilising fluids or tissues from patient biopsies to detect altered gene expression. Such qualitative or quantitative methods are well known in the art.

In a particular aspect, the nucleotide sequences encoding DevG20, DevG4, or DevG22 may be useful in assays that detect activation or induction of various metabolic diseases and disorders, including obesity, as well as related disorders such as described above. The nucleotide sequences may be labelled by standard methods, and added to a fluid or tissue sample from a patient under conditions suitable for the formation of hybridisation complexes. After a suitable incubation period, the sample is washed and the signal is quantitated and compared with a standard value. If the amount of signal in the biopsied or extracted sample is significantly altered from that of a comparable have hybridised with nucleotide sequences in the sample, and the presence of altered levels of nucleotide sequences in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of DevG20, DevG4, or DevG22, a normal or standard profile for expression is established. This may be accomplished by combining body fluids or cell extracts taken from normal subjects, either animal or human, with a sequence, which is specific for DevG20, DevG4, or DevG22, under conditions suitable for hybridisation or amplification. Standard hybridisation may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease. Once disease is established and a treatment protocol is initiated, hybridisation assays may be repeated on a regular basis to evaluate whether the level of expression in the patient begins to approximate that, which is observed in the normal patient. The results obtained from successive assays may be used to show the efficacy of treatment over a period ranging from several days to months.

With respect to metabolic diseases and disorders, including obesity, as well as related disorders such as adipositas, eating disorders, wasting syndromes (cachexia), pancreatic dysfunctions (such as diabetes mellitus), hypertension, arteriosclerosis, coronary heart disease, hypercholesterolemia, dyslipidemia, osteoarthritis, gallstones, cancer, e.g. cancers of the reproductive organs, sleep apnea, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the pancreatic diseases and disorders. Additional diagnostic uses for oligonucleotides designed from the sequences encoding DevG20, DevG4, or DevG22 may involve the use of PCR. Such oligomers may be chemically synthesised, generated enzymatically, or produced from a recombinant source. Oligomers will preferably consist of two nucleotide sequences, one with sense orientation (5'.fwdarw.3') and another with antisense (3'.rarw.5'), employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

Methods which may also be used to quantitate the expression of DevG20, DevG4, or DevG22 include radiolabelling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantification of multiple samples may be accelerated by running the assay in an ELISA format where the oligomer of interest is presented in various dilutions and a spectrophotometric or colorimetric response gives rapid quantification.

In another embodiment of the invention, the nucleic acid sequences, which are specific for DevG20, DevG4, or DevG22, may also be used to generate hybridisation probes, which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154. FISH (as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding DevG20, DevG4, or DevG22 on a physical chromosomal map and a specific disease, or predisposition to a specific disease, may help to delimit the region of DNA associated with that genetic disease.

The nucleotide sequences of the subject invention may be used to detect differences in gene sequences between normal, carrier, or affected individuals. In situ hybridisation of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localised by genetic linkage to a particular genomic region, for example, AT to 11 q22–23 (Gatti, R. A. et al. (1988) Nature 336:577–580), any sequences mapping to that area may represent associated or regulatory genes for further investigation. The nucleotide sequences of the subject invention may also be used to detect differences in the chromosomal location due to translocation, inversion, etc. among normal, carrier, or affected individuals.

In another embodiment of the invention, DevG20, DevG4, or DevG22, their catalytic or immunogenic fragments or oligopeptides thereof, can be used for screening libraries of compounds, e.g. peptides or low-molecular weight organic molecules, in any of a variety of drug screening techniques. The fragment employed in such screening may be free in solution, affixed to a solid support, borne on a cell surface, or located intracellularly. The formation of binding complexes, between the protein and the agent tested, may be measured.

Another technique for drug screening, which may be used, provides for high throughput screening of compounds having suitable binding affinity to the protein of interest as described in published PCT application WO84/03564. In this method, as applied to DevG20, DevG4, or DevG22 large numbers of different test compounds, e.g. small molecules, are synthesised on a solid substrate, such as plastic pins or some other surface. The test compounds are reacted with the proteins, or fragments thereof, and washed. Bound proteins are then detected by methods well known in the art. Purified proteins can also be coated directly onto plates for use in the aforementioned drug screening techniques. Alternatively, non-neutralising antibodies can be used to capture the peptide and immobilise it on a solid support. In another embodiment, one may use competitive drug screening assays in which neutralising antibodies capable of binding DevG20, DevG4, or DevG22 specifically compete with a test compound for binding DevG20, DevG4, or DevG22. In this manner, the antibodies can be used to detect the presence of any peptide, which shares one or more antigenic determinants with DevG20, DevG4, or DevG22. In additional embodiments, the nucleotide sequences which encode DevG20, DevG4, or DevG22 may be used in any molecular biology techniques that have yet to be developed, provided the new techniques rely on properties of nucleotide that are currently known, including, but not limited to, such properties as the triplet genetic code and specific base pair interactions.

THE FIGURES SHOW

FIG. 1 shows the average increase of starvation resistance of HD-EP(X) 10478 and HD-EP(X)31424 flies (*Drosophila melanogaster*; in the Figure, referred to as 10478 and 31424) by ectopic expression using 'FB- or elav-Gal4 driver' (in comparison to wildtype flies (Oregon R); FB stands for fat body; elav-Gal4 stands for elevated Gal4). The average values for surviving flies (,average survivors) are given in % per time point (shown on the horizontal line as time of starvation; 8 hours (8 h) to 72 hours (72 h)) are shown. See Examples for a more detailed description.

FIG. 2 shows the increase of triglyceride content of HD-EP(X)10478 and HD-EP(X)31424 flies by ectopic expression using "FB- or elav-Gal4 driver" (in comparison to wildtype flies (Oregon R)). Standard deviation of the measurements is shown as thin bars. Triglyceride content of the fly populations is shown in ug/mg wet weight (wt) of a fly (vertical).

FIG. 3 shows the molecular organisation of the DevG20 locus.

FIG. 4A shows the nucleic acid sequence (SEQ ID NO:7) encoding the *Drosophila* DevG20 protein.

FIG. 4B shows the protein sequence (SEQ ID NO:8) of the *Drosophila* DevG20 encoded by the nucleic acid sequence shown in FIG. 4A.

FIG. 4C shows the nucleic acid sequence (SEQ ID NO:1) of the human DevG20 homolog protein encoding the *Homo sapiens* hypothetical protein with Genbank Accession Number NM_030810.1 (MGC3178).

FIG. 4D shows the human DevG20 protein sequence (SEQ ID NO:2) (GenBank Accession Number NP_110437.1) encoded by the nucleic acid sequence shown in FIG. 4C.

Figure 12:
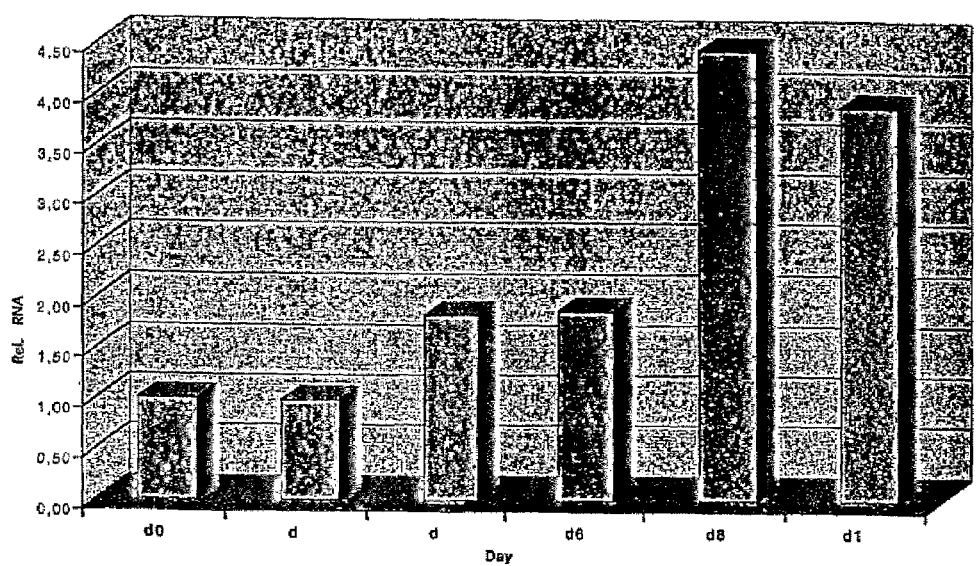

FIG. 5 shows the BLASTP (versus the non-redundant composite database) identity search result for *Drosophila* DevG20 protein (SEQ ID NO:8) and the human DevG20 protein (SEQ ID NO:2; GenBank Accession Number NP_110437.1), referred to as hG20 in the Figure. The middle sequence of the alignment shows identical amino acids in the one-letter code and conserved as +. Gaps in the alignment are represented as –.

FIG. 6 shows the expression of DevG20 in mammalian tissues.

FIG. 6A shows the real-time PCR analysis of DevG20-like expression in different wildtype mouse tissues. The relative RNA-expression is shown on the left hand side, the tissues tested are given on the horizontal line (for example, pancreas ('pancre'), white adipose tissue ('WA'), brown adipose tissue ('BA'), muscle ('muscl'), liver ('liv'), hypothalamus ('hypothalam'), cerebellum ('cerebell'), cortex ('corte'), midbrain ('midbra'); small intestine ('s. intestine'), heart ('hear'), lung ('lun'), spleen ('splee'), kidney ('kidne'), and bone marrow ('b. marrow').

FIG. 6B shows the real-time PCR analysis of DevG20-like expression in different mouse models (wildtype mice ('wt')— bars with light grey shading; fasted mice—bars with dark grey shading, obese mice ('ob/ob'), white bar) in different tissues (white adipose tissue ('WA'), brown adipose tissue ('BA'), muscle ('musc'), liver ('liv'), pancreas ('pancre'), hypothalamus ('hypothalam'), cerebellum ('cerebell'), cortex ('corte'), midbrain ('midbra'); small intestine ('s. intestine'), heart ('hear'), lung ('lun'), spleen ('splee'), kidney ('kidne'), and bone marrow ('b. marrow').

FIG. 6C shows the real-time PCR analysis of DevG20-like expression during the differentiation of 3T3-L1 cells from pre-adipocytes to mature adipocytes. The relative RNA-expression is shown on the left hand side, the days of differention are shown on the horizontal line (d0=day 0, start of the experiment, until d10=day 10).

FIG. 7 shows the relative increase of triglyceride content of EP(2)0646, EP(2)2188, and EP(2)2517 flies caused by homozygous viable integration of the P-vector (in comparison to wildtype flies (EP-control)). Standard deviation of the measurements is shown as thin bars. Triglyceride content of the fly populations is shown as ration TG/Protein content.

FIG. 8 shows the molecular organisation of the DevG4 gene locus.

FIG. 9A shows the nucleic acid sequence (SEQ ID NO:9) encoding the *Drosophila* DevG4 protein.

FIG. 9B shows the *Drosophila* DevG4 protein sequence (SEQ ID NO:10) encoded by the mRNA shown in FIG. 9A.

FIG. 9C shows the nucleic acid sequence (SEQ ID NO:3) encoding the human DevG4 homolog (*Homo sapiens* ATP-binding cassette, sub-family C (CFTR/MRP), member 4, also referred to as ABCC4 and MPR4; GenBank Accession Number NM_005845).

FIG. 9D shows the protein sequence (SEQ ID NO:4; GenBank Accession Number NP_005836.1) of the human DevG4 homolog.

FIG. 10 shows protein domains (black boxes) of the human DevG4 protein.

FIG. 11 shows the comparison of DevG4 protein domains of different species (human, hMRP4', mouse (only shown in FIG. 11D, mMRP4), and *Drosophila* (DevG4)). Gaps in the alignment are represented as –. The alignment was produced using the multisequence alignment program of Clustal V software (Higgins, D. G. and Sharp, P. M. (1989). CABIOS, vol. 5, no. 2, 151–153.).

(A) Alignment of the ABC-membrane I domains. The identity of amino acids of *Drosophila* DevG4 and human DevG4 (hMRP4) is 41% and the similarity 63%.

(B) Alignment of the ABC-tran I domains. The identity of amino acids of *Drosophila* DevG4 and human DevG4 (hMRP4) is 56% and the similarity 75%.

(C) Alignment of the ABC-membrane II domains. The identity of amino acids of *Drosophila* DevG4 and human DevG4 (hMRP4) is 42% and the similarity 60%.

(D) Alignment of the ABC-tran II domains. The identity of amino acids of *Drosophila* DevG4 and human DevG4 (hMRP4) is 69% and the similarity 86%. Human and mouse ABC-tran II are almost identical.

FIG. 12 shows the expression of DevG4 in mammalian tissues.

FIG. 12A shows the real-time PCR analysis of DevG4 (MRP4) expression in different wildtype mouse tissues (pancreas ('pancre'), white adipose tissue ('WA'), brown adipose tissue ('BA'), muscle ('muscl'), liver ('liv'), hypothalamus ('hypothalam'), cerebellum ('cerebell'), cortex ('corte'), midbrain ('midbra'); small intestine ('s. intestine'), heart ('hear'), lung ('lun'), spleen ('splee'), kidney ('kidne'), and bone marrow ('b. marrow'). The relative RNA-expression is shown on the left hand side, the tissues tested are given on the horizontal line.

FIG. 12B shows the real-time PCR analysis of DevG4 (MRP4) expression in different mouse models (wildtype mice ('wt'), fasted mice, obese mice ('ob/ob')) in different tissues (white adipose tissue ('WA'), brown adipose tissue ('BA'), muscle ('muscl'), liver ('liv'), pancreas ('pancre'), hypothalamus ('hypothalam'), cerebellum ('cerebell'), cortex ('corte'), midbrain ('midbra'); small intestine ('s. intestine'), heart ('hear'), lung ('lun'), spleen ('splee'), kidney ('kidne'), and bone marrow ('b. marrow').

FIG. 12C shows the real-time PCR analysis of DevG4 (MRP4) expression during the differentiation of 3T3-L1 cells from pre-adipocytes to mature adipocytes. The relative RNA-expression is shown on the left hand side, the days of differention are shown on the horizontal line (d0=day 0, start of the experiment, until d10=day 10).

FIG. 13 shows the relative increase of triglyceride content of HD-EP(2)20388 and EP(2)2482 flies caused by homozygous viable integration of the P-vector (in comparison to wildtype flies (EP-control)). Standard deviation of the measurements is shown as thin bars. Triglyceride content of the fly populations is shown as ratio TG/Protein content in percent (%).

FIG. 14 shows the molecular organisation of the DevG22 gene locus.

FIG. 15A shows the nucleic acid sequence (SEQ ID NO:11) encoding the *Drosophila* DevG22 protein.

FIG. 15B shows the protein sequence (SEQ ID NO:12) of the *Drosophila* DevG22 protein.

FIG. 15C shows the nucleic acid sequence (SEQ ID NO:5) encoding the human DevG22 homolog (*Homo sapiens* ATP-binding cassette, sub-family G (WHITE), member 1 protein; GenBank Accession Number XM_009777).

FIG. 15D shows the protein sequence (SEQ ID NO:6) of the human DevG22 homolog (*Homo sapiens* ATP-binding cassette, sub-family G (WHITE), member 1 protein; GenBank Accession Number XP_009777.3).

FIG. 16 shows protein domain (black box) of the DevG22 protein.

FIG. 17 shows the alignment of human, mouse and fly DevG22 proteins (White-like ABC transporters). White-like ABC transporters only have a single ABC-tran protein domain. *Drosophila* DevG22 is 36% identical and 52% similar to human DevG22 (hWhite; ABC8, ABCG1, GenBank Accession Number XM_009777). *Drosophila* DevG22 is 36% identical and 51% similar to mouse DevG22 (mWhite; GenBank Accession Number NP_033723). Human and mouse DevG22 proteins show 95% identity and 96% similarity.

Figure 18:
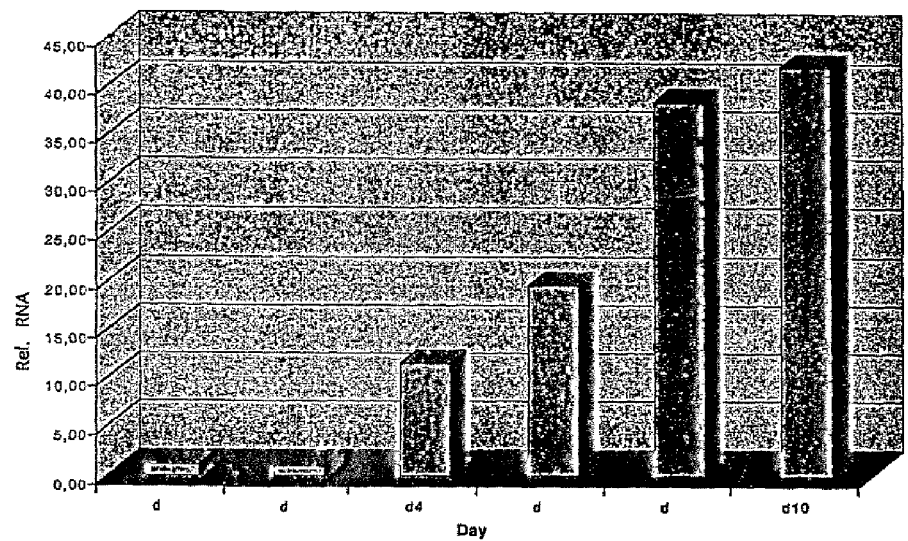

FIG. 18 shows the expression of DevG22 in mammalian tissues.

FIG. 18A shows the real-time PCR analysis of DevG22 expression in different wildtype mouse tissues (pancreas ('pancre'), white adipose tissue ('WA'), brown adipose tissue ('BA'), muscle ('muscl'), liver ('liv'), hypothalamus ('hypothalam'), cerebellum ('cerebell'), cortex ('corte'), midbrain ('midbra'); small intestine ('sm. testine'), heart ('hear'), lung ('lun'), spleen ('splee'), kidney ('kidne'), and bone marrow ('b. marrow').

FIG. 18B shows the real-time PCR analysis of DevG22 expression in different mouse models (wildtype mice ('wt'), fasted mice, obese mice ('ob/ob')) in different tissues (white adipose tissue ('WA'), brown adipose tissue ('BA'), muscle ('muscl'), liver ('liv'), pancreas ('pancre'), hypothalamus ('hypothalam'), cerebellum ('cerebell'), cortex ('corte'), midbrain ('midbra'); small intestine ('s. intestine'), heart ('hear'), lung ('lun'), spleen ('splee'), kidney ('kidne'), and bone marrow ('b. marrow').

FIG. 18C shows the real-time PCR analysis of DevG22 expression during the differentiation of 3T3-L1 cells from pre-adipocytes to mature adipocytes.

EXAMPLES

A better understanding of the present invention and of its many advantages will be evident from the following examples, only given by way of illustration.

Example 1

Isolation of EP-Lines That Have a Novel Function in Energy Homeostasis Using a Functional Genetic Screen In order to isolate genes with a function in energy homeostasis several thousand EP-lines were crossed against two "Gal4-driver" lines that direct expression of Gal4 in a tissue specific manner. Two different "driver"-lines were used in the screen: (i) expressing Gal4 mainly in the fatbody (FB), (ii) expressing Gal4 in neurons (elav) (FIG. 1). After crossing the "driver"-line to the EP-line, an endogenous gene may be activated in fatbody or neurons respectively. For selection of relevant genes affecting energy homeostasis, the offspring of that cross was exposed to starvation conditions after six days of feeding. Wildtype flies show a constant starvation resistance. EP-lines with significantly changed starvation resistance were selected as positive candidates.

Example 2

HD-EP(X)10478 and HD-EP(X)31424 Flies Show Significant Starvation Resistance When Driven in the Fatbody or Neurons Ectopic expression of the EP-lines HD-EP(X)10478 and HD-EP(X)31424, both homozygous viable integrations in the chromosomal region 10D4–10D6, under the control of the "FB-driver" and "elav-driver" caused a significant starvation resistance in comparison to wildtype flies (Oregon R, see FIG. 1). Hundred flies offfspring of a cross or line were analysed under starvation conditions. Survivors per time point are shown in FIG. 1. After 24 hours of starvation HD-EP(X)10478 and 31424 flies in combination with both "drivers" show 80–100% more survivors than the wildtype Oregon R. After 48 hours of starvation, almost no wildtype flies are still alive. In contrast, after 48 hours of starvation, about 20% of the population of HD-EP(X)10478 and 31424 in combination with both "drivers" are alive which is a significant increase. Few flies of HD-EP(X) 10478 and 31424 in combination with both "drivers" still survive after 72 hours of starvation where normally no wildtype flies are alive. Therefore, ectopic expression via HD-EP(X)10478 and HD-EP(X)31424 in the fatbody and neurons of *Drosophila melanogaster* leads to significant starvation resistance.

Example 3

Triglyceride Content is Increased by Ectopic Expression via HD-EP(X) 10478 and HD-EP(X)31424 in the Fatbody and Weaker in the Neurons Starvation resistance can have its origin due to changes in energy homeostasis, e.g., reduction of energy consumption and/or increase in storage of substances like triglycerides. Triglycerides are the most efficient storage for energy in cells. Therefore the content of triglycerides of a pool of flies with the same genotype was analysed using an triglyceride assay.

For determination of triglyceride content of flies, several aliquots of each time ten females of HD-EP(X)10478 and HD-EP(X)31424, HD-EP(X)10478/FB-Gal4 and HD-EP (X)31424/FB-Gal4, HD-EP(X)10478/elav-Gal4 and HD-EP (X)31424/elav-Gal4 and Oregon R were analysed. Flies were incubated for 5 min at 90° C. in an aqueous buffer using a waterbath, followed by hot extraction. After another 5 min incubation at 90° C. and mild centrifugation, the triglyceride content of the flies extract was determined using Sigma Triglyceride (INT 336-10 or -20) assay by measuring changes in the optical density according to the manufacturer's protocol. As a reference fly mass was measured on a fine balance before extraction procedure.

The result of the triglyceride contents analysis is shown in FIG. 2. The average increase of triglyceride content of HD-EP(X)10478 and 31424 flies in combination with the "FB- and elav Gal4-driver" lines is shown in comparison to wildtype flies (Oregon R) and the HD-EP(X)10478 and 31424 integrations alone. Standard deviations of the measurments are shown as thin bars. Triglyceride content of the different fly populations is shown in µg/mg wet weight (wt.) of a fly. In each assay ten females of the offspring of a cross or line were analysed in the triglyceride assay after feeding that offspring for six days. The assay was repeated several times. Wildtype flies show a constant triglyceride level of 30 to 45 µg/mg wet weight of a fly. HD-EP(X)10478 and 31424 flies show a similar or slightly lower triglyceride content than wildtype. In contrast, HD-EP(X)10478 and 31424 flies in combination with both "drivers" show an average increase up to 1.8-fold of 55 to 72 µg/mg wet wt. in comparison to wildtype (Oregon R) flies and the HD-EP(X) 10478 and 31424 integration alone. Therefore, gain of a gene activity in the locus 10D4-6 is responsible for changes in the metabolism of the energy storage triglycerides.

Ectopic expression of genomic *Drosophila* sequences using FB-Gal4 caused an average 1.8-fold increase of triglyceride content in comparison to wildtype flies (Oregon R).

HD-EP(X)10478 and HD-EP(X)31424 under the control of the "elav-Gal4-driver" caused a weaker increase of triglyceride content. Therefore ectopic expression via HD-EP(X) 10478 and HD-EP(X)31424 in the fatbody of Drosophila melanogaster leads to a significant increase of the energy storage triglyceride and therefore represents an obese fly model. The increase of triglyceride content by gain of a gene function suggests a gene activity in energy homeostasis in a dose dependent and tissue specific manner that controls the amount of energy stored as triglycerides.

Example 4

Measurement of Triglyceride Content of Homozygous Flies (EP(2)0646, EP(2)2188, EP(2)2517, HD-EP(2)20388, EP(2)2482)

Triglycerides are the most efficient storage for energy in cells. In order to isolate genes with a function in energy homeostasis, several thousand EP-lines were tested for their triglyceride content after a prolonged feeding period. Lines with significantly changed triglyceride content were selected as positive candidates for further analysis. In this invention, the content of triglycerides of a pool of flies with the same genotype after feeding for six days was analysed using a triglyceride assay. For determination of triglyceride content, several aliquots of each time 10 males of the offspring of a cross or line were analysed after feeding the offspring for six days. Fly mass was measured on a fine balance as a reference. Flies were extracted in methanol/chloroform (1:1) and an aliquot of the extract was evaporated under vacuum. Lipids were emulsified in an aqueous buffer with help of sonification. Triglyceride content was determined using Sigma INT 336-10 or -20 assay by measuring changes in the optical density according to the manufacturer's protocol.

Improving and simplifying the determination of triglyceride content of flies, In each assay ten males of the offspring of a cross or line were analysed in the triglyceride assay after feeding that offspring for six days; the assay was repeated several times. Flies were incubated for 5 min at 90° C. in an aqueous buffer using a waterbath, followed by hot extraction. After another 5 min incubation at 90° C. and mild centrifugation, the triglyceride content of the flies extract was determined using Sigma Triglyceride (INT 336-10 or -20) assay by measuring changes in the optical density according to the manufacturer's protocol. As a reference protein content of the same extract was measured using BIO-RAD DC Protein Assay according to the manufacturer's protocol.

Wildtype flies show constantly a triglyceride level of 11 to 23 µg/mg wet weight of a fly. EP(2)0646, EP(2)2188, EP(2)2517, and HD-EP(2)20388, and EP(2)2482 homozygous flies show constantly a higher triglyceride content than the wildtype (FIGS. 7 and 13). In contrast, EP(2)0646, EP(2)2188, EP(2)2517, HD-EP(2)20388, and EP(2)2482 flies in combination with both "drivers" show sometimes only a slightly increase (2.1- to 2.3-fold of 49 to 53 µg/mg wet wt) in comparison to the wildtype (Oregon R) (not shown). Therefore, the loss of gene activity in the loci, where the P-vector of EP(2)0646, EP(2)2188, EP(2)2517, HD-EP(2)20388, and EP(2)2482 flies is homozygous viably integrated, is responsible for changes in the metabolism of the energy storage triglycerides, therefore representing in both cases an obese fly model. The increase of triglyceride content due to the loss of a gene function suggests potential gene activities in energy homeostasis in a dose dependent manner that controls the amount of energy stored as triglycerides.

Example 5

Identificiation of the Genes

DevG20 (PDI)

Nucleic acids encoding the DevG20 protein of the present invention were identified using plasmid-rescue technique. Genomic DNA sequences of about 1 kb were isolated that are localised directly 3' to HD-EP(X)10478 or HD-EP(X) 31424 integrations. Using those isolated genomic sequences public databases like Berkeley Drosophila Genome Project (GadFly) were screened thereby confirming the integration side of HD-EP(X)10478 and HD-EP(X)31424 and nearby localised endogenous genes (FIG. 3). FIG. 3 shows the molecular organisation of the DevG20 locus. Genomic DNA sequence is represented by the assembly AE003487 as a black line that includes the integration sites of EP(X)1503, HD-EP(X)10478 and HD-EP(X)31424. Numbers represent the coordinates of AE003487 genomic DNA, the predicted genes and the EP-vector integration sites. Arrows represent the direction of ectopic expression of endogenous genes controlled by the Gal4 promoters in the EP-vectors. Predicted exons of genes CG2446 and CG 1837 are shown as grey bars. Using plasmid rescue method about 1 kb genomic DNA sequences that are directly localised 3' of the HD-EP (X)10478 and HD-EP(X)31424 integration sites were isolated. Using the 1 kb plasmid rescue DNA public DNA sequence databases were screened thereby identifying the integration sites of HD-EP(X)10478 and HD-EP(X)31424.

HD-EP(X)10478 and HD-EP(X)31424 are integrated in the predicted gene CG2446 that is represented by the EST clots 241_2–4 but their Gal4 promoters direct ectopic expression of endogenous genes in the opposite direction in respect to the direction of CG2446 expression. About 2 kb 3' of HD-EP(X)10478 and HD-EP(X)31424 integration sites the predicted gene CG1837 is localized that corresponds to est clot 3553_14 and could be expressed ectopically using "FB- and elav-Gal4-drivers". The ectopic expression of CG1837 in the fatbody or weaker in neurons leads to increase of triglyceride content in flies.

HD-EP(X)10478 is inserted into the first predicted exon of CG2446 that corresponds to the EST clot 241_2–4 in antisense orientation. Gal4 promoter region of HD-EP(X) 10478 drives expression in the opposite direction than CG2446 is expressed therefore could drive the ectopic expression of another endogenous gene. HD-EP(X)31424 is inserted in the first predicted exon of CG2446 and its Gal4 promoter drives expression in the opposite direction in comparison to CG2446 expression. A different endogenous gene CG1837 corresponding to EST clot 3553_14 is localized 2180 base pairs 3' in sense direction of both EP-integrations. CG1837 can be expressed ectopically via HD-EP(X)10478 and HD-EP(X)31424, leading to obesity.

DevG4 (MRP4)

Nucleic acids encoding the DevG4 protein of the present invention were identified using plasmid-rescue technique. Genomic DNA sequences of about 0.8 kb were isolated that are localised directly 3' to the EP(2)0646, EP(2)2517 and EP(2)2188 integration. Using those isolated genomic sequences public databases like Berkeley Drosophila Genome Project (GadFly) were screened thereby confirming the integration side of 0646, EP(2)2517 and EP(2)2188 and nearby localised endogenous genes (FIG. 8). FIG. 8 shows the molecular organisation of the DevG4 locus. In FIG. 8, genomic DNA sequence is represented by the assembly as a dotted black line (17.5 kb, starting at position 8256000 on chromosome 2L) that includes the integration sites of 0646, EP(2)2517 and EP(2)2188 (arrows). Numbers represent the coordinates of the genomic DNA. Arrows represent the direction of ectopic expression of endogenous genes controlled by the Gal4 promoters in the EP-vectors. Transcribed DNA sequences (ESTs and clots) are shown as bars in the lower two lines.

Predicted exons of gene CG7627 (GadFly) are shown as green bars and introns as grey bars.

0646, EP(2)2517 and EP(2)2188 are integrated directly 5' of the EST Clot 6022_1 in antisense orientation. Clot 6022_1 represents a cDNA clone meaning that is showing that the DNA sequence is expressed in Drosophila. Clot 6022_1 sequence overlaps with the sequence of the predicted gene CG7627 therefore Clot 6022_1 includes the 5' end of DevG4 gene and EP(2)0646 and EP(2)2517 are homozygous viably integrated in the promoter of DevG4. Using the 0.8 kb plasmid rescue DNA, public DNA sequence databases were screened thereby identifying the integration sites of EP(2)0646 and EP(2)2517. It was found that EP(2)0646 and EP(2)2517 are integrated in the promoter of the gene with GadFly Accession Number CG7627 that is also represented by the EST clot 6022_1. The Gal4 promoters if should direct ectopic expression of endogenous genes in the opposite direction in respect to the direction of CG7627 expression. Therefore, expression of the CG7627 could be effected by homozygous viable integration of EP(2)0646, EP(2)2517 and EP(2)2188 leading to increase of the energy storage triglycerides DevG22

FIG. 14 shows genomic DNA sequence represented by the assembly as a dotted black line (15 kb, starting at position 171400.5 on chromosome 2L) that includes the integration site of EP(2)20388 (arrow). Numbers represent the coordinates of the genomic DNA. Arrows represent the direction of ectopic expression of endogenous genes controlled by the Gal4 promoters in the EP-vectors. Transcribed DNA sequences (ESTs and clots) are shown as green bars in another line. Predicted exons of gene with GadFly Accession Number CG17646 are shown as green bars and introns as grey bars. It was found that DevG22 encodes for a novel gene that is predicted by GadFly sequence analysis programs as CG17646. Using plasmid rescue method about 0.6 kb genomic DNA sequences that are directly localised 3' of the EP(2)20388 integration site were isolated. Using the 0.6 kb plasmid rescue DNA, public DNA sequence databases were screened thereby identifying the integration site of EP(2)20388. EP(2)20388 is integrated directly 5' of the EST SD03967 in sense orientation. SD03967 represents a cDNA clone meaning that its DNA sequence is expressed in Drosophila. SD03967 sequence overlaps with the 5' sequence of the predicted gene CG 17646 therefore SD03967 includes the 5' and the 3' end of DevG22 gene. The 3' end of SD03967 does not overlap with CG17646 sequence therefore the cDNA of DevG22 might be even longer than shown in FIG. 14. EP(2)20388 is integrated in the promoter of the gene CG17646 that is also represented by EST SD03967; its Gal4 promoter should direct ectopic expression of CG 17646. Therefore, expression of the CG 17646 could be effected by homozygous viable integration of EP(2)20388 leading to increase of the energy storage triglycerides.

Example 6

Analysis of DevG20

DevG20 encodes for a novel gene that is predicted by GadFly sequence analysis programs and isolated EST clones. Neither phenotypic nor functional data are available in the prior art for the novel gene CG1837, referred to as DevG20 in the present invention. The present invention is describing the nucleic acid sequence of DevG20, as shown in FIG. 4A, SEQ ID NO:1.

The present invention is describing a polypeptide comprising the amino acid sequence of SEQ ID NO:2, as presented using the one-letter code in FIG. 4B. DevG20 is 416 amino acids in length. An open reading frame was identified by beginning with an ATP initiation codon at nucleotide 37 and ending with a CAC stop codon at nucleotide 1284 (FIG. 4B).

The predicted amino acid sequence was searched in the publicly available GenBank database. In search of sequence databases, it was found, for example, that DevG20 has 60% homology with human hGRP58 protein, a potential 58 kDa glucose regulated protein of 324 amino acids (GenBank Accession Number NP_110437.1; identical to former Accession Numbers AAH01199 and BC001199) (see FIGS. 4C and 4D; SEQ ID NO:1 and 2). In particular, Drosophila DevG20 and human hGRP58 protein share 60% homology (see FIG. 5), starting between amino acid 84 and 407 of DevG20 (and amino acids 1 to 316 of hGRP58). hGRP58 protein is homologous to a mouse protein encoded by the cDNA clone 601333564F1 NCI_CGAP_Mam6, identified using tblastp sequence comparison of a protein with translated mouse EST clones.

Using InterPro protein analysis tools, it was found, for example, that the DevG20 protein has at least three Thioredoxin protein motifs and an endoplasmic reticulum target sequence. These motifs and targeting sequencing are also found in glucose-regulated proteins and Protein disulfide isomerases. Glucose regulated proteins and Protein disulfide isomerases are chaperones that are involved in many different processes like lipoprotein assembly at the endoplasmic reticulum.

DevG20 encodes for a novel protein that is homologous to the family of protein disulfide isomerases or glucose regulated proteins. Based upon homology, DevG20 protein of the invention and each homologous protein or peptide may share at least some activity.

Example 7

Analysis of DevG4

As described above, DevG4 is encoded by GadFly Accession Number CG7627. The nucleic acid sequence of Drosophila DevG4, as shown in FIG. 9A, SEQ ID NO:9. The present invention is describing a polypeptide comprising the amino acid sequence of SEQ ID NO:10, as presented using the one-letter code in FIG. 9B. Drosophila DevG4 protein is 1355 amino acids in length. An open reading frame was identified beginning with an ATP initiation codon at nucleotide 158 and ending with a stop codon at nucleotide 4225. Drosophila DevG4 has additional 28 amino acids at the N-terminus without changing the frame in comparison to the predicted CG7627 protein after combining Clot 6022_1 and CG7627 cDNA sequences.

The predicted amino acid sequence was searched in the publicly available GenBank (NCBI) database. The search indicated, that *Drosophila* DevG4 has about 40% identity with human MRP4 (MOAT-B) protein, a ATP-binding cassette (ABC) transporter protein of 1325 amino acids (Accession Number: NP_005836; SEQ ID NO:10) (see FIG. 9C). In particular, *Drosophila* DevG4 and human homolog DevG4 (hMRP4) proteins share about 80% homology (see FIG. 9D), starting between amino acid 8 and 1330 of DevG4 (and amino acids 7 to 1277 of hMRP4).

Since the protein domains found in member of the ABC superfamily are highly conserved, a comparison (Clustal X 1.8) between the four protein domains of *Drosophila* DevG4 with human and mouse homolog proteins was conducted (see FIG. 11). We found that human and mouse (sequence is only partially available) MRP4 as closest homologous proteins to the *Drosophila* DevG4 protein. Using InterPro protein analysis tools, it was found, that the DevG4 protein has at least 4 four protein motifs domains (FIG. 10). These motifs and targeting sequencing are found throughout the whole ABC transporter superfamliy. ABC transporters are membrane spanning proteins that are involved in many different transport processes. FIG. 11A shows the alignment of the ABC-membrane I domains. The identity of amino acids of *Drosophila* DevG4 and human hMRP4 is 41% and the similarity of the sequence is 63%. FIG. 11B shows the alignment of the ABC-tran I domains. The identity of amino acids of *Drosophila* DevG4 and human hMRP4 is 56% and the similarity 75%. No mouse sequence is available. FIG. 11C shows the alignment of the ABC-membrane II domains. The identity of amino acids of *Drosophila* DevG4 and human hMRP4 is 42% and the similarity 60%. No mouse sequence is available. FIG. 11D shows the alignment of the ABC-tran II domains. No mouse sequence is available. The identity of amino acids of *Drosophila* DevG4 and human hMRP4 is 69% and the similarity 86%. Human and mouse ABC-tran II domains are almost identical.

Based upon homology, *Drosophila* DevG4 protein and each homologous protein or peptide may share at least some activity. The DevG4 protein has two characteristic ABC-membrane domains, a six transmembrane helical region (labeled 'ABC_membrane' in FIG. 10, ABC transporter transmembrane region) which anchors the protein in cell membranes. In addition, DevG4 has two ABC-transporter domains of several hundred amino acid residues (labeled 'ABC-tran' in FIG. 10, ABC transporter), including an ATP-binding site. Proteins of the ABC family are membrane spanning proteins associated with a variety of distinct biological processes in both prokaryotes and eukaryotes, for example in transport processes such as active transport of small hydrophilic molecules across the cytoplasmic membrane. Furthermore, a single MMR-HSR1 domain (GTPase of unknown function, light grey square box in FIG. 4A) was identified in DevG4. FIG. 10 shows the has a single characteristic ABC-transporter domain ('ABC trans') of the DevG22 protein.

Example 8

Analyis of DevG22

As discussed above, *Drosophila* DevG22 protein is encoded GadFly accession number CG 17646. The present invention is describing the nucleic acid sequence of DevG22, as shown in FIG. 15A, SEQ ID NO:11. The present invention is describing a polypeptide comprising the amino acid sequence of SEQ ID NO:12, as presented using the one-letter code in FIG. 15B. *Drosophila* DevG22 protein is 627 amino acids in length. An open reading frame was identified beginning with an ATP initiation codon at nucleotide 576 and ending with a stop codon at nucleotide 2459.

The predicted amino acid sequence was searched in the publicly available GenBank database. In search of sequence databases, it was found, for example, that DevG22 has almost 40% identity with human White (ABC8, ABCG1) protein, a ATP-binding cassette (ABC) transporter protein of 674 amino acids (GenBank Accession Number XP_009777.3; see FIGS. 15C and 15D; SEQ ID NO:5 and SEQ ID NO:6). In particular, *Drosophila* DevG22 and the human homolog protein share about 70% homology (see FIG. 17), starting between amino acid 57 and 622 of *Drosophila* DevG22 (and amino acids 27 to 507 of human DevG22-hWhite).

Using InterPro protein analysis tools, it was found that the DevG22 protein has at least 1 one protein motif (FIG. 16). The White-like subfamily of ABC transporters is characterized by the single ABC-tran domain and the overall amino acid sequence. Therefore, the complete coding sequence and not only the domains are compared. FIG. 17 shows the alignment of human, mouse, and *Drosophila* DevG22 proteins. *Drosophila* DevG22 is 36% identical and 52% similar to human DevG22 (hWhite; ABC8, ABCG1, GenBank Accession Number XP_009777). *Drosophila* DevG22 is 36% identical and 51% similar to mouse DevG22 (mWhite; GenBank Accession Number NP_033723). Therefore, the vertebrate white transporter is the closest homologue to *Drosophila* DevG22. Human and mouse White proteins show 95% identity and 96% similarity. Based upon homology, DevG22 protein of the invention and each homologous protein or peptide may share at least some activity.

Example 9

Expression of the Polypeptides in Mammalian Tissues

For analyzing the expression of the polypeptides disclosed in this invention in mammalian tissues, several mouse strains (preferably mice strains C57BI/6J, C57BI/6 ob/ob and C57BI/KS db/db which are standard model systems in obesity and diabetes research) were purchased from Harlan Winkelmann (33178 Borchen, Germany) and maintained under constant temperature (preferably 22° C.), 40 percent humidity and a light/dark cycle of preferably $^{14}/_{10}$ hours. The mice were fed a standard chow (for example, from ssniff Spezialitäten GmbH, order number ssniff M-Z V1126-000). Animals were sacrificed at an age of 6 to 8 weeks. The animal tissues were isolated according to standard procedures known to those skilled in the art, snap frozen in liquid nitrogen and stored at −80° C. until needed.

For analyzing the role of the proteins disclosed in this invention in the in vitro differentiation of different mammalian cell culture cells for the conversion of pre-adipocytes to adipocytes, mammalian fibroblast (3T3-L1) cells (e.g., Green & Kehinde, Cell 1: 113–116, 1974) were obtained from the American Tissue Culture Collection (ATCC, Hanassas, Va., USA; ATCC-CL 173). 3T3-L1 cells were maintained as fibroblasts and differentiated into adipocytes as described in the prior art (e.g., Qiu. et al., J. Biol. Chem. 276:11988–95, 2001; Slieker et al., BBRC 251: 225–9, 1998). At various time points of the differentiation procedure, beginning with day 0 (day of confluence) and day 2 (hormone addition; for example, dexamethason and 3-isobutyl-1-methylxanthin), up to 10 days of differentiation, suitable aliquots of cells were taken every two days. Alternatively, mammalian fibroblast 3T3-F442A cells (e.g., Green & Kehinde, Cell 7: 105–113, 1976) were obtained from the Harvard Medical School, Department of Cell Biology (Boston, Mass., USA). 3T3-F442A cells were maintained as fibroblasts and differentiated into adipocytes as described previously (Djian, P. et al., J. Cell. Physiol., 124:554–556, 1985). At various time points of the differentiation procedure, beginning with day 0 (day of confluence and hormone addition, for example, Insulin), up to 10 days of differentiation, suitable aliquots of cells were taken every two days. 3T3-F442A cells are differentiating in vitro already in the confluent stage after hormone (insulin) addition.

RNA was isolated from mouse tissues or cell culture cells using Trizol Reagent (for example, from Invitrogen, Karlsruhe, Germany) and further purified with the RNeasy Kit (for example, from Qiagen, Germany) in combination with an DNase-treatment according to the instructions of the manufacturers and as known to those skilled in the art. Total RNA was reverse transcribed (preferrably using Superscript II RNaseH Reverse Transcriptase, from Invitrogen, Karlsruhe, Germany) and subjected to Taqman analysis preferrably using the Taqman 2×PCR Master Mix (from Applied Biosystems, Weiterstadt, Germany; the Mix contains according to the Manufacturer for example AmpliTaq Gold DNA Polymerase, AmpErase UNG, dNTPs with dUTP, passive reference Rox and optimized buffer components) on a GeneAmp 5700 Sequence Detection System (from Applied Biosystems, Weiterstadt, Germany).

For the analysis of the expression of DevG20, taqman analysis was performed using the following primer/probe pair (see FIG. 6): Mouse DevG20 (PDI) forward primer (SEQ ID NO:13): 5'-CAC GGG TGA CAA GGG CA-3'; mouse DevG20 (PDI) reverse primer (SEQ ID NO:14): 5'-CCC CTG TGC AAT AGT GTC CTC-3'; Taqman probe (SEQ ID NO:15): (5/6-FAM) TGC TGG CAC TCA CCG AGA AGA GCT T (5/6-TAMRA).

As shown in FIG. 6A, real time PCR (Taqman) analysis of the expression of DevG20 protein in mammalian (mouse) tissues revealed that DevG20 (PDI) is rather ubiquitously expressed in various mouse tissues. However, a clear expression in WAT and BAT can also be demonstrated. DevG20 (PDI) shows an up-regulation of its expression in BAT, cortex and spleen of genetically obese ob/ob mice (FIG. 6B). In addition, its expression in kidney and bone marrow of fasted mice is also up-regulated. Even though no up-regulation of DevG20 (PDI) expression in WAT of ob/ob mice has been observed, we can clearly demonstrate a two-fold up-regulation of its expression during the in vitro differentiation of 3T3-L1 cells from pre-adipocytes to mature adipocytes (FIG. 6C).

For the analysis of the expression of DevG4, taqman analysis was performed using the following primer/probe pair (see FIG. 12): Mouse DevG4 (mrp4) forward primer (SEQ ID NO:16): 5'-CAA GTA GCG CCC ACC CC-3'; Mouse DevG4 (mrp4) reverse primer (SEQ ID NO:17): 5'-AGT TCA CAT TGT CGA AGA CGA TGA-3'; Taqman probe (SEQ ID NO:18): (5/6-FAM) AGG CTG GCC CCA CGA GGG A (5/6-TAMRA).

Taqman analysis revealed that DevG4 (mrp4) is ubiquitously expressed in various mouse tissues with highest levels of expression found in kidney (FIG. 12A). DevG4 (mrp4) shows a very prominent up-regulation of its expression in liver of genetically obese ob/ob mice (FIG. 12B). In addition, a significant up-regulation in kidney can also be observed under these conditions. Under fasting conditions, DevG4 (mrp4) expression seems to show a global down-regulation of its expression, this is especially prominent in the BAT tissue of fasting mice. DevG4 (mrp4) expression increases approximately 4-fold during the in vitro differentiation of 3T3-L1 cells from pre-adipocytes to mature adipocytes (FIG. 12C).

For the analysis of the expression of DevG22, taqman analysis was performed using the following primer/probe pair: Mouse DevG22 (white) forward primer (SEQ ID NO:19):5'-TCG TAT ACT GGA TGA CGT CCC A-3'; Mouse DevG22 (white) reverse primer (SEQ ID NO:20): 5'-TGG TAC CCA GAG CAG CGA AC-3'; Taqman probe (SEQ ID NO:21): (5/6-FAM) CCG TCG GAC GCT GTG CGT TTT (5/6-TAMRA).

Taqman analysis revealed that DevG22 (white) is predominantly expressed in neuronal tissues. However, a clear expression in other tissues like WAT or BAT has also been noted (FIGS. 18A and 18B). The expression of DevG22 (white) in BAT and WAT is under metabolic control: In fasted mice, expression goes up in BAT. Contrary to this, expression is increased in WAT and muscle in genetically obese ob/ob mice (FIG. 18B). This up-regulation in ob/ob mice correlates with the observed strong up-regulation of DevG22 (white) expression during the in vitro differentiation of 3T3-L1 cells (FIG. 18C).

All publications and patents mentioned in the above specification are herein incorporated by reference.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

LITERATURE

Klucken J, Büchler C, Orsó E, Kaminski W E, Porsch-Özcürümez M, Liebisch G, Kapinsky M, Diederich W, Drobnik W, Dean M, Allikmets R, Schmitz G.: ABCG1 (ABC8), the human homolog of the *Drosophila* white gene, is a regulator of macrophage cholesterol and phospholipid transport. Proc Natl Acad Sci USA. 2000 January;97(2):817–22.

Orsó E, Broccardo C, Kaminski WE, Böttcher A, Liebisch G, Drobnik W, Götz A, Chambenoit O, Diederich W, Langmann T, Spruss T, Luciani M-F, Rothe G, Lackner K J, Chimini G, Schmitz G.: Transport of lipids from Golgi to plasma membrane is defective in Tangier disease patients and Abc1-deficient mice. Nat Genet. 2000 February;24:192–6.

Venkateswaran A, Repa J J, Lobaccaro J-M A, Bronson A, Mangelsdorf D J, Edwards P A.: Human White/murine ABC8 mRNA levels are highly induced in lipid-loaded macrophages. J Biol Chem. 2000 May;275(19):14700–7.

Nakamura M, Ueno S, Sano A, Tanabe H.: Polymorphisms of the human homologue of the *Drosophila* white gene are associated with mood and panic disorders. Mol Psychiatry. 1999 March;4(2):155–62.

Bodzioch M, Orso E, Klucken J, Langmann T, Bottcher A, Diederich W, Drobnik W, Barlage S, Buchler C, Porsch-Ozcurumez M, Kaminski W E, Hahmann H W, Oette K, Rothe G, Aslanidis C, Lackner K J, Schmitz G.: The gene encoding ATP-binding cassette transporter 1 is mutated in Tangier disease. Nat Genet. 1999 August;22(4):347–51.

Brooks-Wilson A, Marcil M, Clee S M, Zhang L H, Roomp K, van Dam M, Yu L, Brewer C, Collins J A, Molhuizen H O, Loubser O, Ouelette BF, Fichter K, Ashbourne-Excoffon K J, Sensen C W, Scherer S, Mott S, Denis M, Martindale D, Frohlich J, Morgan K, Koop B, Pimstone S, Kastelein J J, Hayden M R, et al.: Mutations in ABC1 in Tangier disease and familial high-density lipoprotein deficiency. Nat Genet. 1999 August;22(4):336–45.

Rust S, Rosier M, Funke H, Real J, Amoura Z, Piette J C, Deleuze J F, Brewer H B, Duverger N, Denefle P, Assmann G.: Tangier disease is caused by mutations in the gene encoding ATP-binding cassette transporter 1. Nat Genet. 1999 August;22(4):352–5.

Schuetz J D, Connelly M C, Sun D, Paibir S D, Flynn P M, Srinivas R V, Kumar A, Fridland A.: MRP4. A previously unidentified factor in resistance to nucleoside-based antiviral drugs. Nat Med. 1999 September;5(9):1048–51.

Wada M, Toh S, Taniguchi K, Nakamura T, Uchiumi T, Kohno K, Yoshida I, Kimura A, Sakisaka S, Adachi Y, Kuwano M.: Mutations in the canilicular organic anion transporter (cMOAT) gene, a novel ABC transporter, in patients with hyperbilirubinemia II/Dubin-Johnson syndrome. Hum Mol Genet. 1998 February;7(2):203–7.

Allikmets R, Singh N, Sun H, Shroyer NF, Hutchinson A, Chidambaram A, Gerrard B, Baird L, Stauffer D, Peiffer A, Rattner A, Smallwood P, Li Y, Anderson K L, Lewis R A, Nathans J, Leppert M, Dean M, Lupski J R.: A photoreceptor cell-specific ATP-binding transporter gene (ABCR) is mutated in recessive Stargardt macular dystrophy. Nat Genet. 1997 March; 15 (3):236–46.

The invention claimed is:

1. A composition comprising an isolated ABC transporter DevG22 polypeptide encoded by a polynucleotide sequence as defined in SEQ ID NO:5, and an acceptable carrier, wherein said ABC transporter DevG22 polypeptide regulates energy homeostasis and metabolism of triglycerides.

2. The composition of claim 1, wherein the ABC transporter DevG22 polypepride comprises an amino acid sequence set forth in SEQ ID NO:6.

3. The composition of claim 1, wherein the ABC transporter DevG22 polypeptide is a recombinant polypeptide.

4. The composition of claim 1, wherein the ABC transporter DevG22 polypeptide is a recombinant fusion polypeptide.

5. The composition of claim 1, wherein the composition is a diagnostic composition.

* * * * *

SEQUENCE LISTING

<160> NUMBER OF SEQ ID NOS: 21

<210> SEQ ID NO 1
<211> LENGTH: 2712
<212> TYPE: DNA
<213> ORGANISM: Human

<400> SEQUENCE: 1

```
gtcatgttct tcgcgccctg gtgtggacac tgccagcggc tgcagccgac ttggaatgac      60
ctgggagaca aatacaacag catggaagat gccaaagtct atgtggctaa agtggactgc     120
acggcccact ccgacgtgtg ctccgcccag ggggtgcgag gatacccac cttaaagctt      180 ttcaagccag gccaagaagc tgtgaagtac cagggtcctc gggacttcca gacactggaa     240
aactggatgc tgcagacact gaacgaggag ccagtgacac cagagccgga agtggaaccg     300
cccagtgccc ccgagctcaa gcaagggctg tatgagctct cagcaagcaa ctttgagctg     360
cacgttgcac aaggcgacca ctttatcaag ttcttcgctc cgtggtgtgg tcactgcaaa     420
gccctggctc caacctggga gcagctggct ctgggccttg aacattccga aactgtcaag     480
attggcaagg ttgattgtac acagcactat gaactctgct ccggaaacca ggttcgtggc     540
tatcccactc ttctctggtt ccgagatggg aaaaaggtgg atcagtacaa gggaaagcgg     600
gatttggagt cactgaggga gtacgtggag tcgcagctgc agcgcacaga gactggagcg     660
acggagaccg tcacgccctc agaggcccg gtgctggcag ctgagcccga ggctgacaag     720
ggcactgtgt tggcactcac tgaaaataac ttcgatgaca ccattgcaga aggataacc      780 ttcatcaagt tttatgctcc atggtgtggt cattgtaaga ctctggctcc tacttgggag     840
gaactctcta aaaaggaatt ccctggtctg gcgggggtca agatcgccga agtagactgc     900
actgctgaac ggaatatctg cagcaagtat cggtacgag gctaccccac gttattgctt     960
ttccgaggag ggaagaaagt cagtgagcac agtggaggca gagaccttga ctcgttacac    1020
cgctttgtcc tgagccaagc gaaagacgaa ctttaggaac acagttggag gtcacctctc    1080
ctgcccagct cccgcaccct gcgtttagga gttcagtccc acagaggcca ctgggttccc    1140
agtggtggct gttcagaaag cagaacatac taagcgtgag gtatcttctt tgtgtgtgtg    1200
ttttccaagc caacacactc tacagattct ttattaaatg tgtaactcat ggtcactgtg    1260
taaacatttt cagtggcgat atatcccctt tgaccttctc ttgatgaaat ttacatggtt    1320 tccttgtgaga ctaaatagc gttgagggaa atgaaattgc tggactattt gtggctcctg    1380
agttgagtga ttttggtgaa agaaagcaca tccaaagcat agtttacctg cccacgagtt    1440
```

-continued

```
ctggaaaggt ggccttgtgg cagtattgac gttcctctga tcttaaggtc acagttgact    1500
caatactgtg ttggtccgta gcatggagca gattgaaatg caaaaaccca cacctctgga    1560
agataccttc acggccgctg ctggagcttc tgttgctgtg aatacttctc tcagtgtgag    1620
aggttagccg tgatgaaagc agcgttactt ctgaccgtgc ctgagtaaga gaatgctgat    1680
gccataactt tatgtgtcga tacttgtcaa atcagttact gttcagggga tccttctgtt    1740
tctcacgggg tgaaacatgt ctttagttcc tcatgttaac acgaagccag agcccacatg    1800
aactgttgga tgtcttcctt agaaagggta ggcatggaaa attccacgag gctcattctc    1860
agtatctcat taactcattg aaagattcca gttgtatttg tcacctgggg tgacaagacc    1920
agacaggctt tcccaggcct gggtatccag ggaggctctg cagccctgct gaagggccct    1980
aactagagtt ctagagtttc tgattctgtt tctcagtagt cctttagag gcttgctata    2040 cttggtctgc ttcaaggagg tcgaccttct aatgtatgaa gaatgggatg catttgatct    2100
caagaccaaa gacagatgtc agtgggctgc tctggccctg gtgtgcacgg ctgtggcagc    2160
tgttgatgcc agtgtcctct aactcatgct gtccttgtga ttaaacacct ctatctccct    2220
tgggaataag cacatacagg cttaagctct aagatagata ggtgtttgtc cttttaccat    2280
cgagctactt cccataataa ccactttgca tccaacactc ttcacccacc tcccatacgc    2340 aagggatgt ggatacttgg cccaaagtaa ctggtggtag gaatcttaga aacaagacca    2400
cttatactgt ctgtctgagg cagaagataa cagcagcatc tcgaccagcc tctgccttaa    2460
aggaaatctt tattaatcac gtatggttca cagataattc ttttttttaaa aaacccaac    2520 ctcctagaga agcacaactg tcaagagtct tgtacacaca acttcagctt tgcatcacga    2580
gtcttgtatt ccaagaaaat caaagtggta caatttgttt gtttacacta tgatactttc    2640
taaataaact cttttttttt aaaaaaaaaa aaaaaaaaaa aaaaaaaaaa aaaaaaaaaa    2700
aaaaaaaaaa ac                                                        2712
```

<210> SEQ ID NO 2
<211> LENGTH: 324
<212> TYPE: PRT
<213> ORGANISM: Human

<400> SEQUENCE: 2

```
Met Glu Asp Ala Lys Val Tyr Val Ala Lys Val Asp Cys Thr Ala His
  1               5                  10                  15

Ser Asp Val Cys Ser Ala Gln Gly Val Arg Gly Tyr Pro Thr Leu Lys
             20                  25                  30

Leu Phe Lys Pro Gly Gln Glu Ala Val Lys Tyr Gln Gly Pro Arg Asp
         35                  40                  45

Phe Gln Thr Leu Glu Asn Trp Met Leu Gln Thr Leu Asn Glu Glu Pro
     50                  55                  60

Val Thr Pro Glu Pro Glu Val Glu Pro Pro Ser Ala Pro Glu Leu Lys
 65                  70                  75                  80

Gln Gly Leu Tyr Glu Leu Ser Ala Ser Asn Phe Glu Leu His Val Ala
                 85                  90                  95

Gln Gly Asp His Phe Ile Lys Phe Phe Ala Pro Trp Cys Gly His Cys
            100                 105                 110

Lys Ala Leu Ala Pro Thr Trp Glu Gln Leu Ala Leu Gly Leu Glu His
        115                 120                 125

Ser Glu Thr Val Lys Ile Gly Lys Val Asp Cys Thr Gln His Tyr Glu
    130                 135                 140
```

```
Leu Cys Ser Gly Asn Gln Val Arg Gly Tyr Pro Thr Leu Leu Trp Phe
145                 150                 155                 160

Arg Asp Gly Lys Lys Val Asp Gln Tyr Lys Gly Lys Arg Asp Leu Glu
            165                 170                 175

Ser Leu Arg Glu Tyr Val Glu Ser Gln Leu Gln Arg Thr Glu Thr Gly
        180                 185                 190

Ala Thr Glu Thr Val Thr Pro Ser Glu Ala Pro Val Leu Ala Ala Glu
    195                 200                 205

Pro Glu Ala Asp Lys Gly Thr Val Leu Ala Leu Thr Glu Asn Asn Phe
210                 215                 220

Asp Asp Thr Ile Ala Glu Gly Ile Thr Phe Ile Lys Phe Tyr Ala Pro
225                 230                 235                 240

Trp Cys Gly His Cys Lys Thr Leu Ala Pro Thr Trp Glu Glu Leu Ser
            245                 250                 255

Lys Lys Glu Phe Pro Gly Leu Ala Gly Val Lys Ile Ala Glu Val Asp
        260                 265                 270

Cys Thr Ala Glu Arg Asn Ile Cys Ser Lys Tyr Ser Val Arg Gly Tyr
    275                 280                 285

Pro Thr Leu Leu Leu Phe Arg Gly Gly Lys Lys Val Ser Glu His Ser
290                 295                 300

Gly Gly Arg Asp Leu Asp Ser Leu His Arg Phe Val Leu Ser Gln Ala
305                 310                 315                 320

Lys Asp Glu Leu

<210> SEQ ID NO 3
<211> LENGTH: 4231
<212> TYPE: DNA
<213> ORGANISM: Human

<400> SEQUENCE: 3
ggacaggcgt ggcggccgga gccccagcat ccctgcttga ggtccaggag cggagcccgc     60
ggccaccgcc gcctgatcag cgcgaccccg gcccgcgccc gccccgcccg gcaagatgct    120
gcccgtgtac caggaggtga agcccaaccc gctgcaggac gcgaacatct gctcacgcgt    180
gttcttctgg tggctcaatc ccttgtttaa aattggccat aaacggagat tagaggaaga    240
tgatatgtat tcagtgctgc cagaagaccg ctcacagcac cttggagagg agttgcaagg    300
gttctgggat aaagaagttt taagagctga gaatgacgca cagaagcctt ctttaacaag    360
agcaatcata aagtgttact ggaaatctta tttagttttg ggaattttta cgttaattga    420
ggaaagtgcc aaagtaatcc agcccatatt tttgggaaaa attattaatt attttgaaaa    480
ttatgatccc atggattctg tggctttgaa cacagcgtac gcctatgcca cggtgctgac    540
tttttgcacg ctcattttgg ctatactgca tcacttatat ttttatcacg ttcagtgtgc    600
tgggatgagg ttacgagtag ccatgtgcca tatgattat  cggaaggcac ttcgtcttag    660
taacatggcc atgggaaga caaccacagg ccagatagtc aatctgctgt ccaatgatgt    720
gaacaagttt gatcaggtga cagtgttctt acacttcctg tgggcaggac cactgcaggc    780
gatcgcagtg actgccctac tctggatgga gataggaata tcgtgccttg ctgggatggc    840
agttctaatc attctcctgc ccttgcaaag ctgttttggg aagttgttct catcactgag    900
gagtaaaact gcaactttca cggatgccag gatcaggacc atgaatgaag ttataactgg    960
tataaggata ataaaaatgt acgcctggga aaagtcattt tcaaatctta ttaccaattt   1020
gagaaagaag gagatttcca agattctgag aagttcctgc ctcagggga tgaatttggc   1080
```

```
ttcgtttttc agtgcaagca aaatcatcgt gtttgtgacc ttcaccacct acgtgctcct   1140
cggcagtgtg atcacagcca gccgcgtgtt cgtggcagtg acgctgtatg gggctgtgcg   1200
gctgacggtt accctcttct tcccctcagc cattgagagg gtgtcagagg caatcgtcag   1260
catccgaaga atccagacct ttttgctact tgatgagata tcacagcgca accgtcagct   1320
gccgtcagat ggtaaaaaga tggtgcatgt gcaggatttt actgcttttt gggataaggc   1380
atcagagacc ccaactctac aaggccttte ctttactgtc agacctggcg aattgttagc   1440
tgtggtcggc cccgtgggag cagggaagtc atcactgtta agtgccgtgc tcggggaatt   1500
ggccccaagt cacgggctgg tcagcgtgca tggaagaatt gcctatgtgt ctcagcagcc   1560
ctgggtgttc tcgggaactc tgaggagtaa tattttattt gggaagaaat atgaaaagga   1620
acgatatgaa aaagtcataa aggcttgtgc tctgaaaaag gatttacagc tgttggagga   1680
tggtgatctg actgtgatag agatcggggg aaccacgctg agtggagggc agaaagcacg   1740
ggtaaacctt gcaagagcag tgtatcaaga tgctgacatc tatctcctgg acgatcctct   1800
cagtgcagta gatgcggaag ttagcagaca cttgttcgaa ctgtgtattt gtcaaatttt   1860
gcatgagaag atcacaattt tagtgactca tcagttgcag tacctcaaag ctgcaagtca   1920
gattctgata ttgaaagatg gtaaaatggt gcagaagggg acttacactg agttcctaaa   1980
atctggtata gattttggct ccctttttaaa gaaggataat gaggaaagtg aacaacctcc   2040
agttccagga actcccacac taaggaatcg taccttctca gagtcttcgg tttggtctca   2100
acaatcttct agaccctcct tgaaagatgg tgctctggga agccaagata cagagaatgt   2160
cccagttaca ctatcagagg agaaccgttc tgaaggaaaa gttggttttc aggcctataa   2220
gaattacttc agagctggtg ctcactggat tgtcttcatt ttccttattc tcctaaacac   2280
tgcagctcag gttgcctatg tgcttcaaga ttggtggctt tcatactggg caaacaaaca   2340
aagtatgcta aatgtcactg taaatggagg aggaaatgta accgagaagc tagatcttaa   2400
ctggtactta ggaatttatt caggtttaac tgtagctacc gttctttttg gcatagcaag   2460
atctctattg gtattctacg tccttgttaa ctcttcacaa actttgcaca acaaaatgtt   2520
tgagtcaatt ctgaaagctc cggtattatt ctttgataga aatccaatag gaagaatttt   2580
aaaatcgttt c tccaaagaca ttggacactt ggatgatttg ctgccgctga cgttttttaga   2640 tttcatccag acattgctac aagtggttgg tgtggtctct gtggctgtgg ccgtgattcc   2700
ttggatcgca ataccttgg t tccccttgg aatcattttc attttcttc ggcgatattt    2760 tttggaaacg tcaagagatg tgaagcgcct ggaatctaca actcggagtc cagtgttttc   2820
ccacttgtca tcttctctcc aggggctctg gaccatccgg gcatacaaag cagaagagag   2880
gtgtcaggaa ctgtttgatg cacaccagga tttacattca gaggcttggt tcttgttttt   2940
gacaacgtcc cgctggttcg ccgtccgtct ggatgccatc tgtgccatgt ttgtcatcat   3000
cgttgccttt gggtccctga ttctggcaaa aactctggat gccgggcagg ttggtttggc   3060
actgtcctat gccctcacgc tcatgggat gtttcagtgg tgtgttcgac aaagtgctga   3120
agttgagaat atgatgatct cagtagaaag ggtcattgaa tacacagacc ttgaaaaaga   3180
agcaccttgg gaatatcaga aacgcccacc accagcctgg ccccatgaag gagtgataat   3240 cttttgacaat gtgaacttca tgtacagtcc aggtgggcct ctggtactga agcatctgac   3300
agcactcatt aaatcacaag aaaaggttgg cattgtggga agaaccggag ctggaaaaag   3360
ttccctcatc tcagccctttt ttagattgtc agaacccgaa ggtaaatttt ggattgataa   3420
```

```
gatcttgaca actgaaattg gacttcacga tttaaggaag aaaatgtcaa tcatacctca    3480
ggaacctgtt ttgttcactg gaacaatgag gaaaaacctg gatcccttta aggagcacac    3540
ggatgaggaa ctgtggaatg ccttacaaga ggtacaactt aaagaaacca ttgaagatct    3600
tcctggtaaa atggatactg aattagcaga atcaggatcc aattttagtg ttggacaaag    3660
acaactggtg tgccttgcca gggcaattct caggaaaaat cagatattga ttattgatga    3720
agcgacggca aatgtggatc caagaactga tgagttaata caaaaaaaaa tccgggagaa    3780
atttgcccac tgcaccgtgc taaccattgc acacagattg aacaccatta ttgacagcga    3840
caagataatg gttttagatt caggaagact gaaagaatat gatgagccgt atgttttgct    3900
gcaaaataaa gagagcctat tttacaagat ggtgcaacaa ctgggcaagg cagaagccgc    3960
tgccctcact gaaacagcaa aacaggtata cttcaaaaga aattatccac atattggtca    4020
cactgaccac atggttacaa acacttccaa tggacagccc tcgaccttaa ctattttcga    4080
gacagcactg tgaatccaac caaaatgtca agtccgttcc gaaggcattt tccactagtt    4140
tttggactat gtaaaccaca ttgtactttt ttttactttg gcaacaaata tttatacata    4200
caagatgcta gttcatttga atatttctcc c                                   4231
```

<210> SEQ ID NO 4
<211> LENGTH: 1325
<212> TYPE: PRT
<213> ORGANISM: Human

<400> SEQUENCE: 4

```
Met Leu Pro Val Tyr Gln Glu Val Lys Pro Asn Pro Leu Gln Asp Ala
 1               5                  10                  15

Asn Ile Cys Ser Arg Val Phe Phe Trp Trp Leu Asn Pro Leu Phe Lys
            20                  25                  30

Ile Gly His Lys Arg Arg Leu Glu Glu Asp Asp Met Tyr Ser Val Leu
        35                  40                  45

Pro Glu Asp Arg Ser Gln His Leu Gly Glu Glu Leu Gln Gly Phe Trp
    50                  55                  60

Asp Lys Glu Val Leu Arg Ala Glu Asn Asp Ala Gln Lys Pro Ser Leu
65                  70                  75                  80

Thr Arg Ala Ile Ile Lys Cys Tyr Trp Lys Ser Tyr Leu Val Leu Gly
                85                  90                  95

Ile Phe Thr Leu Ile Glu Glu Ser Ala Lys Val Ile Gln Pro Ile Phe
            100                 105                 110

Leu Gly Lys Ile Ile Asn Tyr Phe Glu Asn Tyr Asp Pro Met Asp Ser
        115                 120                 125

Val Ala Leu Asn Thr Ala Tyr Ala Tyr Ala Thr Val Leu Thr Phe Cys
    130                 135                 140

Thr Leu Ile Leu Ala Ile Leu His His Leu Tyr Phe Tyr His Val Gln
145                 150                 155                 160

Cys Ala Gly Met Arg Leu Arg Val Ala Met Cys His Met Ile Tyr Arg
                165                 170                 175

Lys Ala Leu Arg Leu Ser Asn Met Ala Met Gly Lys Thr Thr Thr Gly
            180                 185                 190

Gln Ile Val Asn Leu Leu Ser Asn Asp Val Asn Lys Phe Asp Gln Val
        195                 200                 205

Thr Val Phe Leu His Phe Leu Trp Ala Gly Pro Leu Gln Ala Ile Ala
    210                 215                 220

Val Thr Ala Leu Leu Trp Met Glu Ile Gly Ile Ser Cys Leu Ala Gly
```

```
                225                 230                 235                 240
Met Ala Val Leu Ile Ile Leu Leu Pro Leu Gln Ser Cys Phe Gly Lys
                245                 250                 255
Leu Phe Ser Ser Leu Arg Ser Lys Thr Ala Thr Phe Thr Asp Ala Arg
            260                 265                 270
Ile Arg Thr Met Asn Glu Val Ile Thr Gly Ile Arg Ile Ile Lys Met
            275                 280                 285
Tyr Ala Trp Glu Lys Ser Phe Ser Asn Leu Ile Thr Asn Leu Arg Lys
        290                 295                 300
Lys Glu Ile Ser Lys Ile Leu Arg Ser Ser Cys Leu Arg Gly Met Asn
305                 310                 315                 320
Leu Ala Ser Phe Phe Ser Ala Ser Lys Ile Ile Val Phe Val Thr Phe
                325                 330                 335
Thr Thr Tyr Val Leu Leu Gly Ser Val Ile Thr Ala Ser Arg Val Phe
                340                 345                 350
Val Ala Val Thr Leu Tyr Gly Ala Val Arg Leu Thr Val Thr Leu Phe
                355                 360                 365
Phe Pro Ser Ala Ile Glu Arg Val Ser Glu Ala Ile Val Ser Ile Arg
            370                 375                 380
Arg Ile Gln Thr Phe Leu Leu Leu Asp Glu Ile Ser Gln Arg Asn Arg
385                 390                 395                 400
Gln Leu Pro Ser Asp Gly Lys Lys Met Val His Val Gln Asp Phe Thr
                405                 410                 415
Ala Phe Trp Asp Lys Ala Ser Glu Thr Pro Thr Leu Gln Gly Leu Ser
            420                 425                 430
Phe Thr Val Arg Pro Gly Glu Leu Leu Ala Val Val Gly Pro Val Gly
            435                 440                 445
Ala Gly Lys Ser Ser Leu Leu Ser Ala Val Leu Gly Glu Leu Ala Pro
        450                 455                 460
Ser His Gly Leu Val Ser Val His Gly Arg Ile Ala Tyr Val Ser Gln
465                 470                 475                 480
Gln Pro Trp Val Phe Ser Gly Thr Leu Arg Ser Asn Ile Leu Phe Gly
            485                 490                 495
Lys Lys Tyr Glu Lys Glu Arg Tyr Glu Lys Val Ile Lys Ala Cys Ala
            500                 505                 510
Leu Lys Lys Asp Leu Gln Leu Leu Glu Asp Gly Asp Leu Thr Val Ile
        515                 520                 525
Gly Asp Arg Gly Thr Thr Leu Ser Gly Gly Gln Lys Ala Arg Val Asn
530                 535                 540
Leu Ala Arg Ala Val Tyr Gln Asp Ala Asp Ile Tyr Leu Leu Asp Asp
545                 550                 555                 560
Pro Leu Ser Ala Val Asp Ala Glu Val Ser Arg His Leu Phe Glu Leu
                565                 570                 575
Cys Ile Cys Gln Ile Leu His Glu Lys Ile Thr Ile Leu Val Thr His
                580                 585                 590
Gln Leu Gln Tyr Leu Lys Ala Ala Ser Gln Ile Leu Ile Leu Lys Asp
            595                 600                 605
Gly Lys Met Val Gln Lys Gly Thr Tyr Thr Glu Phe Leu Lys Ser Gly
        610                 615                 620
Ile Asp Phe Gly Ser Leu Leu Lys Lys Asp Asn Glu Glu Ser Glu Gln
625                 630                 635                 640
Pro Pro Val Pro Gly Thr Pro Thr Leu Arg Asn Arg Thr Phe Ser Glu
                645                 650                 655
```

-continued

```
Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
    690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
            740                 745                 750

Gly Asn Val Thr Glu Lys Leu Asp Leu Asn Trp Tyr Leu Gly Ile Tyr
        755                 760                 765

Ser Gly Leu Thr Val Ala Thr Val Leu Phe Gly Ile Ala Arg Ser Leu
    770                 775                 780

Leu Val Phe Tyr Val Leu Val Asn Ser Ser Gln Thr Leu His Asn Lys
785                 790                 795                 800

Met Phe Glu Ser Ile Leu Lys Ala Pro Val Leu Phe Phe Asp Arg Asn
                805                 810                 815

Pro Ile Gly Arg Ile Leu Asn Arg Phe Ser Lys Asp Ile Gly His Leu
            820                 825                 830

Asp Asp Leu Leu Pro Leu Thr Phe Leu Asp Phe Ile Gln Thr Leu Leu
        835                 840                 845

Gln Val Val Gly Val Val Ser Val Ala Val Ala Val Ile Pro Trp Ile
    850                 855                 860

Ala Ile Pro Leu Val Pro Leu Gly Ile Ile Phe Ile Phe Leu Arg Arg
865                 870                 875                 880

Tyr Phe Leu Glu Thr Ser Arg Asp Val Lys Arg Leu Glu Ser Thr Thr
                885                 890                 895

Arg Ser Pro Val Phe Ser His Leu Ser Ser Ser Leu Gln Gly Leu Trp
            900                 905                 910

Thr Ile Arg Ala Tyr Lys Ala Glu Glu Arg Cys Gln Glu Leu Phe Asp
        915                 920                 925

Ala His Gln Asp Leu His Ser Glu Ala Trp Phe Leu Phe Leu Thr Thr
    930                 935                 940

Ser Arg Trp Phe Ala Val Arg Leu Asp Ala Ile Cys Ala Met Phe Val
945                 950                 955                 960

Ile Ile Val Ala Phe Gly Ser Leu Ile Leu Ala Lys Thr Leu Asp Ala
                965                 970                 975

Gly Gln Val Gly Leu Ala Leu Ser Tyr Ala Leu Thr Leu Met Gly Met
            980                 985                 990

Phe Gln Trp Cys Val Arg Gln Ser Ala Glu Val Glu Asn Met Met Ile
        995                 1000                1005

Ser Val Glu Arg Val Ile Glu Tyr Thr Asp Leu Glu Lys Glu Ala Pro
    1010                1015                1020

Trp Glu Tyr Gln Lys Arg Pro Pro Ala Trp Pro His Glu Gly Val
1025                1030                1035                1040

Ile Ile Phe Asp Asn Val Asn Phe Met Tyr Ser Pro Gly Gly Pro Leu
                1045                1050                1055

Val Leu Lys His Leu Thr Ala Leu Ile Lys Ser Gln Glu Lys Val Gly
            1060                1065                1070
```

-continued

```
Ile Val Gly Arg Thr Gly Ala Gly Lys Ser Ser Leu Ile Ser Ala Leu
    1075                1080                1085

Phe Arg Leu Ser Glu Pro Glu Gly Lys Ile Trp Ile Asp Lys Ile Leu
    1090                1095                1100

Thr Thr Glu Ile Gly Leu His Asp Leu Arg Lys Met Ser Ile Ile
1105                1110                1115                1120

Pro Gln Glu Pro Val Leu Phe Thr Gly Thr Met Arg Lys Asn Leu Asp
            1125                1130                1135

Pro Phe Lys Glu His Thr Asp Glu Glu Leu Trp Asn Ala Leu Gln Glu
        1140                1145                1150

Val Gln Leu Lys Glu Thr Ile Glu Asp Leu Pro Gly Lys Met Asp Thr
    1155                1160                1165

Glu Leu Ala Glu Ser Gly Ser Asn Phe Ser Val Gly Gln Arg Gln Leu
    1170                1175                1180

Val Cys Leu Ala Arg Ala Ile Leu Arg Lys Asn Gln Ile Leu Ile Ile
1185                1190                1195                1200

Asp Glu Ala Thr Ala Asn Val Asp Pro Arg Thr Asp Glu Leu Ile Gln
            1205                1210                1215

Lys Lys Ile Arg Glu Lys Phe Ala His Cys Thr Val Leu Thr Ile Ala
        1220                1225                1230

His Arg Leu Asn Thr Ile Ile Asp Ser Asp Lys Ile Met Val Leu Asp
    1235                1240                1245

Ser Gly Arg Leu Lys Glu Tyr Asp Glu Pro Tyr Val Leu Leu Gln Asn
    1250                1255                1260

Lys Glu Ser Leu Phe Tyr Lys Met Val Gln Gln Leu Gly Lys Ala Glu
1265                1270                1275                1280

Ala Ala Ala Leu Thr Glu Thr Ala Lys Gln Val Tyr Phe Lys Arg Asn
        1285                1290                1295

Tyr Pro His Ile Gly His Thr Asp His Met Val Thr Asn Thr Ser Asn
    1300                1305                1310

Gly Gln Pro Ser Thr Leu Thr Ile Phe Glu Thr Ala Leu
    1315                1320                1325
```

<210> SEQ ID NO 5
<211> LENGTH: 2921
<212> TYPE: DNA
<213> ORGANISM: Human

<400> SEQUENCE: 5

| | | |
|---|---|---|
| gctttataaa gggagtttc cctgcacaag ctctctctct tgtctgccgc catgtgagac | 60 |
| atgcctttca ccttccgcca tgatcatgag gcttccccag ccacatggaa ctaatgccag | 120 |
| cagttactct gcagagatga cggagcccaa gtcggtgtgt gtctcggtgg atgaggtggt | 180 |
| gtccagcaac atggaggcca ctgagacgga cctgctgaat ggacatctga aaaagtaga | 240 |
| taataacctc acgaagccc agcgcttctc tccttgcct cggagggcag ctgtgaacat | 300 |
| tgaattcagg gacctttcct attcggttcc tgaaggaccc tggtggagga agaaaggata | 360 |
| caagaccctc ctgaaaggaa tttccggaa gttcaatagt ggtgagttgg tggccattat | 420 |
| gggtccttcc ggggccggga agtccacgct gatgaacatc ctggctggat acaggggagac | 480 |
| gggcatgaag gggccgtcc tcatcaacgg cctgccccgg gacctgcgct gcttccggaa | 540 |
| ggtgtcctgc tacatcatgc aggatgacat gctgctgccg catctcactg tgcaggaggc | 600 |
| catgatggtg tcggcacatc tgaagcttca ggagaaggat gaaggcagaa gggaaatggt | 660 |
| caaggagata ctgacagcgc tgggcttgct gtcttgcgcc aacacgcgga ccgggagcct | 720 |

-continued

```
gtcaggtggt cagcgcaagc gcctggccat cgcgctggag ctggtgaaca accctccagt        780
catgttcttc gatgagccca ccagcggcct ggacagcgcc tcctgcttcc aggtggtctc        840
gctgatgaaa gggctcgctc aagggggtcg ctccatcatt tgcaccatcc accagcccag        900
cgccaaactc ttcgagctgt tcgaccagct ttacgtcctg agtcaaggac aatgtgtgta        960
ccggggaaaa gtctgcaatc ttgtgccata tttgagggat ttgggtctga actgcccaac       1020
ctaccacaac ccagcagatt ttgtcatgga ggttgcatcc ggcgagtacg gtgatcagaa       1080
cagtcggctg gtgagagcgg ttcgggaggg catgtgtgac tcagaccaca agagagacct       1140 cggggggtgat gccgaggtga acccttttct ttggcaccgg ccctctgaag aggactcctc       1200
gtccatggaa ggctgccaca gcttctctgc cagctgcctc acgcagttct gcatcctctt       1260
caagaggacc ttcctcagca tcatgaggga ctcggtcctg acacacctgc gcatcacctc       1320
gcacattggg atcggcctcc tcattggcct gctgtacttg gggatcggga acgaagccaa       1380
gaaggtcttg agcaactccg gcttcctctt cttctccatg ctgttcctca tgttcgcggc       1440
cctcatgcct actgttctga catttcccct ggagatggga gtcttttctt gggaacacct       1500
gaactactgg tacagcctga aggcctacta cctggccaag accatggcag acgtgccctt       1560
tcagatcatg ttcccagtgg cctactgcag catcgtgtac tggatgacgt cgcagccgtc       1620
cgacgccgtg cgctttgtgc tgtttgccgc gctgggcacc atgacctccc tggtggcaca       1680
gtccctgggc ctgctgatcg gagccgcctc cacgtccctg caggtggcca ctttcgtggg       1740
cccagtgaca gccatcccgg tgctcctgtt ctcggggttc ttcgtcagct tcgacaccat       1800
ccccacgtac ctacagtgga tgtcctacat ctccctatgtc aggtatgggt tcgaaggggt       1860
catcctctcc atctatggct tagaccggga agatctgcac tgtgacatcg acgagacgtg       1920
ccacttccag aagtcggagg ccatcctgcg ggagctggac gtggaaaatg ccaagctgta       1980
cctggacttc atcgtactcg ggattttctt catctccctc cgcctcattg cctattttgt       2040
cctcaggtac aaaatccggg cagagaggta aaacacctga atgccaggaa acaggaagat       2100
tagacactgt ggccgagggc acgtctagaa tcgaggaggc aagcctgtgc cgaccgacg       2160 acacagagac tcttctgatc caaccccctag aaccgcgttg ggtttgtggg tgtctcgtgc       2220
tcagccactc tgcccagctg ggttggatct tctctccatt ccccttttcta gctttaacta       2280 ggaagatgta ggcagattgg tggttttttt tttttttaaca tacagaattt taaataccac       2340
aactggggca gaatttaaag ctgcaacaca gctggtgatg agaggcttcc tcagtccagt       2400
cgctccttag caccaggcac cgtgggtcct ggatggggaa ctgcaagcag cctctcagct       2460
gatggctgca cagtcagatg tctggtggca gagagtccga gcatggagcg attccatttt       2520
atgactgttg tttttcacat tttcatcttt ctaaggtgtg tctcttttcc aatgagaagt       2580
catttttgca agccaaaagt cgatcaatcg cattcatttt aagaaattat accttttttag       2640 tacttgctga agaatgattc agggtaaatc acatactttg tttagagagg cgagggtttt       2700
aaccgagtca cccagctggt ctcatacata gacagcactt gtgaaggatt gaatgcaggt       2760
tccaggtgga gggaagacgt ggacaccatc tccactgagc catgcagaca ttttttaaaag       2820 ctatacaaaa aattgtgaga agacattggc caactctttc aaagtctttc ttttttccacg       2880 tgcttcttat tttaagcgaa atatattgtt tgtttcttcc t                           2921
```

<210> SEQ ID NO 6
<211> LENGTH: 663
<212> TYPE: PRT

<213> ORGANISM: Human

<400> SEQUENCE: 6

```
Met Ile Met Arg Leu Pro Gln Pro His Gly Thr Asn Ala Ser Ser Tyr
 1               5                  10                  15

Ser Ala Glu Met Thr Glu Pro Lys Ser Val Cys Val Ser Val Asp Glu
            20                  25                  30

Val Val Ser Ser Asn Met Glu Ala Thr Glu Thr Asp Leu Leu Asn Gly
        35                  40                  45

His Leu Lys Lys Val Asp Asn Asn Leu Thr Glu Ala Gln Arg Phe Ser
    50                  55                  60

Ser Leu Pro Arg Arg Ala Ala Val Asn Ile Glu Phe Arg Asp Leu Ser
65                  70                  75                  80

Tyr Ser Val Pro Glu Gly Pro Trp Trp Arg Lys Lys Gly Tyr Lys Thr
                85                  90                  95

Leu Leu Lys Gly Ile Ser Gly Lys Phe Asn Ser Gly Glu Leu Val Ala
                100                 105                 110

Ile Met Gly Pro Ser Gly Ala Gly Lys Ser Thr Leu Met Asn Ile Leu
            115                 120                 125

Ala Gly Tyr Arg Glu Thr Gly Met Lys Gly Ala Val Leu Ile Asn Gly
        130                 135                 140

Leu Pro Arg Asp Leu Arg Cys Phe Arg Lys Val Ser Cys Tyr Ile Met
145                 150                 155                 160

Gln Asp Asp Met Leu Leu Pro His Leu Thr Val Gln Glu Ala Met Met
                165                 170                 175

Val Ser Ala His Leu Lys Leu Gln Glu Lys Asp Glu Gly Arg Arg Glu
                180                 185                 190

Met Val Lys Glu Ile Leu Thr Ala Leu Gly Leu Leu Ser Cys Ala Asn
            195                 200                 205

Thr Arg Thr Gly Ser Leu Ser Gly Gly Gln Arg Lys Arg Leu Ala Ile
        210                 215                 220

Ala Leu Glu Leu Val Asn Asn Pro Pro Val Met Phe Phe Asp Glu Pro
225                 230                 235                 240

Thr Ser Gly Leu Asp Ser Ala Ser Cys Phe Gln Val Val Ser Leu Met
                245                 250                 255

Lys Gly Leu Ala Gln Gly Gly Arg Ser Ile Ile Cys Thr Ile His Gln
                260                 265                 270

Pro Ser Ala Lys Leu Phe Glu Leu Phe Asp Gln Leu Tyr Val Leu Ser
            275                 280                 285

Gln Gly Gln Cys Val Tyr Arg Gly Lys Val Cys Asn Leu Val Pro Tyr
        290                 295                 300

Leu Arg Asp Leu Gly Leu Asn Cys Pro Thr Tyr His Asn Pro Ala Asp
305                 310                 315                 320

Phe Val Met Glu Val Ala Ser Gly Glu Tyr Gly Asp Gln Asn Ser Arg
                325                 330                 335

Leu Val Arg Ala Val Arg Glu Gly Met Cys Asp Ser Asp His Lys Arg
                340                 345                 350

Asp Leu Gly Gly Asp Ala Glu Val Asn Pro Phe Leu Trp His Arg Pro
            355                 360                 365

Ser Glu Glu Asp Ser Ser Met Glu Gly Cys His Ser Phe Ser Ala
        370                 375                 380

Ser Cys Leu Thr Gln Phe Cys Ile Leu Phe Lys Arg Thr Phe Leu Ser
385                 390                 395                 400
```

-continued

```
Ile Met Arg Asp Ser Val Leu Thr His Leu Arg Ile Thr Ser His Ile
            405                 410                 415
Gly Ile Gly Leu Leu Ile Gly Leu Leu Tyr Leu Gly Ile Gly Asn Glu
            420                 425                 430
Ala Lys Lys Val Leu Ser Asn Ser Gly Phe Leu Phe Ser Met Leu
            435                 440                 445
Phe Leu Met Phe Ala Ala Leu Met Pro Thr Val Leu Thr Phe Pro Leu
450                 455                 460
Glu Met Gly Val Phe Leu Arg Glu His Leu Asn Tyr Trp Tyr Ser Leu
465                 470                 475                 480
Lys Ala Tyr Tyr Leu Ala Lys Thr Met Ala Asp Val Pro Phe Gln Ile
                485                 490                 495
Met Phe Pro Val Ala Tyr Cys Ser Ile Val Tyr Trp Met Thr Ser Gln
                500                 505                 510
Pro Ser Asp Ala Val Arg Phe Val Leu Phe Ala Ala Leu Gly Thr Met
            515                 520                 525
Thr Ser Leu Val Ala Gln Ser Leu Gly Leu Leu Ile Gly Ala Ala Ser
            530                 535                 540
Thr Ser Leu Gln Val Ala Thr Phe Val Gly Pro Val Thr Ala Ile Pro
545                 550                 555                 560
Val Leu Leu Phe Ser Gly Phe Phe Val Ser Phe Asp Thr Ile Pro Thr
                565                 570                 575
Tyr Leu Gln Trp Met Ser Tyr Ile Ser Tyr Val Arg Tyr Gly Phe Glu
            580                 585                 590
Gly Val Ile Leu Ser Ile Tyr Gly Leu Asp Arg Glu Asp Leu His Cys
            595                 600                 605
Asp Ile Asp Glu Thr Cys His Phe Gln Lys Ser Glu Ala Ile Leu Arg
610                 615                 620
Glu Leu Asp Val Glu Asn Ala Lys Leu Tyr Leu Asp Phe Ile Val Leu
625                 630                 635                 640
Gly Ile Phe Phe Ile Ser Leu Arg Leu Ile Ala Tyr Phe Val Leu Arg
                645                 650                 655
Tyr Lys Ile Arg Ala Glu Arg
            660

<210> SEQ ID NO 7
<211> LENGTH: 1693
<212> TYPE: DNA
<213> ORGANISM: Drosophila

<400> SEQUENCE: 7
caacactttc agatctctcc aagcgttccg tgcatcatgt tgaccaggtc cattttatcc    60
gttgccgtgt gtggcctcct cctgtcgccc ctcctgccca tcacccgtgc gtcccaggag   120
gaggacaccg gcaaacagga caagcagttc accgtggaac tggacccaga accttcgac   180
actgcgattg ccggcggcaa tgtcttcgtc aagttctttg ctccatggtg cggccattgc   240
aagcgtattc agccgctgtg gaacagctg gccgagatca tgaatgtgga taaccccaag   300
gtgatcatcg ccaaggtgga ctgcaccaag caccagggac tctgcgccac gcaccaggtt   360
accggctatc ccacactgcg cctctttaag ctgggcgaag aggaatcggt caagtttaag   420
ggcactcgcg acttgccgc cattaccgat ttcatcaata ggaactgag cgcacccgct   480
gaggcggatc tgggcgaggt caagcgcgag caggtcgaga accttaatat tggcaaggtg   540
gttgaccta ccgaagacac ctttgccaag cacgtgtcca ccggcaatca ctttgtcaaa   600
```

-continued

```
ttctttgcac cctggtgcag tcattgtcag cgtttggcac ccacgtggga ggacctggcc    660
aaggagctga ttaaagagcc taccgtaact atctcgaaga tcgactgcac ccagttccgt    720
tccatctgcc aggactttga ggtcaagggg tatcccactc ttctctggat cgaggatggc    780
aaaaagattg aaaagtactc gggtgctcgc gatctgtcca cgctgaaaac gtacgtggag    840
aaaatggtgg gcgtgccact ggagaagacc gctggcgagg ccggcgatga aaggtggtt     900 atcgaggagg ttgccggcga ggaggacgca gccaagaagc tgactccaca acagctgact    960
ggcgaggacg agttcgacca agccattgcc gagggcgttg ccttcattaa gttctatgct    1020
ccgtggtgtg acactgcca gaagctgcaa cccacctggg agcagctggc cacggaaacg     1080
caccaggctc agagttccgt gaaaattgcc aaggttgact gcacggcgcc ggagaacaag    1140
caagtgtgca tcgaccagca ggtggagggc tatccaactc tcttccttta caagaatggt    1200
cagcgccaga acgagtacga aggcagccgc tcactgccgg agctgcaggc ctatctgaag    1260
aagttcctcg gccacgacga gctctaaagc atctgccggt tcacagggaa tcagcagtag    1320
tcgaatgatc aaataatcgc ccgccaaatt aattgtaatc gtaattttttc tttctccagc   1380 ataaacctct gtgaggagtc cgcatttaat caatatatcc aacaacaccc aaacgacaac    1440
gcgctagctg aaattgataa attcaatctg agttccttt acttttttttt cgttttttgtc   1500 cctcttcctt agctgttttt gtagaatttt ttttatactt atttgtttag tgtttacgta    1560
aatggggcac gggactgtgt gcgcgatgat aagccattta gcgaacttac atttcaattt    1620
taaagtcatt ttgagtagcc tacgttttag gaaaatttgt caacacaaag ctaataaata    1680
tcaattggaa aac                                                        1693
```

<210> SEQ ID NO 8
<211> LENGTH: 416
<212> TYPE: PRT
<213> ORGANISM: Drosophila

<400> SEQUENCE: 8

```
Met Leu Thr Arg Ser Ile Leu Ser Val Ala Val Cys Gly Leu Leu Leu
  1               5                  10                  15

Ser Pro Leu Leu Pro Ile Thr Arg Ala Ser Gln Glu Glu Asp Thr Gly
                 20                  25                  30

Lys Gln Asp Lys Gln Phe Thr Val Glu Leu Asp Pro Glu Thr Phe Asp
             35                  40                  45

Thr Ala Ile Ala Gly Gly Asn Val Phe Val Lys Phe Phe Ala Pro Trp
         50                  55                  60

Cys Gly His Cys Lys Arg Ile Gln Pro Leu Trp Glu Gln Leu Ala Glu
 65                  70                  75                  80

Ile Met Asn Val Asp Asn Pro Lys Val Ile Ala Lys Val Asp Cys
                 85                  90                  95

Thr Lys His Gln Gly Leu Cys Ala Thr His Gln Val Thr Gly Tyr Pro
            100                 105                 110

Thr Leu Arg Leu Phe Lys Leu Gly Glu Glu Ser Val Lys Phe Lys
            115                 120                 125

Gly Thr Arg Asp Leu Pro Ala Ile Thr Asp Phe Ile Asn Lys Glu Leu
        130                 135                 140

Ser Ala Pro Ala Glu Ala Asp Leu Gly Glu Val Lys Arg Glu Gln Val
145                 150                 155                 160

Glu Asn Leu Asn Ile Gly Lys Val Val Asp Leu Thr Glu Asp Thr Phe
                165                 170                 175
```

-continued

```
            Ala Lys His Val Ser Thr Gly Asn His Phe Val Lys Phe Phe Ala Pro
                    180                 185                 190

Trp Cys Ser His Cys Gln Arg Leu Ala Pro Thr Trp Glu Asp Leu Ala
                195                 200                 205

Lys Glu Leu Ile Lys Glu Pro Thr Val Thr Ile Ser Lys Ile Asp Cys
                210                 215                 220

Thr Gln Phe Arg Ser Ile Cys Gln Asp Phe Glu Val Lys Gly Tyr Pro
            225                 230                 235                 240

Thr Leu Leu Trp Ile Glu Asp Gly Lys Lys Ile Glu Lys Tyr Ser Gly
                            245                 250                 255

Ala Arg Asp Leu Ser Thr Leu Lys Thr Tyr Val Glu Lys Met Val Gly
                        260                 265                 270

Val Pro Leu Glu Lys Thr Ala Gly Glu Ala Gly Asp Glu Lys Val Val
                    275                 280                 285

Ile Glu Glu Val Ala Gly Glu Glu Asp Ala Ala Lys Lys Leu Thr Pro
                290                 295                 300

Gln Gln Leu Thr Gly Glu Asp Glu Phe Asp Gln Ala Ile Ala Glu Gly
            305                 310                 315                 320

Val Ala Phe Ile Lys Phe Tyr Ala Pro Trp Cys Gly His Cys Gln Lys
                            325                 330                 335

Leu Gln Pro Thr Trp Glu Gln Leu Ala Thr Glu Thr His Gln Ala Gln
                        340                 345                 350

Ser Ser Val Lys Ile Ala Lys Val Asp Cys Thr Ala Pro Glu Asn Lys
                    355                 360                 365

Gln Val Cys Ile Asp Gln Gln Val Glu Gly Tyr Pro Thr Leu Phe Leu
                370                 375                 380

Tyr Lys Asn Gly Gln Arg Gln Asn Glu Tyr Glu Gly Ser Arg Ser Leu
            385                 390                 395                 400

Pro Glu Leu Gln Ala Tyr Leu Lys Lys Phe Leu Gly His Asp Glu Leu
                            405                 410                 415

<210> SEQ ID NO 9
<211> LENGTH: 4487
<212> TYPE: DNA
<213> ORGANISM: Drosophila
<220> FEATURE:
<223> OTHER INFORMATION: Description of Artificial Sequence:primer

<400> SEQUENCE: 9
gaccgaagtt tgttttatta tttacaatat ctgtatatag ttttgtgtt gctttgccgg      60 gtcttctatc gcgattttct cacgttcgcc agcaacaata accatattgt tgaatgtaaa    120
caatattgaa acaaaatttc tttagaggca gtagaacatg cagtcgctga aaacggcaga    180
tttgccggaa aatccccggg aacattgcaa ttttatttcg gcagcatgtt tttggtacac    240
catgccgact tttatcaagg gtcggaaacg cacattggat accaaggatc tttacagagc    300
cttaaaagag cacaaatctg agactctggg aacaaattg tgcgcttcct gggaattgga     360
acttgagaag accaaaggaa agcccaattt gttgagagcc cttctgcgag ttttggctg     420 gtacttcgca ctgcttggcc tggtgctttt cctgctggaa ttgggtcttc gaacgcttca    480
gccaatcttc ctgctgaaac tcatcgccta ctacacacat ggctcggaat cgattgaatc    540
ggcctattac tatgcagctg gagtgatcct gtgcagtgcc ctcaatgtca ttataatgca    600
tccctatatg ctaggcacaa tgcatgtggg actcaagatg cgcgttggta tgtgcagcat    660
gatctaccgc aaggcgttac ggctgagtaa gtcggcgttg ggagacacca cagctggaca    720
```

-continued

| | |
|---|---|
| tgtggtgaat cttatgtcca acgacgtggg acgtctcgat ctggctacca tattcgtaca | 780 |
| ctacttgtgg gtgggaccgc tggagaccct ctttatcaca tacctaatgt accgtgagat | 840 |
| tggaatcgct gctgtgtttg gtgtggcctt catgttgctg ttcatccccc tgcaggcgta | 900 |
| tctgggaaaa agaacatcgg tgttgcgact cagaaccgcc ttacgcacgg atgaaagggt | 960 |
| acggatgatg aacgaaatca tctcgggcat tcaggtgatt aaaatgtacg catgggaatt | 1020 |
| gccattcgaa catatggtgg cctttgcccg taagaaggag ataaatgcca tccgccatgt | 1080 |
| gtcctacatc cgtggaattc tgctctcctt catcatcttt ctgacgcgtg tctcaatttt | 1140 |
| cctgagtctg gtgggatatg ttctgctcgg gacgttccta accccggaag tggcgttctt | 1200 |
| gatcacagcc tactacaata tcctgcgtac cactatgacg gtgttctttc cccagggcat | 1260 |
| ttcccaaatg gcggagaccc tggtgtccat taagcgtgtc cagaagtata tgcagtccga | 1320 |
| cgagacgaat gtgatggata tgagtgtgga tcttaccgag gatttccaag gaagcaatca | 1380 |
| ggaaacggtt catgccgatg gagatgagga gcgcgacgaa gctgaggata gcttttagg | 1440 |
| tccaccaatt gccactgtta atgagaacgc caagttgtcg gaggcgggaa tctctattag | 1500 |
| cggacttatg gccaaatggg atgttaactc ccccgattac tcgcttaatg gtgtaaacct | 1560 |
| tcgtgttcag cctggaacca tgctgggtat tgtcggacgc actggatccg gtaaatccag | 1620 |
| tctcatccaa gccatccttg gtgaactgcc cgcagagtct ggcgagataa aggttaatgg | 1680 |
| ctccatgtcg tatgcttccc aagaaccgtg gctcttttcc ggcactgtgc gacaaaatat | 1740 |
| tctctttggc cagcctatgg atcgtcgtcg ttacgctaag gtggtgaaga aatgtgccct | 1800 |
| ggagcgagat ttcgagctgc tcccgtttaa ggataaaacc atagttggag agcgtggagc | 1860 |
| ttccctgtcg ggtggccaaa aggcgagaat cagtttggca agagctgttt atcgggagac | 1920 |
| ctccatatac ctgctggatg atcctctgag tgccgtggac acccatgtgg cccgccatct | 1980 |
| gttcgagcag tgcatgcgtg gctatctacg cgagcgaatt gttatattgg ccactcatca | 2040 |
| gctccagttt ttgcagcacg ccgatcagat tgtcatcatg gataagggtc gtgtaagcgc | 2100 |
| cgtgggcacc tacagtgtctc tacgcgaatc cgggttggac ttcgcctcca tgctagccga | 2160 |
| tccagagcgg gatgagcaat cagaggagcg atcacggtcg cgatcgggca gctacaccca | 2220 |
| cagtcattcg gaccagcgac gcaacagcga gcaatcccta ctttccatgg cagattcgtg | 2280 |
| catggatgac ctcgaagcgg agcaagctaa caaccaggaa cgccaggagg ctggtcaaat | 2340 |
| cggcctgcgc ttgtacagca aatacttcaa agcgggaggc ggtttcttcg ccttcttcgt | 2400 |
| gatgatgggc ttctgtgtgc tctcgcaagg attggcctct ctgggtgact attttctctc | 2460 |
| atattgggtt accaaaaagg gaaatgtggc ttaccgtgca gataataatg acacaactcg | 2520 |
| ctctgaggaa ctcgaacctc gtctgtcgac atggcttcgt gatataggat tgtccgtgga | 2580 |
| tgctgaaatg ctggatactt atatattcac ggtgatcaca gtactgacca tcctggtgac | 2640 |
| cgtggctcgc tcgttttat tctttaattt ggccatgaaa gcctcaattc gtttgcacaa | 2700 |
| ttccatgttc cgcggcatca cccgagctgc catgtacttc ttcaatacga atccatctgg | 2760 |
| gcgcattcta aaccgtttct caaaggatat gggacaagtt gacgagatac tgcctgccgt | 2820 |
| gatgatggat gtcatccaga ttttccttgc acttgctggc attgtgatcg tcatagccgt | 2880 |
| tgtcaatccg ctgttcctta ttccaaccgt agtactgggg attattttct atcaactgcg | 2940 |
| cacctttat ctaaagacat caagggatgt aaagcgcatg gaagcaatta ctcggtctcc | 3000 |
| agtatactcg catttagctg cctcgttgac cggtctgtcc accattcgtg cctttggagc | 3060 |
| ccaacgtgtt ctggaggcgg agttcgacaa ttaccaggat atgcatagct ccgcatttta | 3120 |

-continued

```
tatgttcatt agcacctcgc gagccttcgg atattggctt gactgtttct gtgtgattta    3180
catagccata attactctca gtttcttcat ctttcctcct gcgaacggag gcgatgtggg    3240
actggccatt acgcaggcaa tgggaatgac cggcatggtt cagtggggaa tgcgtcagtc    3300
agccgagctg gagaatacga tgacagctgt ggagcgagtg gttgagtacg aggacattga    3360
accggaagga gcgttggaag ctccggccga taagaagcca ccaaagtcat ggccagagca    3420
gggaaaaatc gttttcgacg agcttagctt gcgctatacg ccggatccaa gtcggagaa    3480 tgtgctcaag tcacttagtt tcgtaataaa acctaaggag aaagtaggca tcgtgggacg    3540
cactggagcg ggaaagtctt cgctgattaa tgccctgttc cgactgtcct acaacgatgg    3600
atctgtgctc atagacaaga gggataccag tgagatgggt ttgcatgacc tgcgcagcaa    3660
aatctcgatc ataccgcagg aacccgttct gttttccggc actatgcgat acaacttgga    3720
tcccttcgac gagtatagcg atgataagct gtggcgctcc ctggaggagg taaagctaaa    3780
ggaggtggtt gctgatcttc ccagtggctt gcagagcaaa atcaccgagg gcggaaccaa    3840
cttcagcgtt ggccagcgcc agttggtctg cttggcacgg gctatactgc gtgaaaatcg    3900
tatcctggta atggacgagg ctacggccaa tgtggatccc cagacagatg gcctcatcca    3960
aaccaccata cgaaacaagt tcaaggagtg cactgtgctg acgatagctc atcgtttgca    4020
caccatcatg gactcggaca aagtcttggt gatggacgct ggtcgagcgg tggagtttgg    4080
aacgccctat gaactgctga cgctggcgga ttctaaggtg ttccacggta tggtgaagca    4140
aacgggtcac gccacctatg agagtctgct gaaaatcgcc caaaaggcat tcgaaaacag    4200
gcagaatcac agtctttcct cgtgagaatc agctattatg tgtttgtcac cgaatcttta    4260
gctggctaat catagtttaa gtaatcataa tgtttttgaa tgtgttattt tgtgtgaatg    4320
tatatatgtt tttccgtgtg tgtgtgttaa aactttata tatgtaactt aaaaactgta    4380
taggaaacct ttgtttaatc tactatttgt atttattaaa cattcactaa gagcaaagat    4440
gtgccttaaa aaataaatga aatatttctc tgttcctaa tctacaa                  4487
```

<210> SEQ ID NO 10
<211> LENGTH: 1355
<212> TYPE: PRT
<213> ORGANISM: Drosophila

<400> SEQUENCE: 10

```
Met Gln Ser Leu Lys Thr Ala Asp Leu Pro Glu Asn Pro Arg Glu His
 1               5                  10                  15

Cys Asn Phe Ile Ser Ala Ala Cys Phe Trp Tyr Thr Met Pro Thr Phe
                20                  25                  30

Ile Lys Gly Arg Lys Arg Thr Leu Asp Thr Lys Asp Leu Tyr Arg Ala
            35                  40                  45

Leu Lys Glu His Lys Ser Glu Thr Leu Gly Asn Lys Leu Cys Ala Ser
        50                  55                  60

Trp Glu Leu Glu Leu Glu Lys Thr Lys Gly Lys Pro Asn Leu Leu Arg
 65                  70                  75                  80

Ala Leu Leu Arg Val Phe Gly Trp Tyr Phe Ala Leu Gly Leu Val
                85                  90                  95

Leu Phe Leu Leu Glu Leu Gly Leu Arg Thr Leu Gln Pro Ile Phe Leu
               100                 105                 110

Leu Lys Leu Ile Ala Tyr Tyr Thr His Gly Ser Glu Ser Ile Glu Ser
           115                 120                 125
```

```
Ala Tyr Tyr Tyr Ala Ala Gly Val Ile Leu Cys Ser Ala Leu Asn Val
130                 135                 140
Ile Ile Met His Pro Tyr Met Leu Gly Thr Met His Val Gly Leu Lys
145                 150                 155                 160
Met Arg Val Gly Met Cys Ser Met Ile Tyr Arg Lys Ala Leu Arg Leu
                165                 170                 175
Ser Lys Ser Ala Leu Gly Asp Thr Thr Ala Gly His Val Val Asn Leu
            180                 185                 190
Met Ser Asn Asp Val Gly Arg Leu Asp Leu Ala Thr Ile Phe Val His
        195                 200                 205
Tyr Leu Trp Val Gly Pro Leu Glu Thr Leu Phe Ile Thr Tyr Leu Met
    210                 215                 220
Tyr Arg Glu Ile Gly Ile Ala Ala Val Phe Gly Val Ala Phe Met Leu
225                 230                 235                 240
Leu Phe Ile Pro Leu Gln Ala Tyr Leu Gly Lys Arg Thr Ser Val Leu
                245                 250                 255
Arg Leu Arg Thr Ala Leu Arg Thr Asp Glu Arg Val Arg Met Met Asn
            260                 265                 270
Glu Ile Ile Ser Gly Ile Gln Val Ile Lys Met Tyr Ala Trp Glu Leu
        275                 280                 285
Pro Phe Glu His Met Val Ala Phe Ala Arg Lys Lys Glu Ile Asn Ala
    290                 295                 300
Ile Arg His Val Ser Tyr Ile Arg Gly Ile Leu Leu Ser Phe Ile Ile
305                 310                 315                 320
Phe Leu Thr Arg Val Ser Ile Phe Leu Ser Leu Val Gly Tyr Val Leu
                325                 330                 335
Leu Gly Thr Phe Leu Thr Pro Glu Val Ala Phe Leu Ile Thr Ala Tyr
            340                 345                 350
Tyr Asn Ile Leu Arg Thr Thr Met Thr Val Phe Phe Pro Gln Gly Ile
        355                 360                 365
Ser Gln Met Ala Glu Thr Leu Val Ser Ile Lys Arg Val Gln Lys Tyr
    370                 375                 380
Met Gln Ser Asp Glu Thr Asn Val Met Asp Met Ser Val Asp Leu Thr
385                 390                 395                 400
Glu Asp Phe Gln Gly Ser Asn Gln Glu Thr Val His Ala Asp Gly Asp
                405                 410                 415
Glu Glu Arg Asp Glu Ala Glu Asp Lys Leu Leu Gly Pro Pro Ile Ala
            420                 425                 430
Thr Val Asn Glu Asn Ala Lys Leu Ser Glu Ala Gly Ile Ser Ile Ser
        435                 440                 445
Gly Leu Met Ala Lys Trp Asp Val Asn Ser Pro Asp Tyr Ser Leu Asn
    450                 455                 460
Gly Val Asn Leu Arg Val Gln Pro Gly Thr Met Leu Gly Ile Val Gly
465                 470                 475                 480
Arg Thr Gly Ser Gly Lys Ser Ser Leu Ile Gln Ala Ile Leu Gly Glu
                485                 490                 495
Leu Pro Ala Glu Ser Gly Glu Ile Lys Val Asn Gly Ser Met Ser Tyr
            500                 505                 510
Ala Ser Gln Glu Pro Trp Leu Phe Ser Gly Thr Val Arg Gln Asn Ile
        515                 520                 525
Leu Phe Gly Gln Pro Met Asp Arg Arg Tyr Ala Lys Val Val Lys
    530                 535                 540
Lys Cys Ala Leu Glu Arg Asp Phe Glu Leu Leu Pro Phe Lys Asp Lys
```

-continued

```
            545                 550                 555                 560
        Thr Ile Val Gly Glu Arg Gly Ala Ser Leu Ser Gly Gln Lys Ala
                        565                 570                 575

Arg Ile Ser Leu Ala Arg Ala Val Tyr Arg Glu Thr Ser Ile Tyr Leu
                    580                 585                 590

Leu Asp Asp Pro Leu Ser Ala Val Asp Thr His Val Ala Arg His Leu
                    595                 600                 605

Phe Glu Gln Cys Met Arg Gly Tyr Leu Arg Glu Arg Ile Val Ile Leu
                610                 615                 620

Ala Thr His Gln Leu Gln Phe Leu Gln His Ala Asp Gln Ile Val Ile
        625                 630                 635                 640

Met Asp Lys Gly Arg Val Ser Ala Val Gly Thr Tyr Glu Ser Leu Arg
                        645                 650                 655

Glu Ser Gly Leu Asp Phe Ala Ser Met Leu Ala Asp Pro Glu Arg Asp
                        660                 665                 670

Glu Gln Ser Glu Glu Arg Ser Arg Ser Arg Ser Gly Ser Tyr Thr His
                    675                 680                 685

Ser His Ser Asp Gln Arg Asn Ser Glu Gln Ser Leu Leu Ser Met
                690                 695                 700

Ala Asp Ser Cys Met Asp Asp Leu Glu Ala Glu Gln Ala Asn Asn Gln
        705                 710                 715                 720

Glu Arg Gln Glu Ala Gly Gln Ile Gly Leu Arg Leu Tyr Ser Lys Tyr
                        725                 730                 735

Phe Lys Ala Gly Gly Phe Ala Phe Val Met Met Gly Phe
                    740                 745                 750

Cys Val Leu Ser Gln Gly Leu Ala Ser Leu Gly Asp Tyr Phe Leu Ser
                    755                 760                 765

Tyr Trp Val Thr Lys Gly Asn Val Ala Tyr Arg Ala Asp Asn Asn
            770                 775                 780

Asp Thr Thr Arg Ser Glu Glu Leu Glu Pro Arg Leu Ser Thr Trp Leu
        785                 790                 795                 800

Arg Asp Ile Gly Leu Ser Val Asp Ala Glu Met Leu Asp Thr Tyr Ile
                        805                 810                 815

Phe Thr Val Ile Thr Val Leu Thr Ile Leu Val Thr Val Ala Arg Ser
                    820                 825                 830

Phe Leu Phe Phe Asn Leu Ala Met Lys Ala Ser Ile Arg Leu His Asn
                    835                 840                 845

Ser Met Phe Arg Gly Ile Thr Arg Ala Ala Met Tyr Phe Phe Asn Thr
            850                 855                 860

Asn Pro Ser Gly Arg Ile Leu Asn Arg Phe Ser Lys Asp Met Gly Gln
        865                 870                 875                 880

Val Asp Glu Ile Leu Pro Ala Val Met Met Asp Val Ile Gln Ile Phe
                        885                 890                 895

Leu Ala Leu Ala Gly Ile Val Ile Ala Val Val Asn Pro Leu
                    900                 905                 910

Phe Leu Ile Pro Thr Val Val Leu Gly Ile Ile Phe Tyr Gln Leu Arg
                    915                 920                 925

Thr Phe Tyr Leu Lys Thr Ser Arg Asp Val Lys Arg Met Glu Ala Ile
                930                 935                 940

Thr Arg Ser Pro Val Tyr Ser His Leu Ala Ala Ser Leu Thr Gly Leu
        945                 950                 955                 960

Ser Thr Ile Arg Ala Phe Gly Ala Gln Arg Val Leu Glu Ala Glu Phe
                        965                 970                 975
```

```
Asp Asn Tyr Gln Asp Met His Ser Ser Ala Phe Tyr Met Phe Ile Ser
            980                 985                 990

Thr Ser Arg Ala Phe Gly Tyr Trp Leu Asp Cys Phe Cys Val Ile Tyr
        995                1000                1005

Ile Ala Ile Ile Thr Leu Ser Phe Phe Ile Phe Pro Pro Ala Asn Gly
1010                1015                1020

Gly Asp Val Gly Leu Ala Ile Thr Gln Ala Met Gly Met Thr Gly Met
1025                1030                1035                1040

Val Gln Trp Gly Met Arg Gln Ser Ala Glu Leu Glu Asn Thr Met Thr
            1045                1050                1055

Ala Val Glu Arg Val Val Glu Tyr Glu Asp Ile Glu Pro Glu Gly Ala
        1060                1065                1070

Leu Glu Ala Pro Ala Asp Lys Lys Pro Pro Lys Ser Trp Pro Glu Gln
    1075                1080                1085

Gly Lys Ile Val Phe Asp Glu Leu Ser Leu Arg Tyr Thr Pro Asp Pro
1090                1095                1100

Lys Ser Glu Asn Val Leu Lys Ser Leu Ser Phe Val Ile Lys Pro Lys
1105                1110                1115                1120

Glu Lys Val Gly Ile Val Gly Arg Thr Gly Ala Gly Lys Ser Ser Leu
            1125                1130                1135

Ile Asn Ala Leu Phe Arg Leu Ser Tyr Asn Asp Gly Ser Val Leu Ile
        1140                1145                1150

Asp Lys Arg Asp Thr Ser Glu Met Gly Leu His Asp Leu Arg Ser Lys
    1155                1160                1165

Ile Ser Ile Ile Pro Gln Glu Pro Val Leu Phe Ser Gly Thr Met Arg
    1170                1175                1180

Tyr Asn Leu Asp Pro Phe Asp Glu Tyr Ser Asp Asp Lys Leu Trp Arg
1185                1190                1195                1200

Ser Leu Glu Glu Val Lys Leu Lys Glu Val Val Ala Asp Leu Pro Ser
            1205                1210                1215

Gly Leu Gln Ser Lys Ile Thr Glu Gly Gly Thr Asn Phe Ser Val Gly
        1220                1225                1230

Gln Arg Gln Leu Val Cys Leu Ala Arg Ala Ile Leu Arg Glu Asn Arg
    1235                1240                1245

Ile Leu Val Met Asp Glu Ala Thr Ala Asn Val Asp Pro Gln Thr Asp
    1250                1255                1260

Gly Leu Ile Gln Thr Thr Ile Arg Asn Lys Phe Lys Glu Cys Thr Val
1265                1270                1275                1280

Leu Thr Ile Ala His Arg Leu His Thr Ile Met Asp Ser Asp Lys Val
            1285                1290                1295

Leu Val Met Asp Ala Gly Arg Ala Val Glu Phe Gly Thr Pro Tyr Glu
        1300                1305                1310

Leu Leu Thr Leu Ala Asp Ser Lys Val Phe His Gly Met Val Lys Gln
    1315                1320                1325

Thr Gly His Ala Thr Tyr Glu Ser Leu Leu Lys Ile Ala Gln Lys Ala
    1330                1335                1340

Phe Glu Asn Arg Gln Asn His Ser Leu Ser Ser
1345                1350                1355

<210> SEQ ID NO 11
<211> LENGTH: 2459
<212> TYPE: DNA
<213> ORGANISM: Drosophila
```

-continued

<400> SEQUENCE: 11

| | | | | | |
|---|---|---|---|---|---|
| cgtggcgagc | gcacgtgcag | cggaacgtat | atattcttgt | tcagcgggat | cggaatcggg | 60 |
| gaaaatcgag | acatatacag | aaatcgaagc | acattatgta | taacacacgc | aattgaaatt | 120 |
| aatttacgcg | tcgctgccca | tctgcataag | ttcaatggaa | gcagaggcaa | aagtttgagc | 180 |
| aaaagcacag | accgcgtacc | gagaggaaaa | gtagaaaaat | gtgaagaaag | tgcaacaaag | 240 |
| tcgaattagt | aaatcaacca | aaaaaaaaaa | atacaagaag | tgcacctaac | aacaataaaa | 300 |
| taaaacaatc | atcgcgtgtt | cgtccatatg | ttaaacaaag | gttaattaaa | cagactgcaa | 360 |
| ttattccgcg | ttgcagttgg | cagttggtgg | agtacaagaa | acatttcttt | gtgtttatgt | 420 |
| gttttcattc | agaaatattc | gttacgcgtc | tactcttacg | acttcccgag | aagaatccga | 480 |
| ataatttgtg | tactactgcg | aagaaagaga | cgctgaagag | cttgcagtca | agagataccc | 540 |
| cttctgacta | gaaacattga | ggattccgtg | caaacatgac | cctcttgcca | gacatcaagg | 600 |
| catcggatgc | cgcctgctgc | gtgggaggtc | gaacagcgca | tgccagcagc | agttccggcg | 660 |
| tctgcagcct | caagggtcac | catggtgacc | ccgacagcgg | ttgcctgggc | atcaactgtt | 720 |
| gcaccacggc | ggccagctcg | gagctgtcca | tcgacgagcg | gtcatcgacc | tcgtccagag | 780 |
| gctcctgcga | gttgaccagc | aaggtgacca | acgacctgaa | cggattccag | agtccgaact | 840 |
| accaccaggc | ggtggcgcac | gccaacttcg | accactgcga | tcccgtggac | atccagttcg | 900 |
| ccgacgtgcg | ctacacagtg | aagaagttct | ccttcccgga | gcggaagttc | gtcaccaagg | 960 |
| agatccttca | tggcctgaac | ggcagcttcc | ggtctggcga | actcacagcc | atcatgggtc | 1020 |
| cttcgggcgc | cggcaagagc | acgctgctga | atgtgatgtc | cggattttgt | aatggacgtg | 1080 |
| gtggtaaaga | cgatgcccca | ggcggtacac | gggttttcat | tgctaaacgt | tatcgctcca | 1140 |
| ctggcgtgtc | gggcgatatc | cgggttaata | gaaagcccat | ggctcccagc | tccgagaggt | 1200 |
| tccgccaaat | gctgtgctac | atccaccagg | acgatctgct | cgtccacag | ctgttggtcg | 1260 |
| gcgagataat | gctgctggcg | gcacatctga | agctgggctt | caaggtcacc | aaggcgtaca | 1320 |
| agatggatct | gatcaagcac | atcttatcgc | tgctgggtct | ggaccatcgc | tacaatgtgc | 1380 |
| ccactgggaa | gctttcgggt | ggccagaaga | agcgactcgc | aatcgccctg | gagctgataa | 1440 |
| gtaatcctcc | cgtgctatat | ctggatgagc | cgacgactgg | cctggacagc | tcctcgtgca | 1500 |
| gctcctgcgt | ggctctgctg | aagaaactgg | cgtcgcaggg | ccacacgata | gtctgcacca | 1560 |
| tccatcagcc | aagtgccctc | atcttcgaga | tgttcgacaa | gctctacacc | gtcgtcgatg | 1620 |
| gccactgcat | gtaccaagga | cctgtgcgcg | aactggtgcc | cttcctggcc | gaccagcagc | 1680 |
| tcgtctgccc | gagttaccac | aacccagctg | actatctact | ggaagtggcc | gtgggcgagc | 1740 |
| atcaacgtga | cctgaatgag | ctaatccatg | cggccaataa | aaagtattac | gaggatgtgg | 1800 |
| atcgccatag | gtatatgagc | agtgatgata | tggcacgcct | cgtggaaagc | attaaagaaa | 1860 |
| acatgggcgg | caaggcagtg | gtaaaaacca | gtgaagcgct | ggcagcattt | gcggcggcgc | 1920 |
| aattctccag | cttcgactat | gtaaagccct | cgccgcagga | gctggctctg | gaggagatca | 1980 |
| aggcactgag | cggcggcccc | gagagcgcgg | atcccgatct | cctcgagaaa | atctgaggc | 2040 |
| cacagccaca | gccgcttgcc | aaagccggtg | agcttgccag | gccgccgaat | gccattcgat | 2100 |
| cggcctcgtt | cctcatgcag | tatgtgctcc | tgatgcagcg | catcttgatt | tgcgccaagc | 2160 |
| gaaactactt | tctgctgctg | gcccgcatct | tctcgcacat | tttcatcgga | gtcgtcttcg | 2220 |
| ggtatctgta | catgaacgtg | ggcaacaatg | cccagagtgt | gctgggaaac | tacgtgtatc | 2280 |
| tgtacggctc | cacgctgctc | ttggtctaca | ccggtaaaat | ggctgtggtc | ttgacatttc | 2340 |

```
cgctggaaat tgacatgttg acacgggagc acttcaaccg ctggtacaaa ctgggtccct    2400
acttcctctc gttgatctcc ttcgaaatac ccttccaggt gagcaccgcc atagaatag     2459
```

<210> SEQ ID NO 12
<211> LENGTH: 627
<212> TYPE: PRT
<213> ORGANISM: Drosophila

<400> SEQUENCE: 12

```
Met Thr Leu Leu Pro Asp Ile Lys Ala Ser Asp Ala Ala Cys Cys Val
 1               5                  10                  15

Gly Gly Ala Asn Ser Asp Ala Ser Ser Ser Gly Val Cys Ser Leu
            20                  25                  30

Lys Gly His His Gly Asp Pro Asp Ser Gly Cys Leu Gly Ile Asn Cys
        35                  40                  45

Cys Thr Thr Ala Ala Ser Ser Glu Leu Ser Ile Asp Glu Thr Ser Ser
    50                  55                  60

Thr Ser Ser Arg Gly Ser Cys Glu Leu Thr Ser Lys Val Thr Asn Asp
65                  70                  75                  80

Leu Asn Gly Phe Gln Ser Pro Asn Tyr His Gln Ala Val Ala His Ala
                85                  90                  95

Asn Phe Asp His Cys Asp Pro Val Asp Ile Gln Phe Ala Asp Val Arg
            100                 105                 110

Tyr Thr Val Lys Lys Phe Ser Phe Pro Glu Arg Lys Phe Val Thr Lys
        115                 120                 125

Glu Ile Leu His Gly Leu Asn Gly Ser Phe Arg Ser Gly Glu Leu Thr
    130                 135                 140

Ala Ile Met Gly Pro Ser Gly Ala Gly Lys Ser Thr Leu Leu Asn Val
145                 150                 155                 160

Met Ser Gly Phe Cys Asn Gly Arg Gly Gly Lys Asp Asp Ala Pro Gly
                165                 170                 175

Gly Thr Arg Val Phe Ile Ala Lys Arg Tyr Arg Ser Thr Gly Val Ser
            180                 185                 190

Gly Asp Ile Arg Val Asn Arg Lys Pro Met Ala Pro Ser Ser Glu Arg
        195                 200                 205

Phe Arg Gln Met Leu Cys Tyr Ile His Gln Asp Asp Leu Leu Arg Pro
    210                 215                 220

Gln Leu Leu Val Gly Glu Ile Met Leu Leu Ala Ala His Leu Lys Leu
225                 230                 235                 240

Gly Phe Lys Val Thr Lys Ala Tyr Lys Met Asp Leu Ile Lys His Ile
                245                 250                 255

Leu Ser Leu Leu Gly Leu Asp His Arg Tyr Asn Val Pro Thr Gly Lys
            260                 265                 270

Leu Ser Gly Gly Gln Lys Lys Arg Leu Ala Ile Ala Leu Glu Leu Ile
        275                 280                 285

Ser Asn Pro Pro Val Leu Tyr Leu Asp Glu Pro Thr Thr Gly Leu Asp
    290                 295                 300

Ser Ser Ser Cys Ser Ser Cys Val Ala Leu Leu Lys Lys Leu Ala Ser
305                 310                 315                 320

Gln Gly His Thr Ile Val Cys Thr Ile His Gln Pro Ser Ala Leu Ile
                325                 330                 335

Phe Glu Met Phe Asp Lys Leu Tyr Thr Val Val Asp Gly His Cys Met
            340                 345                 350
```

```
Tyr Gln Gly Pro Val Arg Glu Leu Val Pro Phe Leu Ala Asp Gln Gln
        355                 360                 365

Leu Val Cys Pro Ser Tyr His Asn Pro Ala Asp Tyr Leu Leu Glu Val
    370                 375                 380

Ala Val Gly Glu His Gln Arg Asp Leu Asn Glu Leu Ile His Ala Ala
385                 390                 395                 400

Asn Lys Lys Tyr Tyr Glu Asp Val Asp Arg His Arg Tyr Met Ser Ser
                405                 410                 415

Asp Asp Met Ala Arg Leu Val Glu Ser Ile Lys Glu Asn Met Gly Gly
            420                 425                 430

Lys Ala Val Lys Thr Ser Glu Ala Leu Ala Ala Phe Ala Ala Ala
        435                 440                 445

Gln Phe Ser Ser Phe Asp Tyr Val Lys Pro Ser Pro Gln Glu Leu Ala
    450                 455                 460

Leu Glu Glu Ile Lys Ala Leu Ser Gly Gly Pro Glu Ser Ala Asp Pro
465                 470                 475                 480

Asp Leu Leu Glu Lys Asn Leu Arg Pro Gln Pro Gln Pro Leu Ala Lys
                485                 490                 495

Ala Gly Glu Leu Ala Arg Pro Pro Asn Ala Ile Arg Ser Ala Ser Phe
            500                 505                 510

Leu Met Gln Tyr Val Leu Leu Met Gln Arg Ile Leu Ile Cys Ala Lys
        515                 520                 525

Arg Asn Tyr Phe Leu Leu Leu Ala Arg Ile Phe Ser His Ile Phe Ile
    530                 535                 540

Gly Val Val Phe Gly Tyr Leu Tyr Met Asn Val Gly Asn Asn Ala Gln
545                 550                 555                 560

Ser Val Leu Gly Asn Tyr Val Tyr Leu Tyr Gly Ser Thr Leu Leu Leu
                565                 570                 575

Val Tyr Thr Gly Lys Met Ala Val Val Leu Thr Phe Pro Leu Glu Ile
            580                 585                 590

Asp Met Leu Thr Arg Glu His Phe Asn Arg Trp Tyr Lys Leu Gly Pro
        595                 600                 605

Tyr Phe Leu Ser Leu Ile Ser Phe Glu Ile Pro Phe Gln Val Ser Thr
    610                 615                 620

Ala Ile Glu
625

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 13
cacgggtgac aagggca                                                17

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 14
cccctgtgca atagtgtcct c                                           21
```

```
<210> SEQ ID NO 15
<211> LENGTH: 25
<212> TYPE: DNA
<213> ORGANISM: Artificial Sequence
<220> FEATURE:
<221> NAME/KEY: misc_binding
<222> LOCATION: (1)
<223> OTHER INFORMATION: 5(6)-FAM (5-(and-6)-carboxyfluorescein
<220> FEATURE:
<221> NAME/KEY: misc_binding
<222> LOCATION: (25)
<223> OTHER INFORMATION: 5(6)-TAMRA
      (5-(and-6)-carboxytetramethylrhodamine
<220> FEATURE:
<223> OTHER INFORMATION: Description of Artificial Sequence:taqman probe

<400> SEQUENCE: 15
tgctggcact caccgagaag agctt                                          25

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 16
caagtagcgc ccacccc                                                   17

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 17
agttcacatt gtcgaagacg atga                                           24

<210> SEQ ID NO 18
<211> LENGTH: 19
<212> TYPE: DNA
<213> ORGANISM: Artificial Sequence
<220> FEATURE:
<221> NAME/KEY: misc_binding
<222> LOCATION: (1)
<223> OTHER INFORMATION: 5(6)-FAM (5-(and-6)-carboxyfluorescein
<220> FEATURE:
<221> NAME/KEY: misc_binding
<222> LOCATION: (19)
<223> OTHER INFORMATION: 5(6)-TAMRA
      (5-(and-6)-carboxytetramethylrhodamine
<220> FEATURE:
<223> OTHER INFORMATION: Description of Artificial Sequence:taqman probe

<400> SEQUENCE: 18
aggctggccc cacgaggga                                                 19

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 19
tcgtatactg gatgacgtcc ca                                             22

<210> SEQ ID NO 20
```

```
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 20
tggtacccag agcagcgaac                                              20

<210> SEQ ID NO 21
<211> LENGTH: 21
<212> TYPE: DNA
<213> ORGANISM: Artificial Sequence
<220> FEATURE:
<221> NAME/KEY: misc_binding
<222> LOCATION: (21)
<223> OTHER INFORMATION: 5(6)-TAMRA
      (5-(and-6)-carboxytetramethylrhodamine
<220> FEATURE:
<221> NAME/KEY: misc_binding
<222> LOCATION: (1)
<223> OTHER INFORMATION: 5(6)-FAM (5-(and-6)-carboxyfluorescein
<220> FEATURE:
<223> OTHER INFORMATION: Description of Artificial Sequence:taqman probe

<400> SEQUENCE: 21
ccgtcggacg ctgtgcgttt t                                            21
```